United States Patent [19]

Kurome et al.

[11] Patent Number: 5,633,345
[45] Date of Patent: May 27, 1997

[54] CYCLIC PEPTIDES

[75] Inventors: Toru Kurome, Otsu; Kazutoh Takesako, Kusatsu; Ikunoshin Kato, Uji; Kaoru Inami, Minoh; Tetsuo Shiba, Toyonaka, all of Japan

[73] Assignee: Takara Shuzo Co., Ltd., Kyoto, Japan

[21] Appl. No.: 433,067

[22] Filed: May 3, 1995

Related U.S. Application Data

[62] Division of Ser. No. 67,018, May 26, 1993, abandoned.

[30] Foreign Application Priority Data

Jun. 19, 1992 [JP] Japan .................. 4-184661
Oct. 16, 1992 [JP] Japan .................. 4-303177

[51] Int. Cl.$^6$ .................................. A61K 38/12
[52] U.S. Cl. ........................................ 530/317
[58] Field of Search ............................. 530/317

[56] References Cited

U.S. PATENT DOCUMENTS

| | | | |
|---|---|---|---|
| 4,102,877 | 7/1978 | Nutt ................... | 260/112.5 |
| 4,703,034 | 10/1987 | Freidinger et al. ......... | 514/11 |
| 4,798,823 | 1/1989 | Witzel ................ | 514/11 |
| 4,914,188 | 4/1990 | Dumont et al. .......... | 530/317 |
| 5,057,493 | 10/1991 | Takesako et al. ......... | 514/11 |
| 5,116,816 | 5/1992 | Dreyfuss et al. ......... | 514/11 |
| 5,158,876 | 10/1992 | Takesako et al. ........ | 435/71.1 |
| 5,200,505 | 4/1993 | Takesako et al. ........ | 530/323 |

FOREIGN PATENT DOCUMENTS

| | | |
|---|---|---|
| 0352092 | 1/1990 | European Pat. Off. . |
| 0443719 | 8/1991 | European Pat. Off. . |
| 3-23560 | 2/1991 | Japan . |
| 44398/91 | 2/1991 | Japan . |
| 3-41093 | 3/1991 | Japan . |
| 4-79078 | 5/1992 | Japan . |
| 2207678A | 2/1989 | United Kingdom . |
| 2212499A | 7/1989 | United Kingdom . |
| 9209620 | 6/1992 | WIPO . |

OTHER PUBLICATIONS

Recent Progress in Antifungal Chemotherapy, pp. 501–503, Marcel Dekker Inc., New York, 1992.
J. Chem. Soc., Chemical Communications, Issue 17, 1992 pp. 1231–1233.
Journal of Antibiotics, vol. 44, No. 9, pp. 925–933 (1991).
Journal of Antibiotics, vol. 44, No. 11, pp. 1187–1198 (1991).
Journal of Antibiotics, vol. 44, No. 9, pp. 919–924 (1991).
Chemistry Letters, Kurome et al., "Total Synthesis of Aureobasidin A, an Antifungal Cyclid Depsipeptide", vol. 11, pp. 1873–1876 (1993).

*Primary Examiner*—Jerry D. Johnson
*Attorney, Agent, or Firm*—Wenderoth, Lind & Ponack

[57] ABSTRACT

To provide a process for the total synthesis of a cyclic peptide, which is useful as antifungal drug, and novel compounds prepared by the synthesis method. A process for synthesizing a cyclic peptide represented by the following formula (I):

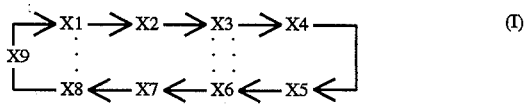

wherein
X1, X2, X4 and X7 are independently N-methyl-α-amino acid or α-hydroxy acid,
provided that at least one of X1, X2, X4 and X7 is a α-hydroxy acid;
X3, X6 and X8 are independently α-amino acid;
X5 is a cyclic amino acid;
X9 is a N-methyl-α-amino acid or α-hydroxy acid substituted by a hydroxy group;
and the dotted lines represent intramolecular hydrogen bonds;
which process comprises cyclizing a corresponding linear peptide between X5 and X6 via a peptide bond, and a novel compound represented by the formula (I).

1 Claim, No Drawings

CYCLIC PEPTIDES

This is a divisional application of Ser. No. 08/067,018, filed May 26, 1993, now abandoned.

BACKGROUND OF THE INVENTION

1. Field of the Invention

The present invention relates to a process for producing a cyclic peptide, which is useful as an antifungal drug, through total synthesis. Further, it relates to a novel cyclic peptide produced by the process.

2. Description of Related Art

There have been known more than 20 aureobasidins in addition to aureobasidin A (refer to Japanese Patent Laid-Open No. 138296/1990, No. 22995/1991, No. 44398/1991, No. 220199/1991 and No. 79078/1992). Each of these aureobasidins is a cyclic peptide composed of nine amino acids (or hydroxy acids), and has been produced as a fermentation product obtained by microbiological methods with the use of fungi, for example, *Aureobasidium pullulans* R106. Aureobasidins are highly useful as an antifungal drug having low toxicity and potent fungicidal activity on various pathogenic fungi. Aureobasidin A (SEQ ID No:1) has a chemical structure represented by the following formula (IV), which was determined with the use of physical and chemical analytical techniques (refer to J. Antibiotics, 44 (9), 925–933 (1991).

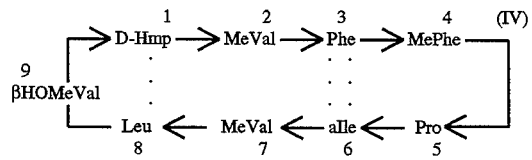

wherein D-Hmp represents 2(R)-hydroxy-3(R)-methylpentanoate residue.

Each of these compounds is produced either by a microbiological method or a semisynthetic method and, therefore, chemical modifications of these compounds are restricted. As a result, the development of aureobasidins are seriously restricted and, therefore, it has been urgently desired to complete a method for the total synthesis of aureobasidins. In the microbiological method, an aureobasidin is obtained together with well over ten congeners having similar structures. Thus it is necessary to separate a target aureobasidin therefrom. However, the separation is highly difficult and requires much labor, including the use of high performance liquid chromatography. Thus it has been urgently desired to establish a method for selectively synthesizing the target aureobasidin.

The first reason why the total synthesis of an aureobasidin has been impossible in the past resides in the complicated N-methylated structure involved in the aureobasidin molecule. The second reason resides in the final cyclization step. Regarding the first problem, there have been reported a number of coupling reactions for synthesizing peptides. However, most of coupling reactions of an N-methylated amino acid and another amino acid result in only a poor yield with frequent isomerization, which requires complicated separation procedures to isolate an target peptide. Therefore, the synthesis of a peptide containing N-methylated amino acids is almost impossible in practice. Among cyclic peptides containing N-methylated amino acids, a total synthesis of cyclosporin A consisting of 11 amino acids five of which are N-methylated has succeeded (refer to Japanese Patent Publication No. 23560/1991).

However every aureobasidin is entirely different from cyclosporin A in the amino acid composition. Namely, no amino acid but MeVal is common to both compounds. Further, the aureobasidin differs from cyclosporin A in the points that the aureobasidin is a cyclic depsipeptide having an ester bond in the molecule, and that some aureobasidins with high antifungal activity, such as aureobasidin A, contain βHOMeVal, which is a scarce amino acid in nature. Thus, as a matter of course, the method for synthesizing an aureobasidin differs from that for cyclosporin A in various points. Now the second problem as described above will be discussed. Supposing that a linear peptide of the aureobasidin might be obtained, it is unclear whether a cyclization would proceed so as to give the target aureobasidin. Even if cyclization occurs, there is a high possibility that a mixture of complicated compounds would result from isomerization. It is, therefore, impossible to suppose which amino acids (or a hydroxy acid) should be coupled by cyclization, namely which linear peptide should be synthesized and whether the linear peptide can be cyclized so as to give the target stereochemically pure aureobasidin or not. Although we actually attempted to synthesize aureobasidin A by cyclization reaction via an ester bond of the hydroxypeptide of the formula (V) (SEQ ID No:2, refer to Japanese Patent Laid-Open No. 41093/1991), which seemingly suffers from less isomerization, by various known methods, the target aureobasidin A could not be synthesized.

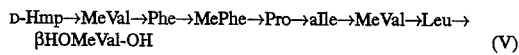

In the total synthesis of cyclosporin A described in the Japanese Patent Publication No. 23560/1991 cited above, they succeeded in cyclization for the first time when a certain linear undecapeptide was created and employed. More specifically, in the case of a cyclic peptide having a complicated stereochemical structure such as cyclosporin A, its linear peptide per se to be used as a raw material has a specific stereochemical structure by virtue of its peptide sequence. Therefore, when a linear peptide except for the above mentioned linear undecapeptide is used, there is no possibility that such a linear compound is folded into a necessary form so as to give a circular configuration wherein both ends are bonded to each other. In other methods for synthesizing various cyclosporin A derivatives (refer to British Patent Laid-Open No. 2212499A, U.S. Pat. No. 4,798,823 and British Patent Laid-Open No. 2207678A), in fact, their linear undecapeptides has been synthesized to cyclize at the same position as the one indicated in the above mentioned Japanese patent and cyclized.

SUMMARY OF THE INVENTION

It is necessary to create a linear peptide suitable for cyclization in the synthesis of an aureobasidin, which is a cyclic peptide having a complicated stereochemical structure, by cyclizing the linear peptide.

It is an object of the present invention to provide a process for the total synthesis of a cyclic peptide, which is useful as an antifungal drug, and novel compounds prepared by the synthesis method.

In summary, the first invention of the present application is related to a process for synthesizing a cyclic peptide represented by the following formula (I):

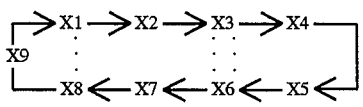  (I)

wherein

X1, X2, X4 and X7 are independently N-methyl-α-amino acid or α-hydroxy acid, provided that at least one of X1, X2, X4 and X7 is a α-hydroxy acid;

X3, X6 and X8 are independently α-amino acid;

X5 is a cyclic amino acid;

X9 is a substituted N-methyl-α-amino acid or α-hydroxy acid with a hydroxy group;

and the dotted lines represent intramolecular hydrogen bonds;

which process comprises cyclizing an O-protected or unprotected linear peptide having a sequence represented by the following formula (II) or a reactive derivative thereof:

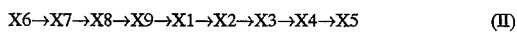

$$X6 \rightarrow X7 \rightarrow X8 \rightarrow X9 \rightarrow X1 \rightarrow X2 \rightarrow X3 \rightarrow X4 \rightarrow X5 \quad \text{(II)}$$

wherein

X1, X2, X3, X4, X5, X6, X7, X8 and X9 are as defined above.

The second invention of the present application is related to a cyclic peptide represented by the following formula (III):

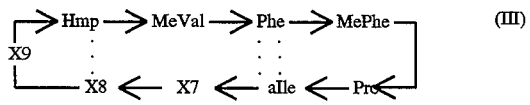  (III)

wherein

Hmp represents 2-hydroxy-3-methylpentanoate; (SEQ ID NO:54)

X7 is MeVal, MeLeu or MeaIle; X8 is Leu or aIle; and X9 is MeThr or βHOMeVal;

if X7 is MeVal, then X8 is aIle and X9 is βHOMeVal, or X8 is Leu and X9 is MeThr, if X7 is MeLeu or MeaIle, X8 is Leu and X9 is βHOMeVal;

and the dotted lines represent intramolecular hydrogen bonds.

In the present invention, the above-mentioned problems have been solved by appropriately selecting the position of cyclization. The present inventors have conducted extensive studies in order to establish a method for the total synthesis of an aureobasidin. As a result, we have found that the cyclization reaction in the final step requires the linear peptide of the formula (II) to form three intramolecular hydrogen bonds between the carbonyl group (CO) of X1 and the amino group (NH) of X8, between NH of X3 and CO of X6, and between CO of X3 and NH of X6 under the reaction condition, and that the C-terminal has to be a cyclic amino acid as shown in the formula (II) in order to prevent racemization and to retain the activity. Finally, we have found out that a linear peptide having the sequence of the chemical formula 2 can be efficiently converted into the cyclic peptide of the chemical formula 1 through cyclization. Namely, in the formulas (I) and (II), X3, X6 and X8 are independently α-amino acid; X1, X2, X4, X7 and X9 are independently N-methyl-α-amino acid or α-hydroxy acid; and X5 is a cyclic α-amino acid. Further, studies on structure-activity relationships of the cyclic peptides newly synthesized showed that X9 is a substituted N-methyl-α-amino acid or α-hydroxy acid with a hydroxy group, for example MeThr, cheaply available, instead of βHOMeVal which needs high cost for synthesis, thus completed the present invention. Each of X2, X3, X6 and X7 has to be an L-form α-amino acid, N-methyl-α-amino acid or α-hydroxy acid to retain antifungal activity.

Examples of the α-amino acid that can be used for the present invention include an aliphatic amino acid such as Val, Leu, Gly and Ala; an aromatic amino acid such as Phe, Tyr and Trp; a hydroxyamino acid such as Ser and Thr; an acidic amino acid such as Glu and Asp; an amide-amino acid such as Gln and Asn; a basic amino acid such as Lys, Arg and His; a sulfur-containing amino acid such as Met and Cys; and an imino acid such as Pro. Other examples of the α-amino acids that can be used for the present invention include aIle, Nva, Nle, Orn, 4Hyp, SPro, HONva, β-hydroxyphenylalanine, Hyl, oFPhe, pipecolic acid, an ester derivative of second carboxyl group of acidic amino acid, an alkyl or acyl derivative of hydroxyl group of hydroxyamino acid, HONva or β-hydroxyphenylalanine, and an acyl derivative of second amino group of basic amino acid. The carbon number of an ester derivative of carboxyl group is not limited, and benzyl (Bzl) group, C1–12 alkyl group such as methyl, ethyl, hexyl, octyl, isopropyl and cyclohexyl (cHex), or C1–C12 alkenyl group such as 3-hexenyl, is preferable. A cyclic peptide containing the α-amino acid ester derivative as a constituent can be obtained as an intermediate of a cyclic peptide composed of an acidic α-amino acid such as Glu and Asp as described below. Esterification can be carried out by a conventional method using a halogenated compound in the presence of a base. The carbon number of an alkyl or acyl derivative of a hydroxy group is not limited, and Bzl or C1–12 acyl group is preferable. A cyclic peptide containing the alkyl or acyl derivative of α-amino acid can be obtained as an intermediate of a cyclic peptide composed of a hydroxy-α-amino acid such as Ser and Thr as described below. Acylation can be carried out by a conventional method using an acid anhydride or an acyl halide in the presence of a base. Alkylation can be carried out by a conventional method using an alkyl halide in the presence of sodium hydride (NaH).

Val, Leu, aIle, Ile, Gly, Ala, Phe, Met etc. can be used for the present invention without protection. The second carboxyl group of an α-amino acid having a free carboxyl group at the side chain, such as Glu and Asp, or the hydroxy group of an α-amino acid having a hydroxy group, such as Ser and Thr, can be protected by Bzl, phenacyl (Pac), methyl and trimethylsilyl group by a reaction with bis(trimethylsilyl)trifluoroacetoamide (BSTFA), if needed. The second amino group of an α-amino acid having an amino group at the side chain, such as Lys and Arg, can be protected by a benzyloxycarbonyl (Z) or a tosyl (Tos) group. The protection groups can be removed by a known corresponding method to give the target cyclic peptide after completion of the cyclization reaction. The amide group of an amide-α-amino acid, such as Gln and Asn, can be protected by a methoxybenzhydryl (Mbh) group. The cyclic peptide containing an amide-α-amino acid can be prepared by reacting a cyclic peptide containing a corresponding acidic α-amino acid, such as Glu or Asp, with dicyclohexylcarbodiimide (DCC)/1-hydroxybenzotriazole (HOBt) etc. after conversion the free carboxyl group into an ammonium salt with ammonium carbonate etc. There are many known protective groups of hydroxy, carboxyl, amide group except for the above-described examples, and those protective groups can be used in the synthesis of a linear peptide (II) of the present invention.

Examples of the N-methyl-α-amino acid that can be used for the present invention include MeVal, MeaIle, MeLeu, MeGly, MeTyr, MeThr, MeSer, MePhe, βHOMePhe and HOMeNva. Also, an ester derivative of second carboxyl group, an acyl or alkyl derivative of hydroxyl group, or an acyl derivative of second amino group of α-amino acids described above, such as $R_6$ OMeNva where $R_6$ is benzyl, can be used in the present invention after N-methylation of their α-amino groups by the conventional method using methyl iodide ($CH_3I$)/NaH. Examples of the N-methyl-α-amino acid having a hydroxy group as a substituent that can be preferably used for the present invention include βHOMeVal, γHOMeVal, MeThr, MeSer and 3-hydroxy- or 4-hydroxy-N-methyl-α-amino acid. An N-methyl-α-amino acid having a carboxyl, hydroxy or amino group can be used after introduction of an appropriate protective group to the functional group if needed. The protective group can be removed by a known method corresponding to the protective group to obtain a target cyclic peptide after completion of the cyclization.

Examples of the α-hydroxy acid that can be used in the present invention include Hmp, Hmb, lactic acid, 2-hydroxypropionic acid, and an α-hydroxy acid which can be easily synthesized by a method using nitrous acid to convert an amino group into a hydroxy group via an azide derivative. Examples of the α-hydroxy acid having a second hydroxy group as a substituent that can be used in the present invention include 2,4-dihydroxy-3-methylpentanoic acid (Dhmp), 2-hydroxy-3-hydroxymethylpentanoic acid, 2,3-dihydroxy-3-methylbutanoic acid, and the derivatives thereof.

Examples of the cyclic α-amino acid that can be used in the present invention include Pro, 4Hyp, sPro, pipecolic acid, and the derivatives thereof.

A scheme to synthesize the linear peptide of the formula (II) in a good yield and in a stereochemically pure state will be presented below by taking aureobasidin A as an example. In the case of aureobasidin A, three peptides, i.e., aIle$^6$→MeVal$^7$ (fragment 1), Leu$^8$→βHOMeVal$^9$→D-Hmp$^1$ (fragment 2) and MeVal$^2$→Phe$^3$→MePhe$^4$→Pro$^5$ (fragment 3, SEQ ID No:3) are synthesized. Next, the fragments 2 and 3 are coupled to each other via a peptide bond between D-Hmp$^1$ and MeVal$^2$. Further, the fragments 2–3-coupled peptide thus obtained and the fragment 1 are coupled between MeVal$^7$ and Leu$^8$ to thereby give the linear depsipeptide of the following formula (VI) (SEQ ID No:4). Finally, the obtained linear depsipeptide is subjected to cyclization to thereby give the target compound of the formula (IV) (SEQ ID No:1).

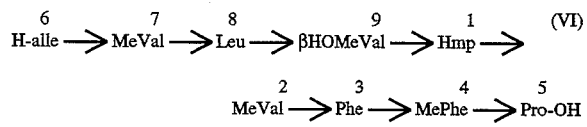

In order to efficiently obtain the target peptide in a stereochemically pure state, it is highly important to select suitable reagents and reaction conditions for each step of the synthesis.

Examples of the method for forming a peptide bond in each step include: (1) the activation of a carboxyl group with the use of a water-soluble carbodiimide and 1-hydroxybenzotriazole (HOBt), (2) the activation of a carboxyl group by converting into carboxazide with the use of diphenylphosphoryl azide (DPPA), and (3) the use of (benzotriazolyloxy)tris(dimethylamino)phosphonium hexafluorophosphate (BOP). A preferable example therefor, however, is (4) the use of bromo-tris-pyrrolidinophosphosium hexafluorophosphate (PyBroP) together with a base such as diisopropylethylamine (DIEA). The above-mentioned methods (1) to (3) have been commonly used for forming peptide bonds. However the formation of peptide bonds by these methods with the use of an N-methyl amino acid as an amine component often causes some problems, for example, a low yield and racemization. On the other hand, these problems can be solved and the target peptide can be obtained at a high yield by using the above method (4).

The ester bond between βHOMeVal$^9$ and D-Hmp$^1$ may be formed by, for example, (5) the use of PyBroP or (6) the use of a mixed anhydride with βHOMeVal by using 2,4,6-trichlorobenzoyl chloride. A preferable method therefor is (7) the use of DCC with a catalyst such as dimethylaminopyridine (DMAP) or 4-pyrrolidinopyridine so as to give the target compound at a high yield. The hydroxyl group of βHOMeVal$^9$ can be in a free state or protected.

The condensation of the fragments 2 and 3 via the peptide bond between D-Hmp$^1$ and MeVal$^2$ may be carried out by the above-mentioned methods (1) to (4). It is preferable to select the method (4) wherein PyBroP is used together with a base. Thus, the target fragments 2–3-coupled peptide, wherein the fragments 2 and 3 are coupled to each other, can be obtained in a good yield as a stereochemically pure product.

The condensation of the above-mentioned fragments 2–3-coupled peptide (Leu$^8$→βHOMeVal$^9$→D-Hmp$^1$→MeVal$^2$→Phe$^3$→MePhe$^4$→Pro$^5$; SEQ ID No:5) with the fragment 1 (aIle$^6$→MeVal$^7$) between Leu$^8$ and MeVal$^7$ may be carried out by, for example, using PyBroP with a base such as DIEA. It is preferable to activate the C-terminal carboxyl group with N-ethyl-N'-(dimethylaminopropyl)carbodiimide (EDC) and 3 hydroxy-4-oxo-3,4-dihydro-1,2,3-benzotriazine (HOObt). In order to obtain the target compound in a stereochemically pure state, it is important to control the reaction temperature. Namely, the reaction is usually carried out at from −20° to 30° C.

The final cyclization reaction can be completed as follows: the protective groups of the C-terminal and the N-terminal of the fragments 1–2–3-coupled peptide obtained by the steps described above are removed to give the peptide of the formula (VI), which is then converted into a peptide having an activated carboxyl group and a free amino group, and followed by reacting in the presence of a base. The reaction temperature for the cyclization may vary depending on the selected activated carboxyl group. In general, this reaction may be carried out within a temperature ranging from −20° to 30° C. The C-terminal may be activated by, for example, converting into N-hydroxysuccinimide ester (ONSu) or treating with PyBroP. Examples of the base include DIEA and pyridine.

A peptide activated by ONSu group may be obtained by reacting the linear peptide having a protected amino group at the N-terminal and a free carboxyl group at the C-terminal with a water soluble carbodiimide (for example, EDC) hydrochloride and N-hydroxysuccinimide (HONSu) in an organic solvent such as N,N-dimethylformamide (DMF) at a temperature from −10° to 30° C. Then the protective group at the N-terminal is removed by a corresponding reaction to give a compound wherein the amino group at the N-terminal is either in a free state or in a salt. Finally, the peptide of the formula (VI), wherein the C-terminal is ONSu-activated, is cyclized in the presence of a base.

A C-terminal activated compound by PyBroP may be obtained in the following manner. Namely, the peptide of the formula (VI), wherein the N-terminal is a free amino group or a salt thereof and the C-terminal is a free carboxyl group, is reacted with PyBroP in the presence of a base at a temperature, for example, from −10° to 30° C. in an organic solvent such as methylene chloride. The progress of this reaction is accompanied by cyclization.

In the cyclization step, either one of the two activation methods as described above may be employed to thereby give the target compound of the formula (IV). The yield of the product can be elevated by appropriately selecting the concentration of each reactant and the solvent and precisely controlling the reaction temperature in the reaction system.

In each of the above-mentioned steps, the N-terminal amino group may be protected with, for example, a t-butyloxycarbonyl (Boc) group, while the C-terminal carboxyl group may be protected with, for example, a Pac or Bzl group. These protective groups may be removed each by a known deblocking method, which may be optionally modified, corresponding to the protected compound to give first occurance objective product in first occurance free state or in the form of a salt, if needed. In addition to the examples of the protective groups cited above, there have been known a number of protective groups for an amino group and those for a carboxyl group. These protective groups are also usable for the present invention to synthesize the linear peptide of the formula (VI) and the cyclic peptide of the formula (IV). Further, the hydroxyl group of $\beta$HOMeVal$^9$ may be protected with a Bzl group, a methyl group or a trimethylsilyl group introduced therein by reacting with BSTFA. In the case when the compound thus protected is used, the cyclization would proceed in the same manner as in the case of the unprotected compound to give an O-protected compound of the formula (IV). After the completion of the cyclization, the obtained product may be deblocked by a known method corresponding to the protective group to give the compound of the formula (IV).

A cyclic peptide represented by the formula (I) described above can be prepared by the similar method with the compound of the formula (IV) cited above. Namely, the condensation by a peptide bond can be carried out by the methods (1)–(4) described above, and the method (4), wherein PyBroP is used with a base, is preferable to give a target compound shortly in a good yield and in a stereochemically pure state. The condensation by an ester bond can be performed by the method (5)–(7) cited above, and the method (7), wherein DCC is used with a catalyst such as DMAP or 4 pyrrolidinopyridine to give a target compound in a good yield. The cyclization reaction in the final step can be carried out by reacting so as to convert a linear peptide of the formula (II) into a compound having an activated carboxyl group as the C-terminal and a free amino group as the N-terminal in the presence of a base, as in the case of the synthesis of the compound of the formula (IV). A C-terminal can be activated by the method such as an activated ester method and a method using PyBroP, wherein second occurance base such as DIEA and pyridine can be used. Protection of a N-terminal, a C-terminal and a hydroxy group in each step can be carried out similarly with the case of the synthesis of the compound of the formula (IV).

The representative cyclic peptides obtained by the present invention are shown in Tables 1 and 2. Among these 18, 22, 23 and 24 are novel compounds and can be prepared by a fermentation method. More specifically, the compounds can be produced by a fermentation, wherein *Aureobasidium pullulans* No. R106 (FERM BP-1938), a producing organism of compound 1, and mediums, culture methods and purification methods described in the specifications of Japanese Patent Laid-Open No. 138296/1990, No. 22995/1991, No. 220199/1991 and No. 79078/1992 are used. For example, the above-mentioned producing organism is cultured in a liquid medium containing carbon sources such as glucose and glycerin, nitrogen sources such as peptone, ammonium salts and amino acids, inorganic salts, and others; then the cultured broth is extracted with an organic solvent such as ethanol; the extract is purified by an absorbent resin, and further by a reversed phase HPLC using a solvent mixture of 60–70% acetonitrile/water, and by a silica gel HPLC using a solvent mixture of hexane/acetonitrile/2-propanol to separate and obtain compound 1 and compounds 18, 22, 23 and 24. Compounds 26–39 are novel compounds which are prepared by the present invention. Compound 38 showed higher activity against *Candida albicans* TIMM 0171 than compound 1.

Physico-chemical properties of the representative compounds of Tables 1 and 2 prepared by the present invention are shown in Tables 3–5, and their antifungal activities are shown in Tables 6–9.

The antifungal activity is measured by the agar dilution method using Casitone agar medium (glucose 2.0%, Bacto-casitone 0.9%, yeast extract 1.0%, agar 2.0%, concentrations are all w/v) for compounds 2, 3, 4, 7, 9–13 and 15, and Sabouraud-dextrose agar medium (glucose 2.0%, polypeptone 1.0%, agar 1.5%, concentrations are all w/v) for other compounds. The minimum inhibitory concentration (MIC) values were determined after incubation at 30° C. for 2 days. Compound 18, a Hmp stereoisomer of compound 1, showed high activity. Compound 19 having L-MeThr at X9 had high antifungal activity. This compound can be synthesized at a lower cost than the aureobasidins having $\beta$HOMeVal, and therefore is superior to the aureobasidins judging from their costs. Compounds 22 and 23 were active as much as compound 1 having the highest activity among the known aureobasidins. Further, compound 24 were more active than compound 1. Compounds 1–39 showed no toxicity signs when they were independently given intraperitoneally to mice at the dose of 100 mg/kg.

Abbreviations for the $\alpha$-amino acids, N-methyl-$\alpha$-amino acids or $\alpha$-hydroxy acid, are shown as follows.

| | |
|---|---|
| D-Hmp | 2(R)-hydroxy-3(R)-methylpentanoic acid |
| (2R,3S)-Hmp | 2(R)-hydroxy-3(S)-methylpentanoic acid |
| D-Hmb | 2(R)-hydroxy-3-methylbutanoic acid |
| L-Hmb | 2(S)-hydroxy-3-methylbutanoic acid |
| Dhmp | 2,4-dihydroxy-3(R)-methylpentanoic acid |
| MeaIle | N-methylalloisoleucine |
| MeLeu | N-methylleucine |
| MePhe | N-methylphenylalanine |
| $\beta$HOMePhe | $\beta$-hydroxy-N-methylphenylalanine |
| $\beta$ROMePhe | $\beta$-acyloxy-N-methylphenylalanine |
| oFPhe | o-fluorophenylalanine |
| oFMePhe | o-fluoro-N-methylphenylalanine |
| $\beta$HOMeVal | $\beta$-hydroxyl-N-methylvaline |
| $\gamma$HOMeVal | $\gamma$-hydroxyl-N-methylvaline |
| SPro | thioproline |
| MeThr | N-methylthreonine |
| GluOR | glutamic acid $\gamma$-alkyl ester, $\gamma$-alkenyl ester or $\gamma$-benzyl ester |
| HONva | 5-hydroxynorvaline |
| RONva | 5-acyloxynorvaline or 5-benzyloxynorvaline |
| HOMeNva | 5-hydroxy-N-methylnorvaline |
| ROMeNva | 5-acyloxy-N-methylnor-valine or 5-benzyloxy-N-methylnorvaline |
| MeTyr | N-methyltyrosine |
| MeSer | N-methylserine |

TABLE 1

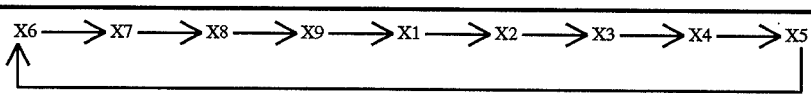

| Compound No. | X1 | X2 | X3 | X4 | X5 | X6 | X7 | X8 | X9 |
|---|---|---|---|---|---|---|---|---|---|
| 1 | D-Hmp | L-MeVal | L-Phe | L-MePhe | L-Pro | L-aIle | L-MeVal | L-Leu | L-βHOMeVal |
| 2 | D-Hmp | • | • | • | • | • | • | • | • |
| 3 | • | • | • | • | • | • | L-Val | • | • |
| 4 | • | • | • | • | • | • | • | • | L-γHOMeVal |
| 5 | • | • | • | L-βHOMePhe | • | • | • | • | • |
| 6 | • | • | • | • | • | L-Leu | • | • | • |
| 7 | • | • | L-oFPhe | L-oFMePhe | • | • | • | • | • |
| 8 | • | • | • | L-MeTyr | • | • | • | • | • |
| 9 | • | • | • | • | L-4Hyp | • | • | • | • |
| 10 | • | • | • | • | L-SPro | • | • | • | • |
| 11 | • | • | • | • | • | • | L-Nle | • | • |
| 12 | • | • | • | • | • | • | • | L-Nva | • |
| 13 | • | • | • | L-MeGly | • | • | • | • | • |
| 14 | • | • | • | L-βROMePhe R: CO(CH$_2$)$_3$COOH | • | • | • | • | • |
| 15 | • | • | • | L-βROMePhe R: COCH$_3$ | • | • | • | • | • |
| 16 | • | • | • | L-βROMePhe R: CO(CH$_2$)$_2$NHCOCH$_3$ | • | • | • | • | • |
| 17 | Dhmp | • | • | • | • | • | • | • | • |
| 18 | (2R,3S)-Hmp | • | • | • | • | • | • | • | • |
| 19 | • | • | • | • | • | • | • | • | L-MeThr |

The dots (•) in Tables 1 and 2 show identity with the amino acids or the hydroxy acid of compound 1.

TABLE 1

| Compound No. | X1 | X2 | X3 | X4 | X5 | X6 | X7 | X8 | X9 |
|---|---|---|---|---|---|---|---|---|---|
| 20 | • | • | • | • | • | • | • | • | D-βHOMeVal |
| 21 | • | • | • | • | D-Pro | • | • | • | • |
| 22 | • | • | • | • | • | • | L-MeaIle | • | • |
| 23 | • | • | • | • | • | • | L-MeLeu | • | • |
| 24 | • | • | • | • | • | • | • | L-aIle | • |
| 25 | D-Hmb | • | • | • | • | L-Val | • | • | • |
| 26 | • | • | • | • | • | L-GluOr R: Bzl | • | • | • |
| 27 | • | • | • | • | • | • | L-ROMeNva R: Bzl | • | • |
| 28 | • | • | • | • | • | • | L-HOMeNVa | • | • |
| 29 | • | • | • | • | • | • | L-Hmb | • | • |
| 30 | • | • | • | • | • | L-GluOR R: n-butyl | • | • | • |
| 31 | • | • | • | • | • | L-GluOR R: n-hexyl | • | • | • |
| 32 | • | • | • | • | • | L-GluOR R: n-octyl | • | • | • |
| 33 | • | • | • | • | • | L-GluOR R: n-decyl | • | • | • |
| 34 | • | • | • | • | • | L-GluOR R: n-cis-3-hexenyl | • | • | • |
| 35 | • | • | • | • | • | L-GluOR R: n-trans-3-hexenyl | • | • | • |
| 36 | • | • | • | • | • | L-HONva | • | • | • |
| 37 | • | • | • | • | • | L-RONva R: n-hexanoyl | • | • | • |
| 38 | • | • | • | • | • | • | • | L-GluOR R: cHex | • |
| 39 | • | • | • | • | • | • | • | L-HONva | • |

TABLE 3

| Compound No. | Molecular formula | Elemental analysis (%) | | | | | | FAB-MS | *Amino acid analysis |
|---|---|---|---|---|---|---|---|---|---|
| | | Found | | | Calcd | | | | |
| | | C | H | N | C | H | N | | |
| Aureobasdidin A (1) | $C_{60}H_{92}N_8O_{11}$ | 65.0 | 8.5 | 9.9 | 65.43 | 8.42 | 10.17 | 1101 (M+H), 1123 (M+Na) | Pro, aIle, Leu, Phe |
| 2 | $C_{59}H_{90}N_8O_{11}$ | 64.81 | 8.53 | 10.06 | 65.17 | 8.34 | 10.30 | 1087 (M+H), 1109 (M+Na) | Pro, aIle, Leu, Phe |
| 3 | $C_{59}H_{90}N_8O_{11}$ | 65.09 | 8.61 | 9.96 | 65.17 | 8.34 | 10.30 | 1087 (M+H), 1109 (M+Na) | Pro, Val, Leu, Phe |
| 4 | $C_{60}H_{92}N_8O_{11}$ | 65.12 | 8.71 | 9.87 | 65.43 | 8.42 | 10.17 | 1101 (M+H), 1123 (M+Na) | Pro, aIle, Leu, Phe |
| 5 | $C_{60}H_{92}N_8O_{11}$ | 64.36 | 8.51 | 9.83 | 64.49 | 8.30 | 10.03 | 1117 (M+H), 1139 (M+Na) | Pro, aIle, Leu, Phe |
| 6 | $C_{60}H_{92}N_8O_{11}$ | 65.21 | 8.58 | 10.00 | 65.43 | 8.42 | 10.17 | 1101 (M+H), 1123 (M+Na) | Pro, Leu, Phe |
| 7 | $C_{60}H_{90}N_8O_{11}F_2$ | 63.01 | 8.16 | 9.41 | 63.36 | 7.98 | 9.85 | 1137 (M+H), 1159 (M+Na) | Pro, aIle, Leu, oFPhe |
| 8 | $C_{60}H_{92}N_8O_{12}$ | 63.81 | 8.32 | 9.80 | 64.49 | 8.30 | 10.03 | 1117 (M+H), 1139 (M+Na) | Pro, aIle, Leu, Phe |
| 9 | $C_{60}H_{92}N_8O_{12}$ | 63.92 | 8.50 | 9.86 | 64.49 | 8.30 | 10.03 | 1117 (M+H), 1139 (M+Na) | 4Hyp, aIle, Leu, Phe |
| 10 | $C_{59}H_{90}N_8O_{11}S$ | 62.91 | 8.26 | 9.63 | 63.30 | 8.04 | 10.00 | 1119 (M+H), 1141 (M+Na) | SPro, aIle, Leu, Phe |
| 11 | $C_{60}H_{92}N_8O_{11}$ | 65.13 | 8.72 | 9.75 | 65.43 | 8.42 | 10.17 | 1101 (M+H), 1123 (M+Na) | Pro, Leu, Nle, Phe |
| 12 | $C_{59}H_{90}N_8O_{11}$ | 64.76 | 8.79 | 9.80 | 65.17 | 8.34 | 10.30 | 1087 (M+H), 1109 (M+Na) | Pro, aIle, Nva, Phe |
| 13 | $C_{53}H_{86}N_8O_{11}$ | 62.30 | 8.81 | 10.38 | 62.95 | 8.57 | 11.08 | 1011 (M+H), 1033 (M+Na) | MeGly, Pro, aIle, Leu, Phe |
| 14 | $C_{65}H_{98}N_8O_{15}$ | 62.58 | 7.96 | 8.80 | 63.39 | 8.02 | 9.10 | 1231 (M+H), 1253 (M+Na) | Pro, aIle, Leu, Phe |
| 15 | $C_{62}H_{94}N_8O_{13}$ | 64.04 | 8.32 | 9.48 | 64.23 | 8.17 | 9.66 | 1159 (M+H), 1181 (M+Na) | Pro, aIle, Leu, Phe |

TABLE 4

| Compound No. | Molecular formula | Elemental analysis (%) | | | | | | FAB-MS | *Amino acid analysis |
|---|---|---|---|---|---|---|---|---|---|
| | | Found | | | Calcd | | | | |
| | | C | H | N | C | H | N | | |
| 16 | $C_{65}H_{99}N_9O_{14}$ | 62.58 | 8.23 | 9.96 | 63.44 | 8.11 | 10.24 | 1230 (M+H), 1252 (M+Na) | Pro, aIle, Leu, Phe, bAla |
| 17 | $C_{60}H_{92}N_8O_{12}$ | 63.81 | 9.03 | 9.74 | 64.49 | 8.30 | 10.03 | 1117 (M+H), 1139 (M+Na) | Pro, aIle, Leu, Phe |
| 18 | $C_{60}H_{92}N_8O_{11}$ | 64.48 | 8.29 | 9.85 | 65.43 | 8.42 | 10.17 | 1101 (M+H), 1123 (M+Na) | Pro, aIle, Leu, Phe |
| 19 | $C_{59}H_{90}N_8O_{11}$ | 63.89 | 8.18 | 9.87 | 65.17 | 8.34 | 10.30 | 1087 (M+H), 1109 (M+Na) | Pro, aIle, Leu, Phe |
| 20 | $C_{60}H_{92}N_8O_{11}$ | 64.29 | 8.61 | 9.81 | 65.43 | 8.42 | 10.17 | 1101 (M+H), 1123 (M+Na) | Pro, aIle, Leu, Phe |
| 21 | $C_{60}H_{92}N_8O_{11}$ | 64.62 | 8.39 | 9.91 | 65.43 | 8.42 | 10.17 | 1101 (M+H), 1123 (M+Na) | aIle, Leu, Phe, D-Pro |
| 22 | $C_{61}H_{94}N_8O_{11}$ | 64.12 | 8.42 | 9.48 | 65.68 | 8.49 | 10.05 | 1115 (M+H), 1137 (M+Na) | Pro, aIle, Leu, Phe |
| 23 | $C_{61}H_{94}N_8O_{11}$ | 64.81 | 8.63 | 9.60 | 65.68 | 8.49 | 10.05 | 1115 (M+H), 1137 (M+Na) | Pro, aIle, Leu, Phe |
| 24 | $C_{60}H_{92}N_8O_{11}$ | 64.53 | 8.64 | 9.52 | 65.43 | 8.42 | 10.17 | 1101 (M+H), 1123 (M+Na) | Pro, aIle, Phe |
| 25 | $C_{58}H_{88}N_8O_{11}$ | 63.92 | 8.25 | 10.11 | 64.90 | 8.26 | 10.43 | 1073 (M+H), 1095 (M+Na) | Pro, Val, Leu, Phe |
| 26 | $C_{66}H_{94}N_8O_{13}$ | 64.46 | 8.10 | 9.84 | 65.65 | 7.85 | 9.28 | 1207 (M+H), 1229 (M+Na) | Pro, Glu, Leu, Phe |
| 27 | $C_{67}H_{98}N_8O_{12}$ | 65.73 | 8.31 | 9.24 | 66.64 | 8.18 | 9.28 | 1207 (M+H), 1229 (M+Na) | Pro, aIle, Leu, Phe |
| 28 | $C_{60}H_{92}N_8O_{12}$ | 63.63 | 8.49 | 9.78 | 64.49 | 8.30 | 10.03 | 1117 (M+H), 1139 (M+Na) | Pro, aIle, Leu, Phe |
| 29 | $C_{59}H_{89}N_7O_{12}$ | 64.09 | 8.20 | 8.73 | 65.11 | 8.24 | 9.01 | 1088 (M+H), 1110 (M+Na) | Pro, aIle, Leu, Phe |

TABLE 5

| Compound No. | Molecular formula | Elemental analysis (%) | | | | | | FAB-MS | *Amino acid analysis |
|---|---|---|---|---|---|---|---|---|---|
| | | Found | | | Calcd | | | | |
| | | C | H | N | C | H | N | | |
| 30 | $C_{63}H_{96}N_8O_{13}$ | 64.61 | 8.36 | 9.48 | 64.48 | 8.25 | 9.55 | 1173 (M+H), 1195 (M+Na) | Glu, Pro, Leu, Phe |
| 31 | $C_{65}H_{100}N_8O_{13}$ | 64.18 | 8.30 | 9.12 | 64.98 | 8.39 | 9.33 | 1201 (M+H), 1223 (M+Na) | Glu, Pro, Leu, Phe |
| 32 | $C_{67}H_{104}N_8O_{13}$ | 64.89 | 8.82 | 9.03 | 65.45 | 8.53 | 9.11 | 1229 (M+Hf, 1251 (M+Na) | Glu, Pro, Leu, Phe |
| 33 | $C_{69}H_{108}N_8O_{13}$ | 65.33 | 8.47 | 8.38 | 65.90 | 8.66 | 8.91 | 1257 (M+H). 1279 (M+Na) | Glu, Pro, Leu, Phe |
| 34 | $C_{65}H_{98}N_8O_{13}$ | 64.96 | 8.14 | 9.00 | 65.08 | 8.23 | 9.34 | 1199 (M+H), 1221 (M+Na) | Glu. Pro, Leu, Phe |
| 35 | $C_{65}H_{98}N_8O_{13}$ | 64.59 | 8.03 | 8.95 | 65.08 | 8.23 | 9.34 | 1199 (M+H), 1221 (M+Na) | Glu, Pro, Leu, Phe |
| 36 | $C_{59}H_{90}N_8O_{12}$ | 63.89 | 8.07 | 10.09 | 64.22 | 8.22 | 10.16 | 1103 (M+H), 1125 (M+Na) | Pro, Leu, Phe |
| 37 | $C_{65}H_{100}N_8O_{13}$ | 64.71 | 8.09 | 9.02 | 64.98 | 8.39 | 9.33 | 1201 (M+H), 1223 (M+Na) | Pro, Leu, Phe |
| 38 | $C_{65}H_{98}N_8O_{13}$ | 65.17 | 8.11 | 9.08 | 65.08 | 8.23 | 9.34 | 1199 (M+H), 1221 (M+Na) | Glu, Pro, aIle, Phe |
| 39 | $C_{59}H_{90}N_8O_{12}$ | 64.01 | 8.04 | 9.93 | 64.22 | 8.22 | 10.16 | 1103 (M+H), 1125 (M+Na) | Pro, aIle, Phe |

*Amino acid analyses shown in the Tables 3 to 5 were carried out by JCL-300 manufactured by JEOL Co., Ltd. and detected by ninhydrin reaction.

TABLE 6

| Test organisms | | MIC (μg/ml) Compound No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Candida albicans | TIMM 0136 | 0.025 | 0.10 | 0.10 | 0.20 | 0.025 | 0.025 | 0.10 | 0.39 | 0.05 | 0.05 | 0.20 | 0.05 |
| C. albicans | TIMM 0171 | 0.025 | 0.10 | 0.10 | 0.10 | 0.025 | 0.10 | 0.10 | 0.39 | 0.05 | 0.05 | 0.20 | 0.10 |
| C. kefyr | TIMM 0301 | 0.39 | 0.20 | 0.20 | 0.78 | 0.78 | 0.78 | 0.20 | 0.78 | 0.20 | 0.20 | 1.56 | 0.20 |
| C. grabrata | TIMM 1062 | 0.20 | 0.20 | 0.20 | 1.56 | 0.20 | 0.78 | 0.20 | 1.56 | 0.20 | 0.39 | 0.78 | 0.20 |
| Cryptococcus neoformans | TIMM 0354 | 0.78 | 1.56 | 1.56 | 25 | 3.12 | 12.5 | >25 | >25 | 3.12 | 6.25 | >25 | 6.25 |

TABLE 7

| Test organisms | | MIC (μg/ml) Compound No. | | | | | | | | | | |
|---|---|---|---|---|---|---|---|---|---|---|---|---|
| | | 13 | 14 | 15 | 16 | 17 | 18 | 19 | 20 | 21 | 22 | 23 |
| Candida albicans | TIMM 0136 | 0.10 | 1.56 | 0.10 | 0.20 | 0.10 | 0.012 | 0.10 | 0.39 | 0.10 | 0.10 | 0.10 |
| C. albicans | TIMM 0171 | 0.05 | 1.56 | 0.10 | 0.20 | 0.10 | 0.012 | 0.10 | 0.39 | 0.39 | 0.20 | 0.20 |
| C. kefyr | TIMM 0301 | 0.10 | 3.12 | 0.39 | 0.39 | 0.39 | 0.39 | 0.39 | >25 | 0.78 | 1.56 | 0.78 |
| C. grabrata | TIMM 1062 | 0.78 | 12.5 | 0.10 | 1.56 | 0.78 | 0.20 | 0.78 | 1.56 | 1.56 | 0.78 | 0.78 |
| Cryptococcus neoformans | TIMM 0354 | 12.5 | >25 | 3.12 | >25 | 3.12 | 1.56 | >25 | >25 | 1.56 | 1.56 | 1.56 |

TABLE 8

| Test organism | | MIC (μg/ml) Compound No. | | | | | |
|---|---|---|---|---|---|---|---|
| | | 24 | 25 | 26 | 27 | 28 | 29 |
| Candida albicans | TIMM 0136 | 0.006 | 0.025 | 0.20 | 0.78 | 0.78 | 0.39 |
| C. albicans | TIMM 0171 | 0.006 | 0.05 | 0.10 | 0.78 | 0.78 | 0.39 |
| C. kefyr | TIMM 0301 | 0.10 | 0.39 | 1.56 | 3.12 | 1.56 | 0.39 |
| C. grabrata | TIMM 1062 | 0.05 | 0.78 | 0.39 | >25 | 1.56 | 1.56 |
| Crytococcus neoformans | TIMM 0354 | 0.78 | 6.25 | >25 | >25 | 12.5 | >25 |

TABLE 9

| Test organism | | MIC (μg/ml) Compound No. | | | | | | | | | |
|---|---|---|---|---|---|---|---|---|---|---|---|
| | | 30 | 31 | 32 | 33 | 34 | 35 | 36 | 37 | 38 | 39 |
| Candida albicans | TIMM 0136 | 0.39 | 0.39 | 0.78 | 1.56 | 0.20 | 0.20 | 6.25 | 0.10 | 0.20 | 3.12 |
| C. albicans | TIMM 0171 | 0.39 | 0.20 | 0.78 | 1.56 | 0.10 | 0.78 | 3.12 | 0.10 | 0.013 | 3.12 |
| C. kefyr | TIMM 0301 | 1.56 | 3.12 | 6.25 | >25 | 0.78 | 1.56 | 6.25 | 0.78 | 3.12 | 1.56 |
| C. grabrata | TIMM 1062 | 3.12 | 1.56 | 1.56 | >25 | 0.39 | 0.39 | >25 | 0.39 | 1.56 | 12.5 |
| Crytococcus neoformans | TIMM 0354 | >25 | >25 | >25 | >25 | >25 | >25 | >25 | 12.5 | >25 | >25 |

EXAMPLES

To further illustrate the present invention in greater detail, and not by way of limitation, the following Examples will be given.

EXAMPLE 1

Synthesis of cyclo(L-aIle-L-MeVal-L-Leu-L-βHOMeVal-D-Hmp-L-MeVal-L-Phe-L-MePhe-L-Pro) (compound 1)

a) Boc-L-Pro-OPac

To a solution of Boc-L-Pro-OH (1.08 g, 5.00 mmol) in acetone (10 ml) were added triethylamine (0.76 ml, 5.50 mmol) and phenacyl bromide (1.09 g, 5.50 mmol) under ice-cooling. After stirring for 5 minutes, the mixture was further stirred at room temperature for 4 hours. Then it was concentrated under reduced pressure and ethyl acetate was added. The resulting mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was dissolved in hexane to produce crystals and the crystals were washed with cold hexane to thereby give the title compound. Yield: 1.54 g (92.2%).

b) HCl•H-L-Pro-OPac

To Boc-L-Pro-OPac (12.71 g, 38.12 mmol) was added a 5.5N hydrogen chloride/dioxane solution (138.6 ml) and the mixture was allowed to stand at room temperature for 2 hours. Then ethyl ether was added thereto. After ice-cooling for 30 minutes, crystals thus precipitated were collected by filtration and washed with cold ethyl ether. Thus the title compound was obtained. Yield: 10.25 g (99.6%).

c) Boc-L-MePhe-L-Pro-OPac

To a solution of Boc-L-MePhe-OH (1.00 g, 3.58 mmol) and HCl•H-L-Pro-OPac (643.7 mg, 2.39 mmol) in dichloromethane (3.58 ml) were added PyBroP (1.67 g, 3.58 mmol) and DIEA (1.67 ml, 9.56 mmol) under ice-cooling. After stirring for 2 hours under ice-cooling, the mixture was further stirred at room temperature for 1 hour. Then it was concentrated under reduced pressure and ethyl acetate was added thereto. The resulting mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified by medium-pressure silica gel column chromatography (silica gel: 70 g, eluted with a toluene/ethyl acetate mixture 7:1). The eluate was further concentrated under reduced pressure. Then the concentrate was dissolved in hexane to produce crystals and the crystals were washed with cold hexane to thereby give the title compound. Yield: 951 mg (82.6%).

d) HCl•H-L-MePhe-L-Pro-OPac

To Boc-L-MePhe-L-Pro-OPac (12.3 g, 25.7 mmol) was added a 5.5N hydrogen chloride/dioxane solution (140 ml) and the mixture was allowed to stand at room temperature for 1 hour. After concentration under reduced pressure, the residue was dissolved in ethyl ether to produce crystals and the crystals were washed with ethyl ether. Thus the title compound was obtained. Yield: 11.2 g (100%).

e) Boc-L-Phe-L-MePhe-L-Pro-OPac

To a solution of Boc-L-Phe-OH (424 mg, 1.60 mmol) in dichloromethane (2.9 ml) were added, under ice-cooling, HCl•H-L-MePhe-L-Pro-OPac (600 mg, 1.39 mmol) and PyBroP (745 mg, 1.60 mmol), and further DIEA (921 µl, 1, 5.29 mmol) was added thereto dropwise within 20 minutes. After stirring for 1.5 hours under ice-cooling, the mixture was further stirred at room temperature for 2 hours. Then it was concentrated under reduced pressure and ethyl acetate was added thereto. The resulting mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified by medium-pressure silica gel column chromatography (silica gel: 40 g, eluted with a toluene/ethyl acetate mixture 3:1). The eluate was further concentrated under reduced pressure. Then the concentrate was dissolved in hexane to produce crystals and the crystals were washed with cold hexane. Thus the title compound was obtained. Yield: 767 mg (85.9%).

f) HCl•H-L-Phe-L-MePhe-L-Pro-OPac

To Boc-L-Phe-L-MePhe-L-Pro-OPac (10.8 g, 16.8 mmol) was added a 5.5N hydrogen chloride/dioxane solution (122 ml), and the mixture was allowed to stand at room temperature for 1.5 hours. After concentration under reduced pressure, the residue was dissolved in ethyl ether to produce crystals and the crystals were washed with ethyl ether. Thus the title compound was obtained. Yield: 8.91 g (91.8%).

g) Boc-L-MeVal-L-Phe-L-MePhe-L-Pro-OPac

To a solution of Boc-L-MeVal-OH (192 mg, 0.83 mmol) in dichloromethane (1.6 ml) were added, under ice-cooling, HCl•H-L-Phe-L-MePhe-L-Pro-OPac (400 mg, 0.69 mmol) and PyBroP (387 mg, 0.83 mmol), and further DIEA (500 µl, 2.87 mmol) was added thereto. After stirring for 2 hours under ice-cooling, the mixture was further stirred at room temperature for 4 hours. Then it was concentrated under reduced pressure and ethyl acetate was added thereto. The resulting mixture was successively washed with a 10% aqueous solution of citric acid, a saturated aqueous solution of sodium chloride, a saturated aqueous solution of sodium hydrogencarbonate and a saturated aqueous solution of sodium chloride. The organic layer was dried over magnesium sulfate and concentrated under reduced pressure. The residue obtained was purified by medium-pressure silica gel column chromatography (silica gel: 40 g, eluted with a toluene/ethyl acetate mixture 3:1). Thus the title compound having the structure of SEQ ID No. 6 was obtained. Yield: 450 mg (86.1%).

h) HCl•H-L-MeVal-L-Phe-L-MePhe-L-Pro-OPac

To Boc-L-MeVal-L-Phe-L-MePhe-L-Pro-OPac (SEQ ID No. 6) (1.08 g, 1.43 mmol) first occurance was added a 5.5N hydrogen chloride/dioxane solution (13.0 ml) and the mixture was allowed to stand at room temperature. After concentration under reduced pressure, the residue was dissolved in ethyl ether to produce crystals and the crystals were washed with ethyl ether. Thus the title compound having the structure of SEQ ID No. 7 was obtained. Yield: 922 mg. (93.0%).

i) Boc-DL-βHOMeVal-OBzl

To a suspension of H-DL-βHOMeVal-OH (38.6 mg, 0.264 mmol) in DMF (0.57 ml) was added BSTFA (0.56 ml, 2.11 mmol) under ice-cooling and the obtained mixture was stirred at room temperature for 1 hour. Next, di-t-butyl dicarbonate (72.8 µl, 0.317 mmol) was added thereto under ice-cooling and the mixture was stirred at room temperature for 1.5 hours. The mixture was concentrated under reduced pressure, and a 10% aqueous solution of citric acid was added thereto. Then the resulting mixture was washed with a saturated aqueous solution of sodium chloride. The ethyl acetate layer was dried over magnesium sulfate and concentrated under reduced pressure. The oily residue thus obtained was dissolved in ethyl acetate (0.5 ml), and triethylamine (55.0 µl, 0.396 mmol) and benzyl bromide (62.8 µl, 0.528 mmol) were added thereto under ice-cooling. Then the mixture was stirred under ice-cooling for 5 minutes and then at room temperature for 48 hours. After concentration under reduced pressure, the concentrate was purified by preparative silica gel thin-layer chromatography (developed with a chloroform/methanol mixture 19:1) to thereby give the title compound. Yield 60.7 mg (68.1%).

j) HCl•H-DL-βHOMeVal-OBzl

To Boc-DL-βHOMeVal-OBzl (472 mg, 1.40 mmol) was added a 5.5N hydrogen chloride/dioxane solution (29.5 ml) and the mixture was allowed to stand at room temperature for 1.5 hours. After concentration under reduced pressure, the residue was dissolved in ethyl ether to produce crystals and the crystals were washed with ethyl ether. Thus the title compound was obtained. Yield: 367 mg. (95.7%).

k) Boc-L-Leu-DL-βHOMeVal-OBzl

To a solution of Boc-L-Leu-OH•H₂O (1.34 g, 5.39 mmol) in dichloromethane (10 ml) were added, under ice-cooling, HCl•H-DL-βHOMeVal-OBzl (981.1 mg, 3.59 mmol) and PyBroP (2.52 g, 5.39 mmol), and further DIEA (2.50 ml, 14.4 mmol) was added thereto. After stirring for 1 hour under ice-cooling, the mixture was further stirred at room temperature for 8 hours. Then it was concentrated under reduced pressure and ethyl acetate was added thereto. The resulting mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified by medium-pressure silica gel column chromatography (silica gel: 40 g, eluted with a toluene/ethyl acetate mixture 3:1). Further, the eluate was dissolved in hexane to produce crystals and the crystals were washed with hexane. Thus the title compound was obtained. Yield: 1.05 g (65.2%).

l) Boc-L-Leu-DL-βHOMeVal-OH

To a solution of Boc-L-Leu-DL-βHOMeVal-OBzl (43.5 mg, 96.5 mmol) in methanol (40 ml) was added palladium black (40 mg). Then hydrogen gas was blown into the obtained mixture at room temperature for 50 minutes. After removal of the catalyst by filtration, the filtrate was concentrated under reduced pressure to thereby give the title compound. Yield: 30.6 mg (87.9%).

m) Boc-L-Leu-L-βHOMeVal-D-Hmp-OPac

Boc-L-Leu-DL-βHOMeVal-OH (744 mg, 2.15 mmol), phenacyl (2R)-hydroxy-(3R)-methylpentanoate (H-D-Hmp-OPac) (589 mg, 2.36 mmol) and 4-pyrrolidinopyridine (95.6 mg, 0.65 mmol) were dissolved in tetrahydrofuran (THF) (4.3 ml) and dicyclohexylcarbodiimide (DCC) (487 mg, 2.36 mmol) was added thereto under ice-cooling. The obtained mixture was stirred under ice-cooling for 1 hour, slowly returned to room temperature, and stirred for additional 18 hours. After concentration under reduced pressure, ethyl acetate was added thereto and the insoluble material was filtered off. The filtrate was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified by medium-pressure silica gel column chromatography (silica gel: 80 g, eluted with a toluene/ethyl acetate mixture 5:1) to thereby give Boc-L-Leu-DL-βHOMeVal-L-Hmp-OPac. Yield: 1.00 g (78.7%). Further, diastereomers were separated from each other by medium-pressure silica gel column chromatography (silica gel: 200 g, eluted with toluene/ethyl acetate mixtures 15:1 and 10:1) to thereby give the title compound. Yield: 357 mg (56.2 %, based on the L—L compound contained in Boc-L-Leu-DL-βHOMeVal-OH as the starting material).

n) Boc-L-Leu-L-βHOMeVal-D-Hmp-OH

Boc-L-Leu-L-βHOMeVal-D-Hmp-OPac (220 mg, 0.37 mmol) was dissolved in a 90% aqueous solution of acetic acid (18.5 ml). Then zinc dust (3.60 g, 55.5 mmol) was added thereto under ice-cooling while ultrasonically stirring. The mixture was ultrasonically stirred under ice-cooling for 7.5 hours. After removal of insoluble materials by filtration, the filtrate was concentrated under reduced pressure. Then a 10% aqueous solution of citric acid was added thereto and the mixture was extracted with ethyl acetate. The extract was washed with a saturated aqueous solution of sodium chloride, dried over magnesium sulfate and concentrated under reduced pressure. The residue thus obtained was purified by medium-pressure silica gel column chromatography (silica gel: 10 g, eluted with a chloroform/methanol/acetic acid mixture 50:1:0.5) to thereby give the title compound. Yield: 133 mg (73.7%).

o) HCl•H-L-MeVal-OPac

To a solution of Boc-L-MeVal-OH (4.94 g, 21.4 mmol) in acetone (50 ml) were added triethylamine (3.30 ml, 23.8 mmol) and phenacyl bromide (4.77 g, 24.0 mmol). The obtained mixture was stirred under ice-cooling for 1 hour and then at room temperature for 2 hours. After concentration under reduced pressure, ethyl acetate was added and the resulting mixture was successively washed with water, a saturated aqueous solution of sodium hydrogencarbonate and a saturated aqueous solution of sodium chloride. The ethyl acetate layer was dried over magnesium sulfate and concentrated under reduced pressure. Then a 5.5N hydrogen chloride/dioxane solution (77.8 ml, 0.428 mol) was added thereto and the mixture was allowed to stand at room temperature for 30 minutes. After concentration of the mixture under reduced pressure, the residue was dissolved in ethyl ether to produce crystals, the crystals were collected and washed with ethyl ether. Thus the title compound was obtained. Yield: 6.08 g (99.3%).

p) Boc-L-aIle-L-MeVal-OPac

To a solution of HCl•H-L-MeVal-OPac (1.12 g, 4.18 mmol) in dichloromethane (10 ml) were, added, under ice-cooling, Boc-L-aIle-OH (1.06 g, 4.59 mmol) and PyBroP (2.57 g, 5.49 mmol) and further DIEA (2.65 ml, 15.2 mmol) was added thereto. After stirring for 30 minutes under ice-cooling, the mixture was further stirred at room temperature for 17 hours. Then it was concentrated under reduced pressure and ethyl acetate was added thereto. The resulting mixture was successively washed with a saturated aqueous solution of sodium hydrogencarbonate, a saturated aqueous solution of sodium chloride, a 10% aqueous solution of citric acid and a saturated aqueous solution of sodium chloride. The ethyl acetate layer was dried over magnesium sulfate and concentrated under reduced pressure. The residue was purified by medium-pressure silica gel column chromatography (silica gel: 80 g, eluted with chloroform) to thereby give the title compound. Yield: 764 mg (36.0%).

q) Boc-L-aIle-L-MeVal-OH

Boc-L-aIle-L-MeVal-OPac (657 mg, 1.42 mmol) was dissolved in a 90% aqueous solution of acetic acid (70 ml). Then zinc dust (4.64 g, 71.0 mmol) was added thereto under ice-cooling while ultrasonically stirring. The mixture was ultrasonically stirred under ice-cooling for 7.5 hours. After removal of insoluble materials by filtration, the filtrate was concentrated under reduced pressure and ethyl acetate was added thereto. Then the mixture was successively washed with a 10% aqueous solution of citric acid and a saturated aqueous solution of sodium chloride. The ethyl acetate layer was dried over magnesium sulfate and concentrated under reduced pressure. The residue was precipitated from hexane and washed with hexane to thereby give the title compound. Yield: 325 mg (66.5%).

r) Boc-L-Leu-L-βHOMeVal-D-Hmp-L-MeVal-L-Phe-L-MePhe-L-Pro-OPac

To a solution of Boc-L-Leu-L-βHOMeVal-D-Hmp-OH (128 mg, 0.26 mmol) in dichloromethane (720 µl) were added, under ice-cooling, HCl•H-L-MeVal-L-Phe-L-MePhe-L-Pro-OPac (SEQ ID No. 7) (270 mg, 0.39 mmol) and PyBroP (158 mg, 0.34 mmol), and further DIEA (186 µl, 1.07 mmol) was added thereto. After stirring for 2 hours under ice-cooling, the mixture was further stirred at room temperature for 16 hours. Then it was concentrated under reduced pressure and ethyl acetate was added thereto. The resulting mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified by medium-pressure silica gel column chromatography (silica gel: 25 g, eluted with a toluene/ethyl acetate mixture 3:1) to thereby give the title compound having the structure of SEQ ID No. 8. Yield: 228 mg (78.7%).

s) HCl•H-L-Leu-L-βHOMeVal-D-Hmp-L-MeVal-L-Phe-L-MePhe-L-Pro-OPac

To Boc-L-Leu-L-βHOMeVal-D-Hmp-L-MeVal-L-Phe-L-MePhe-L-Pro-OPac (SEQ ID No. 8) (196 mg, 0.18 mmol) was added trifluoroacetic acid (1.11 ml, 14.1 mmol) under ice-cooling and the obtained mixture was allowed to stand under ice-cooling for 30 minutes. After concentration under reduced pressure, ethyl ether was added thereto. Then a 5.5N hydrogen chloride/dioxane solution (49 μl, 0.27 mmol) was further added under ice-cooling and the resulting mixture was allowed to stand at room temperature for 30 minutes. The crystals thus precipitated were washed with ethyl ether to thereby give the title compound having the structure of SEQ ID No. 9. Yield: 197 mg (93.0%)

t) Boc-L-aIle-L-MeVal-L-Leu-L-βHOMeVal-D-Hmp-L-MeVal-L-Phe-L-MePhe-L-Pro-OPac

Boc-L-aIle-L-MeVal-OH (97.2 mg, 0.28 mmol) and HCl•H-L-Leu-L-βHOMeVal-D-Hmp-L-MeVal-L-Phe-L-MePhe-L-Pro-OPac (SEQ ID No. 9). (197 mg, 0.19 mmol) were dissolved in DMF (400 μl), and HOObt (36.9 mg, 0.23 mmol) was added thereto under ice-cooling. Further, a solution of water-soluble carbodiimide hydrochloride (WSCD•HCl) (36.7 μl, 0.21 mmol) in DMF (100 μl) was added thereto and the mixture was stirred under ice-cooling for 2 hours. After stirring at room temperature for additional 2 hours, ethyl acetate was added and the mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified with medium-pressure silica gel column chromatography (silica gel: 10 g, eluted with a toluene/ethyl acetate mixture 6:1) to thereby give the title compound having the structure of SEQ ID No. 10. Yield: 150 mg (59.6%).

u) Boc-L-aIle-L-MeVal-L-Leu-L-βHOMeVal-D-Hmp-L-MeVal-L-Phe-L-MePhe-L-Pro-OH

Boc-L-aIle-L-MeVal-L-Leu-L-βHOMeVal-D-Hmp-L-MeVal-L-Phe-L-MePhe-L-Pro-OPac (SEQ ID No. 10) (59 mg, 44.1 μmol) was dissolved in a 90% aqueous solution of acetic acid (2.2 ml), and zinc dust (577 mg, 8.8 mmol) was added thereto under ice-cooling. Then the mixture was ultrasonically stirred under ice-cooling for 2 hours. After removal of insoluble materials by filtration, the filtrate was concentrated under reduced pressure. A 10% aqueous solution of citric acid was added to the residue, which was then extracted with ethyl acetate. The extract was washed with a saturated aqueous solution of sodium chloride, dried over magnesium sulfate and concentrated under reduced pressure to thereby give the title compound having the structure of SEQ ID No. 11. Yield: 53.9 mg (100%).

v) HCl•H-L-aIle-L-MeVal-L-Leu-L-βHOMeVal-D-Hmp-L-MeVal-L-Phe-L-MePhe-L-Pro-OH

To Boc-L-aIle-L-MeVal-L-Leu-L-βHOMeVal-D-Hmp-L-MeVal-L-Phe-L-MePhe-L-Pro-OH (SEQ ID No. 11) (53.0 mg, 43.5 μmol) was added trifluoroacetic acid (2.89 ml, 37.5 mmol) under ice-cooling and the obtained mixture was allowed to stand under ice-cooling for 20 minutes. After concentration under reduced pressure, ethyl ether was added thereto. Then a 5.5N hydrogen chloride/dioxane solution (11.9 μl, 63.5 μmol) was further added under ice-cooling and the resulting mixture was allowed to stand under ice-cooling for 30 minutes. The crystals thus precipitated were washed with ethyl ether to thereby give the title compound having the structure of SEQ ID No. 12. Yield: 45.8 mg (91.1%).

The physicochemical properties of the title compound are as follows: m.p.: 146°–148° C. $[\alpha]_D^{25.5}$: −149° (c 0.53, methanol). 270 MHz $^1$H-NMR (DMSO-d$_6$): δ 8.44 (br d, 1H), 7.97 (m, 2H), 7.62 (br d, 1H), 7.15–7.23 (m, 10H), 5.26 (br t, 1H), 5.24 (m, 1H), 5.24 (s, 1H), 4.72 (m, 1H), 4.70 (d, 1H), 4.49 (d, 1H), 4.32 (m, 1H), 4.13 (m, 1H), 3.27, 2.99, 2.89, 2.87 and 2.78 (total 12H, NCH$_3$), 1.35 (s, 3H), 1.24 (s, 3H), 0.71–0.96 (total 27H), CH$_3$), and others.

w) Compound 1

HCl•H-L-aIle-L-MeVal-L-Leu-L-βHOMeVal-D-Hmp-L-MeVal-L-Phe-L-MePhe-L-Pro-OH (SEQ ID No. 12) (5.0 mg, 4.3 μmol) and DIEA (1.5 μl, 8.6 μmol) were dissolved in dichloromethane (2.15 ml). The solution thus obtained was added dropwise to a solution of PyBroP (10.0 mg, 21.5 μmol) and DIEA (1.5 μl, 8.6 μmol) in dichloromethane (2.15 ml) within 2 hours at room temperature. Further, the obtained mixture was stirred at room temperature for 15 hours. After concentration under reduced pressure, ethyl acetate was added thereto and the mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified by high performance liquid chromatography (column: YMC A-323 ODS, 10×250 mm, eluted with 80% acetonitrile/water) to thereby give the title compound having the structure of SEQ ID No. 1. Yield: 2.1 mg (45.2%).

The physicochemical properties of the title compound are as follows: $[\alpha]_D^{20}$ −254.3° (c 1.0, methanol). UV λ$_{max}^{MeOH}$ ($E_{1\ cm}$): 258 (3.5), 264 (2.5). IR (KBr): 3450, 2970, 1750, 1640, 1415 cm$^{-1}$. Color reaction: Positive to 50% sulfuric acid and potassium permanganate. Negative to ninhydrin and ferric chloride.

EXAMPLE 2

Synthesis of DL-β-hydroxy-N-methylvaline(H-DL-βHOMeVal-OH)

a) 2-Acetoxymercuri-3-methoxy-3-methylbutanoic acid

Mercuric acetate (Hg(OAc)$_2$) (64 g, 0.2 mol) was added to methanol (300 ml). After dissolving by heating, the solution was quenched. Next, 3-methyl-2-butenoic acid (20 g, 0.2 mol) was added thereto and the mixture was allowed to stand at room temperature for 48 hours. The precipitate was collected by filtration and washed with methanol. Thus the title compound was obtained as a white powder. Yield: 53.6 g (89.9%).

b) 2-Bromo-3-methoxy-3-methylbutanoic acid

2-Acetoxymercuri-3-methoxy-3-methylbutanoic acid (54 g, 0.18 mol) was dissolved in an aqueous solution (200 ml) of potassium bromide (36 g, 0.3 mol). Then an aqueous solution (60 ml) of bromine (32 g, 0.2 mol) and potassium bromide (36 g, 0.3 mol) was added dropwise thereto under ice-cooling, stirring and irradiation with light within 1 hour in such a manner as to allow the color of bromine to remain. After stirring at room temperature for additional 1 hour, a small amount of a saturated aqueous solution of sodium thiosulfate was added thereto and then the mixture was washed with ethyl ether. A 47% aqueous solution of hydrogen bromide (30 ml) was added thereto and the mixture was extracted with ethyl ether (400 ml). The extract was washed with a saturated aqueous solution of sodium chloride, dried over sodium sulfate and concentrated under reduced pressure. Thus the title compound was obtained in a crude state.

Yield: 27.3 g (64.7%, based on 3-methyl-2-butenoic acid as the starting material).

c) DL-βHydroxy-N-methylvaline (H-DL-βHOMeVal-OH)

2-Bromo-3-methoxy-3-methylbutanoic acid (27.3 g, 0.13 mol) was dissolved in a 40% aqueous solution of methylamine (34.0 g, 1.1 mol/51 ml of water). The solution was stirred at 60° C. for 3 hours and then at 100° C. for additional 3 hours. After addition of water thereto, the mixture was concentrated under reduced pressure to thereby give an oily crude product (36 g). Then a 47% aqueous solution of hydrogen bromide (80 ml) was added thereto and the mixture was stirred at 100° C. for 6 hours. After concentration under reduced pressure, it was neutralized with sodium hydroxide under ice-cooling and diluted with 1500 ml of water. Then it was desalted with an electrodialyzer (Micro Acilyzer G3, manufactured by Asahi Chemical Industry Co., Ltd.) and purified by ion exchange column chromatography (Dowex 50W, eluted with 50% aqueous ammonia). The eluate was concentrated under reduced pressure and the residue was dissolved in methanol/water to give the title compound as crystals. Yield: 4.8 g (28.3%, calculating the crude 2-bromo-3-methoxy-3-methylbutanoic acid as the starting material).

EXAMPLE 3

Synthesis of Phenacyl (2R)-hydroxy-(3R)-methylpentanoate (H-D-Hmp-OPac)

a) (2R)-hydroxy-(3R)-methylpentanoic acid (H-D-Hmp-OH)

H-D-Ile-OH (3.00 g, 22.9 ml) was dissolved in a mixture of 1N hydrochloric acid (22.9 ml), water (91.6 ml) and acetic acid (45.8 ml). An aqueous solution (27.6 ml) of sodium nitrite (16.1 g, 0.23 mol) was added thereto under ice-cooling within 30 minutes. The mixture was stirred under ice-cooling for 20 minutes and then at room temperature for 15 hours and concentrated under reduced pressure. Then 1N hydrochloric acid solution was added thereto, and the obtained mixture was concentrated under reduced pressure. Water was further added thereto and concentrated under reduced pressure again. The residue was extracted with ethyl ether and the extract was washed with a saturated aqueous solution of sodium chloride, dried over magnesium sulfate and concentrated under reduced pressure. Thus the title compound was obtained. Yield: 2.52 g (83.2%)

b) Phenacyl (2R)-hydroxy-(3R)-methylpentanoate (H-D-Hmp-OPac)

To a solution of H-D-Hmp-OH (1.07 g, 8.09 mmol) in ethyl acetate (16 ml) was added phenacyl bromide (1.77 g, 8.90 mmol). Next, triethylamine (1.24 ml, 8.90 mmol) was added thereto under ice-cooling and the mixture was stirred under ice-cooling for 1 hour and then at room temperature for additional 15 hours. Then it was successively washed with distilled water, aqueous solution of sodium hydrogencarbonate and a saturated aqueous solution of sodium chloride. The ethyl acetate layer was dried over magnesium sulfate, concentrated under reduced pressure, and the residue was purified by medium pressure silica gel column chromatography (silica gel: 80 g, eluted with a toluene/ethyl acetate mixture 30:1) to thereby give the title compound. Yield: 1.52 g (75.2%).

EXAMPLE 4

Synthesis of cyclo(L-aIle-LMeVal-L-Leu-LMeThr-D-Hmp-L-MeVal-L-Phe-L-MePhe-L-Pro) (compound 19)

a) Boc-L-MeThr(Bzl)-OH

To a suspension of 60% sodium hydride (660 mg, 15.0 mmol), washed twice with hexane under argon atmosphere, in THF (5 ml), a solution of Boc-L-Thr(Bzl)-OH (1.55 g, 5.0 mmol) in THF (10 ml) was added under ice-cooling. After stirring for 5 min, methyl iodide (2.50 ml, 5.0 mmol) was added. The reaction mixture was stirred for 12 hours at room temperature, adjusted to pH 2 by 2N hydrochloric acid, and then extracted with ethyl acetate. The organic layer was washed with a saturated aqueous solution of sodium chloride, dried over anhydrous magnesium sulfate and concentrated under reduced pressure to give the title compound. Yield 1.09 g (67.6%).

b) Boc-L-MeThr(Bzl)-D-Hmp-OPac

Boc-L-MeThr(Bzl)-OH (647 mg, 2.00 mmol), D-Hmp-OPac (548 mg, 2.20 mmol) and 4-pyrrolidinopyridine (88.9 mg, 0.60 mmol) were dissolved in THF (4.0 ml), and DCC (454 mg, 2.20 mmol) was added thereto under ice-cooling. The obtained mixture was stirred under ice-cooling for 1 hour. Ethyl acetate was added thereto and the insoluble material produced was filtered off. The filtrate was concentrated and the residue obtained was dissolved in ethyl acetate. The solution was successively washed with a 10% aqueous solution of citric acid, a saturated aqueous solution of sodium chloride, a saturated aqueous sodium hydrogencarbonate and a saturated aqueous solution of sodium chloride. The ethyl acetate layer was dried over magnesium sulfate and concentrated under reduced pressure. The residue was purified by medium-pressure silica gel column chromatography (silica gel: 70 g, eluted with hexane/ethyl acetate mixtures 6:1 and then 4:1) to thereby give the title compound. Yield: 871 mg (78.6%).

c) HCl•H-L-MeThr(Bzl)-D-Hmp-OPac

To Boc-L-MeThr(Bzl)-D-Hmp-OPac (554 mg, 1.00 mmol) was added a 4.0N hydrogen chloride/dioxane solution (30 ml) and the mixture was allowed to stand at room temperature for 1 hour. After concentration under reduced pressure, the residue was washed with ethyl ether to give the title compound. Yield: 491 mg (99.8%).

d) Boc-L-Leu-L-MeThr(Bzl)-D-Hmp-OPac

To a solution of HCl•H-L-MeThr(Bzl)-D-Hmp-OPac (491 mg, 0.99 mmol) in dichloromethane (3 ml) were added, under ice-cooling, Boc-L-Leu-OH•H$_2$O (250 mg, 1.20 mmol) and PyBroP (559 mg, 1.20 mmol), and further DIEA (610 μl, 3.50 mmol) was added thereto. The mixture was stirred for 5 hours under ice-cooling, the mixture was concentrated under reduced pressure and ethyl acetate was added thereto. The resulting mixture was successively washed with a saturated aqueous solution of sodium hydrogencarbonate, a saturated aqueous solution of sodium chloride, a 10% aqueous solution of citric acid and a saturated aqueous solution of sodium chloride. The ethyl acetate layer was dried over magnesium sulfate and concentrated under reduced pressure. The residue was purified by medium-pressure silica gel column chromatography (silica gel: 30 g, eluted with hexane/ethyl acetate 3:1 and then 2:1) to thereby give the title compound. Yield: 432 mg (64.6%).

e) Boc-L-Leu-L-MeThr(Bzl)-D-Hmp-OH

Boc-L-Leu-L-MeThr(Bzl)-D-Hmp-OPac (177 mg, 0.26 mmol) was dissolved in a 90% aqueous solution of acetic acid (15 ml). Then zinc dust (3.00 g, 45.9 mmol) was added thereto under ice-cooling while ultrasonically-stirring. The mixture was ultrasonically stirred under ice-cooling for 5 hours. After removal of insoluble materials by filtration, the filtrate was concentrated under reduced pressure. Then a 10% aqueous solution of citric acid was added thereto and the mixture was extracted with ethyl acetate. The extract was washed with a saturated aqueous solution of sodium chloride and dried over magnesium sulfate. After concentration under reduced pressure, the residue was purified by medium-pressure silica gel column chromatography (silica gel: 6 g, eluted with a chloroform/acetic acid mixture 100:2) to thereby give the title compound. Yield: 125 mg (85.7%).

f) Boc-L-Leu-L-MeThr(Bzl)-D-Hmp-L-MeVal-L-Phe-L-MePhe-L-Pro-OPac

To a solution of Boc-L-Leu-L-MeThr(Bzl)-D-Hmp-OH (SEQ ID No. 7) (100 mg, 0.18 mmol) in dichloromethane (1 ml) were added, under ice-cooling, HCl•H-L-MeVal-L-Phe-L-MePhe-Pro-OPac (150 mg, 0.22 mmol) and PyBroP (110 mg, 0.24 mmol), and further DIEA (126 µl, 0.72 mmol) was added thereto. After stirring for 2 hours under ice-cooling, the mixture was further stirred at room temperature for 12 hours. Then it was concentrated under reduced pressure and ethyl acetate was added thereto. The resulting mixture was successively washed with a saturated aqueous solution of sodium hydrogencarbonate, a saturated aqueous solution of sodium chloride, a 10% aqueous solution of citric acid and a saturated aqueous solution of sodium chloride. The ethyl acetate layer was dried over magnesium sulfate and concentrated under reduced pressure. The residue was purified by medium-pressure silica gel column chromatography (silica gel: 7 g, eluted with a hexane/ethyl acetate mixture, 2:3) to thereby give the title compound having the structure of SEQ ID No. 13. Yield: 114 mg (52.8%).

g) HCl•H-L-Leu-L-MeThr(Bzl)-D-Hmp-L-MeVal-L-Phe-L-MePhe-L-Pro-OPac

To Boc-L-Leu-L-MeThr(Bzl)-D-Hmp-L-MeVal-L-Phe-L-MePhe-L-Pro-OPac (SEQ ID No. 13) (65 mg, 54.8 µmol) was added trifluoroacetic acid (1.00 ml, 13.0 mmol) under ice-cooling and the obtained mixture was allowed to stand under ice-cooling for 30 minutes. After concentration under reduced pressure, ethyl ether was added thereto. Then a 4.0N hydrogen chloride/dioxane solution (20.6 µl, 82.2 µmol) was further added under ice-cooling and the resulting mixture was allowed to stand at room temperature for 30 minutes. Crystals thus precipitated were washed with ethyl ether to thereby give the title compound having the structure of sequence ID No. 14. Yield: 52.9 mg (86.0%)

h) Boc-L-aIle-L-MeVal-L-Leu-L-MeThr(Bzl)-D-Hmp-L-MeVal-L-Phe-L-MePhe-L-Pro-OPac

Boc-L-aIle-L-MeVal-OH (32.0 mg, 93.0 µmol) and HCl•H-L-Leu-L-MeThr(Bzl)-D-Hmp-L-MeVal-L-Phe-L-MePhe-L-Pro-OPac (SEQ ID No. 14) (64.0 mg, 57.0 µmol) were dissolved in DMF (500 µl), and HOObt (11.5 mg, 85.1 µmol) was added thereto under ice-cooling. Further, a solution of WSCD (13.2 µl, 85.1 µmol) in DMF (300 µl) was added thereto and the mixture was stirred under ice-cooling for 2 hours. Ethyl acetate was added and the ethyl acetate extract was successively washed with a 10% aqueous solution of citric acid, a saturated aqueous solution of sodium chloride, a saturated aqueous sodium hydrogencarbonate and a saturated aqueous solution of sodium chloride. The ethyl acetate layer was dried over magnesium sulfate and concentrated under reduced pressure. The residue was purified with medium-pressure silica gel column chromatography (silica gel: 2 g, eluted with a hexane/ethyl acetate mixture 2:1) to thereby give the title compound having the structure of SEQ ID No. 15. Yield: 24.1 mg (29.9%).

i) Boc-L-aIle-L-MeVal-L-Leu-L-MeThr(Bzl)-D-Hmp-L-MeVal-L-Phe-L-MePhe-L-Pro-OH

Boc-L-aIle-L-MeVal-L-Leu-L-MeThr(Bzl)-D-Hmp-L-MeVal-L-Phe-L-MePhe-L-Pro-OPac (SEQ ID No. 15) (24.1 mg, 17.1 µmol) was dissolved in a 90% aqueous solution of acetic acid (7 ml). Then zinc dust (700 mg, 10.7 mmol) was added thereto under ice-cooling while ultrasonically stirring. The mixture was ultrasonically stirred under ice-cooling for 1 hour. After removal of insoluble materials by filtration, the filtrate was concentrated under reduced pressure. Then a 10% aqueous solution of citric acid was added to the residue and the mixture was extracted with ethyl acetate. The extract was washed with a saturated aqueous solution of sodium chloride, dried over magnesium sulfate and concentrated under reduced pressure to give the title compound having the structure of SEQ ID No. 16. Yield: 22.3 mg (100%).

j) HCl•H-L-aIle-L-MeVal-L-Leu-L-MeThr(Bzl)-D-Hmp-L-MeVal-L-Phe-L-MePhe-L-Pro-OH

To Boc-L-aIle-L-MeVal-L-Leu-L-MeThr(Bzl)-D-Hmp-L-MeVal-L-Phe-L-MePhe-L-Pro-OH (SEQ ID No. 16) (22.3 mg, 17.1 µmol) was added trifluoroacetic acid (2.0 ml, 26.0 mmol) under ice-cooling and the obtained mixture was allowed to stand under ice-cooling for 30 minutes. After concentration under reduced pressure, ethyl ether was added thereto. Then a 4.0N hydrogen chloride/dioxane solution (6.4 µl, 25.7 µmol) was further added under ice-cooling and the resulting mixture was allowed to stand at room temperature for 30 minutes. The crystals thus precipitated were washed with ethyl ether to thereby give the title compound having the structure of SEQ ID No. 17. Yield: 20.0 mg (94.2%).

270 MHz $^1$H-NMR (DMSO-d$_6$): δ 8.87, 8.79, 8.46, 8.02 and 7.85 (total 4H, NH), 7.37–7.10 (total 15H, aromatic), 5.45–4.10 (total 11H), 3.21, 3.00, 2.90 and 2.79 (total 12H, NCH$_3$), 0.95–0.62 (CH$_3$), and others.

k) Cyclo(L-aIle-L-MeVal-L-Leu-L-MeThr(Bzl)-D-Hmp-L-MeVal-L-Phe-L-MePhe-L-Pro)

HCl•H-L-aIle-L-MeVal-L-Leu-L-MeThr(Bzl)-D-Hmp-L-MeVal-L-Phe-L-MePhe-L-Pro-OH (SEQ ID No. 17) (17.0 mg, 13.8 µmol) and DIEA (4.8 µl, 27.6 µmol) were dissolved in dichloromethane (7 ml). The solution thus obtained was added dropwise to a solution of PyBroP (32.2 mg, 69.0 µmol) and DIEA (12.0 µl, 69.0 µmol) in dichloromethane (7 ml) within 6.5 hours under ice-cooling. Further, the obtained mixture was stirred under ice-cooling for 2 hours. After concentration under reduced pressure, ethyl acetate was added thereto and the ethyl acetate extract was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified by preparative thin-layer chromatography (developed and extracted with a chloroform/methanol mixture 19:1) to thereby give the title compound having the structure of SEQ ID No. 18. Yield: 2.5 mg (15.3%). 270 MHz $^1$H-NMR (CDCl$_3$): δ 8.88, 7.95 and 7.52 (total 3H, NH), 7.36–7.11 and 6.49 (total 15H, aromatic), 5.78, 5.62 and 5.23–3.50 (total 11H), 3.28, 3.23, 3.14, 2.76 and 2.63 (total 12H, NCH$_3$), 1.02–0.71 (CH$_3$), and others.

l) Cyclo(L-aIle-L-MeVal-L-Leu-L-MeThr-D-Hmp-L-MeVal-L-Phe-L-MePhe-L-Pro) (compound 19)

To a solution of cyclo(L-aIle-L-MeVal-L-Leu-L-MeThr(Bzl)-D-Hmp-L-MeVal-L-Phe-L-MePhe-L-Pro) (SEQ ID No. 18) (1.8 mg, 1.53 µmol) in ethyl acetate (30 ml) was added Pd-black (10 mg). Hydrogen gas was bubbled into the mixture for 3 hours and then 5 hours at room temperature. After removal of the catalyst by filtration, the filtrate was concentrated under reduced pressure and the residual oil was purified by the preparative silica gel thin-layer chromatography (developed and extracted with a chloroform/methanol mixture 19:1) to thereby give the title compound having the structure of SEQ ID No. 19. Yield: 1.1 mg (66.3%).

270 MHz $^1$H-NMR (CDCl$_3$): δ 8.89, 7.95 and 7.48 (total 3H, NH), 7.37–7.12 and 6.56 (total 10H, aromatic), 5.78, 5.71 and 5.31–3.49 (total 9H), 3.31, 3.17, 2.61 and 2.50 (total 12H, NCH$_3$), 0.98–0.70 (CH$_3$), and others.

EXAMPLE 5

Synthesis of cyclo(L-aIle-L-MeVal-L-Leu-D-βHOMeVal-D-Hmp-L-MeVal-L-Phe-L-MePhe-L-Pro) (compound 20)

Boc-L-Leu-D-βHOMeVal-D-Hmp-OPac was isolated by the silica gel chromatography of of Boc-L-Leu-DL-βHOMeVal-D-Hmp-OPac described in Example 1. m). The similar procedures with Example 1 using Boc-L-Leu-D-βHOMeVal-D-Hmp-OPac as the starting material gave the title compound. Yield: 3.9 mg (21.4%).

270 MHz $^1$H-NMR (CDCl$_3$): δ 8.73, 8.70, 7.87 and 7.80 (total 3H, NH), 7.22–7.07 and 6.50 (total 10H, aromatic), 5.59, 5.32, 5.24, 5.16, 5.12, 4.85, 4.43, 4.15 and 3.75–3.42 (total 12H), 3.25–2.42 (total 12H, NCH$_3$), 0.98–0.63 (CH$_3$), and others.

EXAMPLE 6

Synthesis of cyclo(L-aIle-L-MeVal-L-Leu-L-βHOMeVal-D-Hmp-L-MeVal-L-Phe-L-MePhe-D-Pro) (compound 21)

The similar procedures with Example 1 using Boc-D-Pro-OH as the starting material instead of Boc-L-Pro-OH gave the title compound. Yield: 2.1 mg.

270 MHz $^1$H-NMR (CDCl$_3$): δ 8.60, 8.57, 7.90 and 7.74 (total 3H, NH), 7.39–7.14 and 6.76 (total 10H, aromatic), 5.78, 5.31, 5.16–4.81 and 3.74–3.45 (total 12H), 3.40, 3.39, 3.30, 3.25, 2.82 and 2.57 (total 12H, NCH$_3$), 1.00–0.71 (CH$_3$), and others.

EXAMPLE 7

Synthesis of cyclo(L-aIle-L-MeVal-L-aIle-L-βHOMeVal-D-Hmp-L-MeVal-L-Phe-L-MePhe-L-Pro) (compound 24)

The same procedures as Example 1 using Boc-L-aIle-OH as the starting material instead of Boc-L-Leu-OH·H$_2$O gave the title compound having the structure of SEQ ID No. 20. Yield: 2.5 mg.

[α]$_D^{20}$:–247.5° (c 0.05, methanol). IR (KBr): 3480, 2960, 1750, 1640, 1410 cm$^{-1}$.

EXAMPLE 8

Synthesis of cyclo(L-GluOR-L-MeVal-L-Leu-L-βHOMeVal-D-Hmp-L-MeVal-L-Phe-L-MePhe-L-Pro) (R: Bzl) (compound 26)

a) Boc-L-Glu(OBzl)-L-MeVal-OPac

To a solution of Boc-L-Glu(OBzl)-OH (1.8 g, 5.25 mmol), HCl•H-L-MeVal-OPac (1.0 g, 3.50 mmol) and PyBroP (2.5 g, 5.25 mmol) in dichloromethane (10 ml) was added DIEA (2.44 ml, 14.0 mmol) under ice-cooling. The mixture was stirred for 2 hours under ice-cooling and additionally for 12 hours at room temperature. Then the mixture was concentrated under reduced pressure and ethyl acetate was added thereto. The organic layer was successively washed with a saturated aqueous solution of sodium hydrogencarbonate, a saturated aqueous solution of sodium chloride, a 10% aqueous solution of citric acid and a saturated aqueous solution of sodium chloride. The organic layer was dried over magnesium sulfate and concentrated under reduced pressure. The residue was purified by medium-pressure silica gel column chromatography (silica gel: 200 g, eluted with a toluene/ethyl acetate mixture, 5:1) to thereby give the title compound. Yield: 1.98 g (99.5%).

b) Boc-L-Glu(OBzl)-L-MeVal-OH

Boc-L-Glu(OBzl)-L-MeVal-OPac (2.54 g, 4.47 mmol) was dissolved in a 90% aqueous solution of acetic acid (224 ml). Then zinc dust (14.6 g, 220 mmol) was added thereto under ice-cooling while ultrasonically stirring. The mixture was ultrasonically stirred under ice-cooling for 1.5 hours. After removal of insoluble materials by filtration, the filtrate was concentrated under reduced pressure and ethyl acetate was added thereto. Then the ethyl acetate extract was successively washed with a 10% aqueous solution of citric acid and a saturated aqueous solution of sodium chloride. The ethyl acetate layer was dried over magnesium sulfate and concentrated under reduced pressure. The residue was washed with hexane to thereby give the title compound. Yield: 2.0 g (96.2%).

The similar procedures with Example 1 were used to obtain the following compounds having the structures of SEQ ID Nos. 21 to 24 in the respective yields as below.

c) Boc-L-Glu(OBzl)-L-MeVal-L-Leu-L-βHOMeVal-D-Hmp-L-MeVal-L-Phe-L-MePhe-L-Pro-OPac (SEQ ID No. 21).
Yield: 76.0 mg (91.9%).

d) Boc-L-Glu(OBzl)-L-MeVal-L-Leu-L-βHOMeVal-D-Hmp-L-MeVal-L-Phe-L-MePhe-L-Pro-OH (SEQ ID No. 22)
Yield: 37.7 mg (74%).

e) HCl•H-L-Glu(OBzl)-L-MeVal-L-Leu-L-βHOMeVal-D-Hmp-L-MeVal-L-Phe-L-MePhe-L-Pro-OH (SEQ ID No. 23)
Yield: 30.8 mg (97.8%).

270 MHz $^1$H-NMR (DMSO-d$_6$): δ 8.88, 8.67, 8.42, 8.21 and 7.61(total 4H, NH), 7.37–7.15 (total 15H, aromatic), 5.43–3.83 (total 12H), 3.27, 3.01, 2.88 and 2.79 (total 12H, NCH$_3$), 0.96–0.71 (CH$_3$), and others.

f) Cyclo(L-GluOR-L-MeVal-L-Leu-L-βHOMeVal-D-Hmp-L-MeVal-L-Phe-L-MePhe-L-Pro) (R: Bzl) (SEQ ID No. 24, compound 26)
Yield: 1.05 mg (5.3%).

270 MHz $^1$H-NMR (CDCl$_3$): δ 9.10, 8.62, 8.02 and 7.51(total 3H, NH), 7.38–7.05 (total 15H, aromatic), 5.80–3.87 (total 12H), 3.30, 3.16, 3.13, 2.64 and 2.51 (total 12H, NCH$_3$), 0.98–0.73 (CH$_3$), and others.

EXAMPLE 9

Synthesis of cyclo(L-aIle-L-ROMeNva-L-Leu-L-βHOMeVal-D-Hmp-L-MeVal-L-Phe-L-MePhe-L-Pro) (R: Bzl) (compound 27)

a) Boc-L-5-hydroxynorvaline (Boc-L-HONva-OH)

To a suspension of lithium aluminum hydride (1.23 g, 32.5 mmol) in ethyl ether (18 ml), a solution of Boc-L-Glu(OBzl)-OH (6.0 g, 17.8 mmol) in ethyl ether was added dropwise in 30 minutes with stirring under ice-cooling. After stirring for 30 minutes at room temperature, the reaction mixture was heated under reflux for 3.5 hours. Under ice-cooling, a 10% aqueous solution of citric acid was added dropwise in 30 minutes, and then the insoluble material was filtered off with Hyflo-super cell. The ethyl ether layer was collected. The aqueous layer of the filtrate was extracted with ethyl acetate. The organic layers were combined and washed with a saturated aqueous solution of sodium chloride and dried over anhydrous magnesium sulfate. After concentration under reduced pressure, the residue was purified with medium-pressure silica gel column chromatography (silica gel: 150 g, eluted with a chloroform/methanol/acetic acid mixture 95:5:3) to thereby give the title compound. Yield: 2.56 g (61.8%).

b) Boc-L-5-benzyloxynorvaline (Boc-L-RONva-OH) (R: Bzl)

To a solution of Boc-L-HONva-OH (500 mg, 2.14 mmol) in DMF (5 ml) was added NaH (124 mg, 5.14 mmol) under ice-cooling. After completion of evolution of hydrogen, benzyl bromide (330 µl, 2.78 mmol) was added and the mixture was stirred for 4.5 hours under ice-cooling. Then the mixture was concentrated under reduced pressure, the residual oil was acidified at pH 4 with 10% aqueous solution of citric acid, and extracted with ethyl acetate. The organic layer was washed with a saturated aqueous solution of sodium chloride, dried over anhydrous magnesium sulfate and concentrated under reduced pressure to give the title compound. Yield: 341 mg (49.2%).

c) Boc-L-ROMeNva-OH (R: Bzl)

To a solution of Boc-L-RONva-OH (R: Bzl) (77.3 mg, 0.239 mmol) and methyl iodide (119 µl, 1.91 mmol) in THF (5 ml) was added sodium hydride (17.2 mg, 0.717 mmol) under ice-cooling. The mixture was stirred for 30 minutes under ice-cooling, additionally for 4 hours at room temperature, and concentrated under reduced pressure. The residue was purified by preparative silica gel thin-layer chromatography (developed with a chloroform/methanol mixture 19:1) to thereby give the title compound. Yield: 45.1 mg (55.9%).

d) Boc-L-ROMeNva-OPac (R: Bzl)

To a solution of Boc-L-ROMeNva-OH (R: Bzl) (96.1 mg, 0.285 mmol) in ethyl acetate (1 ml) were added triethylamine (43.6 ml, 0.314 mmol) and phenacyl bromide (62.5 mg, 0.314 mmol). The obtained mixture was stirred under ice-cooling for 40 minutes and then at room temperature for 4.5 hours. After concentration under reduced pressure, ethyl acetate was added and the ethyl acetate extract was successively washed with water, a saturated aqueous solution of sodium hydrogencarbonate and a saturated aqueous solution of sodium chloride. The ethyl acetate layer was dried over magnesium sulfate and concentrated under reduced pressure. The residue was purified by preparative silica gel thin-layer chromatography (developed with a benzene/ethyl acetate mixture 3:1 and extracted with ethyl acetate) to thereby give the title compound. Yield: 84.1 mg (64.7%).

e) HCl•H-L-ROMeNva-OPac (R: Bzl)

To Boc-L-ROMeNva-OPac (R: Bzl) (80.0 mg, 0.18 mmol) was added a 5.5N hydrogen chloride/dioxane solution (640 µl, 3.51 mmol) and the mixture was allowed to stand at room temperature for 45 minutes. After concentration under reduced pressure, the residue was dissolved in ethyl ether and the solution was allowed to stand under ice-cooling for 1 hour. Crystals thus precipitated were collected and washed with ethyl ether. Thus the title compound was obtained. Yield: 61.4 mg (87.0%)

f) Boc-L-alle-L-ROMeNva-OPac (R: Bzl)

To a solution containing Boc-L-alle-OH (48.6 mg, 0.210 mmol), HCl•H-L-ROMeNva-OPac (R: Bzl) (55.0 mg, 0.140 mmol) and PyBroP (98.0 mg, 0.210 mmol) in dichloromethane (300 ml), DIEA (97.6 µl, 0.560 mmol) was added under ice-cooling. The mixture was stirred for 15 hours under ice-cooling, concentrated under reduced pressure and ethyl acetate was added thereto. The ethyl acetate layer was successively washed with a saturated aqueous solution of sodium hydrogencarbonate, a saturated aqueous solution of sodium chloride, a 10% aqueous solution of citric acid and a saturated aqueous solution of sodium chloride, dried over magnesium sulfate, and concentrated under reduced pressure. The residue was purified by preparative silica gel thin-layer chromatography (developed with a benzene/ethyl acetate mixture 5:1 and extracted with ethyl acetate) to thereby give the title compound. Yield: 66.8 mg (83.9%).

g) Boc-L-alle-L-ROMeNva-OH (R: Bzl)

Boc-L-alle-L-ROMeNva-OPac (R: Bzl) (60.0 mg, 0.106 mmol) was dissolved in a 90% aqueous solution of acetic acid (5.3 ml). Then zinc dust (345 mg, 5.28 mmol) was added thereto under ice-cooling while ultrasonically stirring. The mixture was ultrasonically stirred under ice-cooling for 1.5 hours. After removal of insoluble materials by filtration, the filtrate was concentrated under reduced pressure and ethyl acetate was added thereto. Then the mixture was successively washed with a 10% aqueous solution of citric acid and a saturated aqueous solution of sodium chloride, dried over magnesium sulfate, and concentrated under reduced pressure. The residue was purified by preparative silica gel thin-layer chromatography (developed and extracted with a chloroform/methanol/acetic acid mixture 95:5:3) to thereby give the title compound. Yield: 48.0 mg (100%).

The similar procedures with Example 1 were used to obtain the following compounds having the structures of SEQ ID Nos. 25 to 28 in the respective yields as below.

h) Boc-L-alle-L-ROMeNva-L-Leu-L-βHOMeVal-D-Hmp-L-MeVal-L-Phe-L-MePhe-L-Pro-OPac (R: Bzl) (SEQ ID No. 25)

Yield: 26.2 mg (50.0%).

i) Boc-L-alle-L-ROMeNva-L-Leu-L-βHOMeVal-D-Hmp-L-MeVal-L-Phe-L-MePhe-L-Pro-OH (R: Bzl) (SEQ ID No. 26)

Yield: 24.4 mg (93.8%).

j) HCl•H-L-alle-L-ROMeNva-L-Leu-L-βHOMeVal-D-Hmp-L-MeVal-L-Phe-L-MePhe-L-pro-OH (R: Bzl) (SEQ ID No. 27)

Yield: 21.1 mg (93.0%).

270 MHz $^1$H-NMR (DMSO-$d_6$): δ 8.27, 8.03 and 7.63 (total 4H, NH), 7.35–7.13 (total 15H, aromatic), 5.44–4.11 (total 11H), 3.26, 2.96, 2.89, 2.88 and 2.79 (total 12H, NCH$_3$), 1.06–0.71 (CH$_3$), and others.

k) Cyclo(L-alle-L-ROMeNva-L-Leu-L-βHOMeVal-D-Hmp-L-MeVal-L-Phe-L-MePhe-L-Pro) (R: Bzl) (compound 27, SEQ ID No. 28)

Yield: 4.9 mg (34%).

270 MHz $^1$H-NMR (CDCl$_3$): δ 8.85, 8.72 and 7.90 (total 3H, NH), 7.40–7.04 and 6.45 (total 15H, aromatic), 5.73, 5.67 and 5.24–3.67 (total 12H), 3.29, 3.26, 3.12, 2.61 and 2.48 (total 12H, NCH$_3$), 0.97–0.66 (CH$_3$), and others.

EXAMPLE 10

Synthesis of cyclo(L-alle-L-HOMeNva-L-Leu-L-βHOMeVal-D-Hmp-L-MeVal-L-Phe-L-MePhe-L-Pro) (compound 28)

To a solution of cyclo(L-alle-L-ROMeNva-L-Leu-L-βHOMeVal-D-Hmp-L-MeVal-L-Phe-L-MePhe-L-Pro) (R: Bzl) (compound 27, SEQ ID No. 28) (3.0 mg, 2.46 µmol) in methanol (20 ml), Pd-black (30 mg) was added. Hydrogen gas was bubbled into the mixture for 3 hours at room temperature. After removal of the catalyst by filtration, the filtrate was concentrated under reduced pressure to thereby give the title compound having the SEQ ID No. 29. Yield: 2.4 mg (87.3%).

EXAMPLE 11

Synthesis of cyclo(L-alle-L-Hmb-L-Leu-L-βHOMeVal-D-Hmp-L-MeVal-L-Phe-L-MePhe-L-Pro) (compound 29)

a) (2S)-hydroxy-3-methylbutanoic acid (H-L-Hmb-OH)

H-L-Val-OH (2.34 g, 20 mmol) was dissolved in a mixture of 1N hydrochloric acid (20 ml), water (80 ml) and acetic acid (40 ml). An aqueous solution (24.1 ml) of sodium nitrite (14 g, 0.2 mol) was added thereto under ice-cooling within 30 minutes. The mixture was stirred under ice-cooling for 20 minutes and then at room temperature for 15 hours. The mixture was concentrated under reduced pressure and 1N hydrochloric acid was added thereto. The obtained mixture was concentrated under reduced pressure and water was further added thereto. After concentration under reduced pressure again, it was extracted with ethyl ether. The extract was washed with a saturated aqueous solution of sodium chloride, dried over magnesium sulfate and concentrated under reduced pressure to give the title compound Yield: 1.95 g (82.7%)

b) H-L-Hmb-OPac

To a solution of H-L-Hmb-OH (743 mg, 6.30 mmol) in ethyl acetate (12 ml) was added phenacyl bromide (1.38 g, 6.93 mmol). Next, triethylamine (962 µl, 6.93 mmol) was added thereto under ice-cooling and the mixture was stirred under ice-cooling for 1 hour and at room temperature for additional 15 hours. Then the mixture was successively washed with distilled water, a saturated aqueous solution of sodium hydrogencarbonate and a saturated aqueous solution of sodium chloride. The ethyl acetate layer was dried over magnesium sulfate and concentrated under reduced pressure. The residue was purified by medium pressure silica gel column chromatography (silica gel: 50 g, eluted with a hexane/ethyl acetate mixture 4:1) to thereby give the title compound. Yield: 1.19 g (80.0%).

c) Boc-L-aIle-L-Hmb-OPac

L-Hmb-OPac (612 mg, 2.59 mmol), Boc-L-aIle-OH (659 mg, 2.85 mmol) and 4-pyrrolidinopyridine (126 mg, 0.85 mmol) were dissolved in THF (4 ml) and DCC (587 mg, 2.85 mmol) was added thereto under ice-cooling. The obtained mixture was stirred under ice-cooling for 20 hours. After concentration under reduced pressure, ethyl acetate was added thereto and the mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue obtained was purified by medium-pressure silica gel column chromatography (silica gel: 70 g, eluted with a hexane/ethyl acetate mixture 4:1) to thereby give the title compound. Yield: 960 mg (82.4%).

d) Boc-L-aIle-L-Hmb-OH

Boc-L-aIle-L-Hmb-OPac (808 mg, 1.80 mmol) was dissolved in a 90% aqueous solution of acetic acid (1130 ml). Then zinc dust (2.00 g, 30.6 mmol) was added thereto under ice-cooling while ultrasonically stirring. The mixture was ultrasonically stirred under ice-cooling for 7.5 hours. After removal of insoluble materials by filtration, the filtrate was concentrated under reduced pressure and ethyl acetate was added thereto. Then the mixture was successively washed with a 10% aqueous solution of citric acid and a saturated aqueous solution of sodium chloride. The ethyl acetate layer was dried over magnesium sulfate and concentrated under reduced pressure. The residue was dissolved in hexane to produce crystals. The crystals thus precipitated were washed with hexane to thereby give the title compound. Yield: 479 mg (80.4%).

e) Boc-L-aIle-L-Hmb-L-Leu-L-βHOMeVal-D-Hmp-L-MeVal-L-Phe-L-MePhe-L-Pro-OPac

To a solution of Boc-L-aIle-L-Hmb-OH (28.5 mg, 86 µmol) and HCl•H-L-Leu-L-βHOMeVal-D-Hmp-L-MeVal-L-Phe-L-MePhe-L-Pro-OPac (60.0 mg, 57 µmol) in dichloromethane (1.0 ml), PyBroP (38.3 mg, 86 µmol) was added under ice-cooling, and further DIEA (39.7 µl, 228 µmol) was added thereto. After stirring for 4 hours under ice-cooling, the mixture was concentrated under reduced pressure and ethyl acetate was added thereto. The resulting mixture was successively washed with a saturated aqueous solution of sodium hydrogencarbonate, a saturated aqueous solution of sodium chloride, a 10% aqueous solution of citric acid and a saturated aqueous solution of sodium chloride. The ethyl acetate layer was dried over magnesium sulfate and concentrated under reduced pressure. The residue was purified by preparative silica gel thin-layer chromatography (developed with a hexane/ethyl acetate mixture (1:2) and extracted with ethyl acetate) to thereby give the title compound having the structure of SEQ ID No. 30. Yield: 49.0 mg (64.5%).

The similar procedures with Example 1 were used to obtain the following compounds having the structures of SEQ ID Nos. 31 to 33 in the respective yields as below.

f) Boc-L-aIle-L-Hmb-L-Leu-L-βHOMeVal-D-Hmp-L-MeVal-L-Phe-L-MePhe-L-Pro-OH (SEQ ID No. 31)
Yield: 44.6 mg (100%).

g) HCl•H-L-aIle-L-Hmb-L-Leu-L-βHOMeVal-D-Hmp-L-MeVal-L-Phe-L-MePhe-L-Pro-OH (SEQ ID No. 32)
Yield: 36.3 mg (85.9%).

270 MHz $^1$H-NMR (DMSO-d$_6$): δ 8.88, 8.45, 8.32 and 7.64 (total 4H, NH), 7.34–6.97 (total 10H, aromatic), 5.45–4.03 (total 8H), 3.26, 2.89, 2.88 and 2.79 (total 9H, N—CH$_3$), 1.06–0.65 (CH$_3$), and others.

h) Cyclo(L-aIle-L-Hmb-L-Leu-L-βHOMeVal-D-Hmp-L-MeVal-L-Phe-L-MePhe-L-Pro) (compound 29, SEQ ID No. 33)
Yield: 3.0 mg (27.2%).

270 MHz $^1$H-NMR (CDCl$_3$): δ 8.31 and 8.16 (total 2H, NH), 7.33–7.16 and 6.90 (total 10H, aromatic), 5.87–3.41 (total 10H), 3.27, 3.12 and 2.81 (total 9H, N—CH$_3$), 2.30 (m, 2H), 2.08 (m, 2H), 1.03–0.77 (CH$_3$), and others.

EXAMPLE 12

Preparation of cyclo(L-aIle-L-MeVal-L-Leu-L-βHOMeVal-(2R,3s)-Hmp-L-MeVal-L-Phe-L-MePhe-L-Pro) (compound 18), cyclo (L-aIle-L-MeaIle-L-Leu-L-βHOMeVal-D-Hmp-L-MeVal-L-Phe-L-MePhe-L-Pro) (compound 22), cyclo(L-aIle-L-MeLeu-L-Leu-L-βHOMeVal-D-Hmp-L-MeVal-L-Phe-L-MePhe-L-Pro) (compound 23), cyclo(L-aIle-L-MeVal-L-aIle-LβHOMeVal-D-Hmp-L-MeVal-L-Phe-L-MePhe-L-Pro) (compound 24) by a fermentation method.

*Aureobasidium pullulans* No. R106 (FERM BP-1938) was incubated with shaking in a 500-ml Erlenmeyer flask containing 100 ml of a liquid medium (Difco-yeast nitrogen base 0.67%, glucose 2%, w/v) at 25° C. for 2 days to give a seed culture. The seed culture (1000 ml) was transferred into a 200-liter jar fermenter containing 100 liters of a liquid medium A (glucose 2%, (NH$_4$)$_2$SO$_4$·0.5%, KH$_2$PO$_4$ 0.15%, MgSO$_4$·7H$_2$O 0.05%, CaCl$_2$ 0.01%, NaCl 0.01% (concentrations are all w/v), FeCl$_3$ 0.5 µg/ml, ZnSO$_4$ 0.5 µg/ml) and cultured at 25° C. for 90 hours with aeration (100 liters/min) and agitation (190 rpm). To the culture was added liquid medium B (10-fold concentrations of liquid medium A described above) and fermentation was further carried out at 25° C. for 90 hours with aeration (100 liters/min) and agitation (190 rpm).

To the cultured broth thus obtained was added 126 liters of ethanol, mixed thoroughly to obtain a extract. The extract was centrifuged and the supernatant obtained was charged on a HP-40 (manufactured by Mitsubishi Chemicals Industries Co., Ltd.) column (7.5 cm i.d.×120 cm) equilibrated with 50% ethanol, washed with 30 liters of 50% ethanol, and eluted with 33 liters of 95% ethanol to obtain an active fraction. The fraction was diluted with water to be 40% ethanol and charged on a ODS (manufactured by Soken Chemicals Co., Ltd., ODS-W type, 74/150 µm) column (4.5 cm i.d.×60 cm), washed with 40% ethanol, and eluted with 60% ethanol. Fractions containing compounds 18, 22, 23 and 24 were collected and concentrated in vacuo to dryness. The residue was dissolved in acetonitrile and purified by preparative high performance liquid chromatography (column: Capcell Pak C$_{18}$ (manufactured by Shiseido Co., Ltd.), 1 cm i.d×25 cm, mobile phase: 67% (v/v) acetonitrile-water, 3 ml/min; detection: UV 230 nm) to separate those compounds. Eluted peaks containing the compounds (compound 24 is eluted at 50 min, compound 18 is at 52 min, compound 23 is at 54 min, compound 22 is at 59 min) were independently collected, concentrated in vacuo to dryness to give respective white powders, 25 mg of compound 18 (SEQ ID No. 34), 15 mg of compound 22 (SEQ ID No. 35), 30 mg of compound 23 (SEQ ID No. 36), and 20 mg of compound 24 (SEQ ID No. 20).

The physico-chemical properties of compounds 18, 22 to 24 are shown below.

Compound 18: $[\alpha]_D^{20}$–236.5° (c 0.12, methanol). IR (KBr): 3450, 3320, 2960, 1740, 1630, 1410 cm$^{-1}$.

Compound 22: $[\alpha]_D^{20}$–213.3° (c 0.03, methanol). IR (KBr): 3480, 2960, 1750, 1640, 1410 cm$^{-1}$.

Compound 23: $[\alpha]_D^{20}$–191.4° (c 0.035, methanol). IR (KBr): 3450, 2960, 1750, 1640, 1410 cm$^{-1}$.

Compound 24: $[\alpha]_D^{20}$–247.5° (c 0.05, methanol). IR (KBr): 3480, 3320, 2950, 1750, 1640, 1410 cm$^{-1}$.

EXAMPLE 13

Synthesis of cyclo(L-GluOR-L-MeVal-L-Leu-L-βHOMeVal-D-Hmp-L-MeVal-L-Phe-L-MePhe-L-Pro) (R: n-butyl) (compound 30)

a) Cyclo(L-Glu-L-MeVal-L-Leu-L-βHOMeVal-D-Hmp-L-MeVal-L-Phe-L-MePhe-L-Pro)

To a solution of cyclo(L-GluOR-L-MeVal-L-Leu-L-βHOMeVal-D-Hmp-L-MeVal-L-Phe-L-MePhe-L-Pro) (R: Bzl) (compound 26, SEQ ID No. 24) (6.0 mg, 4.91 µmol) in methanol (15 ml) was added Pd-black (15 mg). Then hydrogen gas was blown into the obtained mixture at room temperature for 2 hours. After removal of the catalyst by filtration, the filtrate was concentrated under reduced pressure to thereby give the title compound having the structure of SEQ ID No. 37. Yield: 4.97 mg (89.4%).

270 MHz $^1$H-NMR (DMSO-d$_6$): δ 8.80, 8.32, 8.11, 7.93 and 7.70 (total 3H, NH), 7.35–7.13 and 6.49 (total 10H, aromatic), 6.03–3.91 (total 12H), 3.35, 3.31, 3.28, 3.19, 3.16, 2.91 and 2.61 (total 12H, NCH$_3$), 1.03–0.79 (CH$_3$), and others.

b) Cyclo(L-GluOR-L-MeVal-L-Leu-L-βHOMeVal-D-Hmp-L-MeVal-L-Phe-L-MePhe-L-Pro) (R: n-butyl)

Cyclo(L-Glu-L-MeVal-L-Leu-L-βHOMeVal-D-Hmp-L-MeVal-L-Phe-L-MePhe-L-Pro) (SEQ ID No. 37) (2.0 mg, 1.79 µmol), 1-butanol (0.82 µl, 8.84 µmol), 4-dimethylaminopyridine (0.11 mg, 0.89 µmol) were dissolved in dichloromethane (40 µl) and DCC (0.74 mg, 3.58 µmol) was added thereto under ice-cooling. The obtained mixture was stirred under ice-cooling for 4 hours. Then the mixture was purified by preparative silica gel thin layer chromatography (developed with a chloroform/methanol mixture 19:1) to thereby give the title compound having the structure of SEQ ID No. 38. Yield: 2.0 mg (95.2%).

270 MHz $^1$H-NMR (CDCl$_3$): δ 9.06, 8.64, 8.04, 7.96 and 7.55 (total 3H, NH), 7.36–7.05 and 6.40 (total 10H, aromatic), 5.78 (1H), 5.26–4.01 (total 13H), 3.31, 3.28, 3.20, 3.16, 3.14, 2.71 and 2.51 (total 12H, NCH$_3$), 0.99–0.78 (CH$_3$), and others.

EXAMPLE 14

Synthesis of cyclo(L-GluOR-L-MeVal-L-Leu-L-βHOMeVal-D-Hmp-L-MeVal-L-Phe-L-MePhe-L-Pro) (R: n-hexyl) (compound 31)

Cyclo(L-Glu-L-MeVal-L-Leu-L-βHOMeVal-D-Hmp-L-MeVal-L-Phe-L-MePhe-L-Pro) (SEQ ID No. 37) (2.0 mg, 1.79 µmol), 1-hexanol (1.13 µl, 8.84 µmol) and 4-dimethylaminopyridine (0.11 mg, 0.89 µmol) were dissolved in dichloromethane (40 µl) and DCC (0.74 mg, 3.58 µmol) was added thereto under ice-cooling. The obtained mixture was stirred under ice-cooling for 3.5 hours. Then the mixture was purified by preparative silica gel thin layer chromatography (developed with a chloroform/methanol mixture 19:1) to thereby give the title compound having the structure of SEQ ID No. 39. Yield: 2.03 mg (94.4%).

270 MHz $^1$H-NMR (CDCl$_3$): δ 9.06, 8.64, 8.04, 7.96 and 7.55 (total 3H, NH), 7.36–7.11, 6.40 (total 10H, aromatic), 5.79 (1H), 5.22–3.96 (total 1H), 3.31, 3.28, 3.20, 3.16, 3.14, 3.13, 2.71 and 2.51 (total 12H, NCH$_3$), 1.36–1.25 (8H, aliphatic CH$_2$), 0.99–0.72 (CH$_3$), and others.

EXAMPLE 15

Synthesis of cyclo(L-GluOR-L-MeVal-L-Leu-L-βHOMeVal-D-Hmp-L-MeVal-L-Phe-L-MePhe-L-Pro) (R: n-octyl) (compound 32)

Cyclo(L-Glu-L-MeVal-L-Leu-L-βHOMeVal-D-Hmp-L-MeVal-L-Phe-L-MePhe-L-Pro) (SEQ ID No. 37) (2.0 mg, 1.79 µmol), 1-octanol (1.5 µl, 8.84 µmol), 4-dimethylaminopyridine (0.11 mg, 0.89 µmol) were dissolved in dichloromethane (40 µl) and DCC (0.73 mg, 3.54 µmol) was added thereto under ice-cooling. The obtained mixture was stirred under ice-cooling for 2 hours. Then the mixture was purified by preparative silica gel thin layer chromatography (developed with a chloroform/methanol mixture 19:1) to thereby give the title compound having the structure of SEQ ID No. 40. Yield: 1.18 mg (53.6%).

270 MHz $^1$H-NMR (CDCl$_3$): δ 9.07, 8.63, 8.00 and 7.54 (total 3H, NH), 7.31–7.02 and 6.37 (total 10H, aromatic), 5.78 (1H), 5.20–3.91 (total 13H), 3.30–3.14, 2.70 and 2.51 (total 12H, NCH$_3$), 1.25 (12H, aliphatic CH$_3$), 0.95–0.77 (CH$_3$), and others.

EXAMPLE 16

Synthesis of cyclo(L-GluOR-L-MeVal-L-Leu-L-βHOMeVal-D-Hmp-L-MeVal-L-Phe-L-MePhe-L-Pro) (R: n-decyl) (compound 33)

Cyclo(L-Glu-L-MeVal-L-Leu-L-βHOMeVal-D-Hmp-L-MeVal-L-Phe-L-MePhe-L-Pro) (SEQ ID No. 37) (2.0 mg, 1.79 µmol), 1-decanol (1.71 µl, 8.84 µmol), 4-dimethylaminopyridine (0.11 mg, 0.89 µmol) were dissolved in dichloromethane (40 µl) and DCC (0.74 mg, 3.58 µmol) was added thereto under ice-cooling. The obtained mixture was stirred under ice-cooling for 3.5 hours. Then the mixture was purified by preparative silica gel thin layer chromatography (developed with a chloroform/methanol mixture, 19:1) to thereby give the title compound having the structure of SEQ ID No. 41. Yield: 2.22 mg (98.7%).

270 MHz $^1$H-NMR (CDCl$_3$): δ 9.06, 8.64, 8.04, 7.96 and 7.54 (total 3H, NH), 7.36–7.05 and 6.39 (total 10H, aromatic), 5.78 (1H), 5.20–4.00 (total 13H), 3.31, 3.28 3.20, 3.17, 3.14, 3.13, 2.71 and 2.51 (total 12H, NCH$_3$), 1.24 (16H, aliphatic CH$_2$), 0.99–0.74 (CH$_3$), and others.

EXAMPLE 17

Synthesis of cyclo(L-GluOR-L-MeVal-L-Leu-L-βHOMeVal-D-Hmp-L-MeVal-L-Phe-L-MePhe-L-Pro) (R: cis-3-hexenyl) (compound 34)

Cyclo(L-Glu-L-MeVal-L-Leu-L-βHOMeVal-D-Hmp-L-MeVal-L-Phe-L-MePhe-L-Pro) (SEQ ID No. 37) (1.5 mg, 1.34 µmol), cis-3-hexen-1-ol (0.8 µl, 6.79 µmol), 4-dimethylaminopyridine (0.082 mg, 0.67 µmol) were dissolved in dichloromethane (50 and DCC (0.6 mg, 2.68 µmol) was added thereto under ice-cooling. The obtained mixture was stirred under ice-cooling for 6 hours. Then the mixture was purified by preparative silica gel thin layer chromatography (developed with a chloroform/methanol mixture 19:1) to thereby give the title compound having the structure of SEQ ID No. 42. Yield: 1.36 mg (84.5%).

270 MHz $^1$H-NMR (CDCl$_3$): δ 9.06, 8.64, 8.04, 7.95 and 7.55 (total 3H, NH), 7.36–7.05 and 6.39 (total 10H, aromatic), 5.78–4.67, 4.08 and 3.48 (total 15H), 3.31, 3.28, 3.21, 3.17, 3.15, 2.72 and 2.52 (total 12H, NCH$_3$), 0.97–0.74 (CH$_3$), and others.

EXAMPLE 18

Synthesis of cyclo(L-GluOR-L-MeVal-L-Leu-L-βHOMeVal-D-Hmp-L-MeVal-L-Phe-L-MePhe-L-Pro) (R: trans-3-hexenyl) (compound 35)

Cyclo(L-Glu-L-MeVal-L-Leu-L-βHOMeVal-D-Hmp-L-MeVal-L-Phe-L-MePhe-L-Pro) (SEQ ID No. 37) (1.5 mg, 1.34 μmol), trans-3-hexen-1-ol (0.8 μl, 6.70 μmol), 4-dimethylaminopyridine (0.082 mg, 0.67 μmol) were dissolved in dichloromethane (50 μl) and DCC (0.6 mg, 2.68 μmol) was added thereto under ice-cooling. The obtained mixture was stirred under ice-cooling for 6 hours. Then the mixture was purified by preparative silica gel thin layer chromatography (developed with a chloroform/methanol mixture 19:1) to thereby give the title compound having the structure of SEQ ID No. 43. Yield: 1.29 mg (80.1%).

270 MHz $^1$H-NMR (CDCl$_3$): δ 9.06, 8.64, 8.04, 7.95 and 7.61 (total 3H, NH), 7.39–7.05 and 6.40 (total 10H, aromatic), 5.81–4.65, 4.09 and 3.48 (total 15H), 3.31, 3.28, 3.20, 3.17, 3.15, 2.72 and 2.52 (total 12H, NCH$_3$), 0.98–0.74 (CH$_3$), and others.

EXAMPLE 19

Synthesis of cyclo(L-HONva-L-MeVal-L-Leu-L-βHOMeVal-D-Hmp-L-MeVal-L-Phe-L-MePhe-L-Pro) (compound 36)

To a solution of cyclo(L-Glu-L-MeVal-L-Leu-L-βHOMeVal-D-Hmp-L-MeVal-L-Phe-L-MePhe-L-Pro) (SEQ ID No. 37) (4.0 mg, 3.58 μmol) in DMF (50 μl), N-hydroxysuccinimide (0.83 mg, 7.16 μmol) was added, and further WSCD•HCl (EDC•HCl) (1.40 mg, 7.16 μmol) was added thereto under ice-cooling. After stirring for 5 hours under ice-cooing, ethyl acetate was added thereto. The resulting mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was dissolved in THF (80 μl) and sodium borohydride (NaBH$_4$) (0.34 mg, 8.95 μmol) was added thereto under ice-cooling. The obtained mixture was stirred under ice-cooling for 3.5 hours and added to a ice-cooled 10% aqueous solution of citric acid. The reaction mixture was extracted with ethyl acetate and the extract was washed with a saturated aqueous solution of sodium chloride. The ethyl acetate layer was dried over magnesium sulfate and concentrated under reduced pressure. The residue was purified by preparative silica gel thin layer chromatography (developed by a ethyl acetate/methanol mixture 7:1) to thereby give the title compound having the structure of SEQ ID No. 44. Yield: 2.8 mg (71%).

270 MHz $^1$H-NMR (CDCl$_3$): δ 9.03, 8.57, 8.08, 7.99 and 7.57 (total 3H, NH), 7.36–7.07 and 6.47 (total 10H, aromatic), 5.77 (1H), 5.22–3.75 (total 13H), 3.31, 3.28, 3.26, 3.17, 3.15, 3.13, 2.66 and 2.54 (total 12H, NCH$_3$), 0.99–0.73 (CH$_3$), and others.

EXAMPLE 20

Synthesis of cyclo(L-RONva-L-MeVal-L-Leu-L-βHOMeVal-D-Hmp-L-MeVal-L-Phe-L-MePhe-L-Pro) (R: n-hexanoyl) (compound 37)

To a solution of cyclo(L-HONva-L-MeVal-L-Leu-L-βHOMeVal-D-Hmp-L-MeVal-L-Phe-L-MePhe-L-Pro) (SEQ ID No. 44) (2.0 mg, 1.81 μmol) in dichloromethane (50 μl) were added n-hexanoic acid (1.14 μl, 9.05 μmol) and 4-dimethylaminopyridine (0.12 mg, 0.91 μmol), and further DCC (0.75mg, 3.62 μmol) was added thereto under ice-cooling. The mixture was stirred under ice-cooling for 6 hours. Then the mixture was purified by preparative silica gel thin layer chromatography (developed with a chloroform/methanol mixture 19:1) to thereby give the title compound having the structure of SEQ ID No. 45. Yield: 2.17 mg (100%)

270 MHz $^1$H-NMR (CDCl$_3$): δ 9.09, 8.67, 8.00, 7.98 and 7.66 (total 3H, NH), 7.36–7.04 and 6.45 (total 10H, aromatic), 5.82–4.60, 4.26–3.85 and 3.48 (total 15H), 3.31, 3.28, 3.27, 3.16, 3.14, 2.72 and 2.52 (total 12H, NCH$_3$), 0.98–0.72 (CH$_3$), and others.

EXAMPLE 21

Synthesis of cyclo(L-aIle-L-MeVal-L-GluOR-L-βHOMeVal-D-Hmp-L-MeVal-L-Phe-L-MePhe-L-Pro) (R: cHex) (compound 38)

a) Boc-L-Glu(OcHex)-DL-βHOMeVal-OBzl

To a solution of Boc-L-Glu(OcHex)-OH (2.71 g, 8.22 mmol) in dichloromethane (12 ml) were added HCl•H-DL-βHOMeVal-OBzl (1.5 g, 5.48 mmol) and PyBroP (3.83 g, 8.22 mmol), and further DIEA (3.82 ml, 21.9 mmol) was added thereto under ice-cooling. The mixture was stirred under ice-cooling for 20 hours. Then it was concentrated under reduced pressure and ethyl acetate was added thereto. The resulting mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified by medium-pressure silica gel column chromatography (silica gel: 200 g, eluted with a toluene/ethyl acetate mixture 5:1) to thereby give the title compound. Yield: 2.16 g (71.8%).

b) Boc-L-Glu(OcHex)-DL-βHOMeVal-OH

To a solution of Boc-L-Glu(OcHex)-DL-βHOMeVal-OBzl (550 mg, 1.00 mmol) in methanol (50 ml) was added Pd-black (150 mg). Then hydrogen gas was blown into the obtained mixture at room temperature for 3 hours. After removal of the catalyst by filtration, the filtrate was concentrated under reduced pressure to thereby give the title compound. Yield: 422 mg (92.0%).

c) Boc-L-Glu(OcHex)-DL-βHOMeVal-D-Hmp-OPac

Boc-L-Glu(OcHex)-DL-βHOMeVal-OH (420 mg, 0.916 mmol), H-D-Hmp-OPac (275 mg, 1.10 mmol) and 4-pyrrolidinopyridine (40.8 mg, 0.275 mmol) were dissolved in THF (2 ml) and DCC (226 mg, 1.10 mmol) was added thereto under ice-cooling. The obtained mixture was stirred under ice-cooling for 8 hours. Then it was concentrated under reduced pressure and ethyl acetate was added thereto. After removal of insoluble materials by filtration, the filtrate was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified by medium-pressure silica gel column chromatography (silica gel: 40 g, eluted with a toluene/ethyl acetate mixture 5:1) to thereby give the title compound. Yield: 465 mg (74.5%).

d) Boc-L-Glu(OcHex)-L-βHOMeVal-D-Hmp-OH

Boc-L-Glu(OcHex)-DL-βHOMeVal-D-Hmp-OPac (470 mg, 0.681 mmol) was dissolved in a 90% aqueous solution of acetic acid (34.1 ml). Then zinc dust (8.9 g, 136 mmol) was added thereto under ice-cooling while ultrasonically stirring. The mixture was ultrasonically stirred under ice-cooling for 2.5 hours. After removal of insoluble materials by filtration, the filtrate was concentrated under reduced pressure. Then a 10% aqueous solution of citric acid was added thereto and the mixture was extracted with ethyl acetate. The extract was washed with a saturated aqueous solution of sodium chloride. The ethyl acetate layer was dried over magnesium sulfate and concentrated under reduced pressure. The residue was purified by high performance liquid chromatography (column: YMC SH-363-5, 30×250 mm, eluted with 60% acetonitrile/water) to thereby give the title compound. Yield: 118 mg (59%, based on the L-L-D compound contained in Boc-L-Glu(OcHex)-DL-βHOMeVal-D-Hmp-OPac as the starting material).

e) Boc-L-Glu(OcHex)-L-βHOMeVal-D-Hmp-L-MeVal-L-Phe-L-MePhe-L-Pro-OPac

To a solution of Boc-L-Glu(OcHex)-L-βHOMeVal-D-Hmp-OH (67.0 mg, 0.114 mmol) in dichloromethane (500 µl) were added HCl•H-L-MeVal-L-Phe-L-MePhe-L-Pro-OPac (119 mg, 0.171 mmol) and PyBroP (63.9 mg, 0.137 mmol), and further DIEA (79.4 µl, 0.456 mmol) was added thereto under ice-cooling. After stirring for 3 hours under ice-cooling, the mixture was further stirred under room temperature for 2 hours. Then it was concentrated under reduced pressure and ethyl acetate was added thereto. The resulting mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was purified by medium-pressure silica gel column chromatography (silica gel: 7 g, eluted with a toluene/ethyl acetate mixture 3:1) to thereby give the title compound having the structure of SEQ ID No. 46. Yield: 101 mg (72.2%).

f) HCl•H-L-Glu(OcHex)-L-βHOMeVal-D-Hmp-L-MeVal-L-Phe-L-MePhe-L-Pro-OPac

To Boc-L-Glu(OcHex)-L-βHOMeVal-D-Hmp-L-MeVal-L-Phe-L-MePhe-L-Pro-OPac (SEQ ID No. 46) (150 mg, 0.123 mmol) was added trifluoroacetic acid (760 µl, 9.86 mmol) under ice-cooling and the obtained mixture was allowed to stand under ice-cooling for 45 minutes. After concentration under reduced pressure, ethyl ether was added thereto. Then a 5.5N hydrogen chloride/dioxane solution (45 µl, 0.246 mmol) was further added under ice-cooling and the resulting mixture was allowed to stand under ice-cooling for 30 minutes. The crystals thus precipitated were washed with ethyl ether to thereby give the title compound having the structure of SEQ ID No. 47. Yield: 123 mg (87.2%).

The similar procedures with Example 1 were used to obtain the following compounds having the structures of SEQ ID Nos. 48 to 51 in the respective yields as below.

g) Boc-L-aIle-L-MeVal-L-Glu(OcHex)-L-βHOMeVal-D-Hmp-L-MeVal-L-Phe-L-MePhe-L-Pro (SEQ ID No. 48)

Yield: 61.8 mg (76.1%)

h) Boc-L-aIle-L-MeVal-L-Glu(OcHex)-L-βHOMeVal-D-Hmp-L-MeVal-L-Phe-L-MePhe-L-Pro-OH (SEQ ID No. 49)

Yield: 50.5 mg (100%)

i) HCl•H-L-aIle-L-MeVal-L-Glu(OcHex)-L-βHOMeVal-D-Hmp-L-MeVal-L-Phe-L-MePhe-L-Pro-OH (SEQ ID No. 50)

Yield: 44.9 mg (95.5%)

270 MHz $^1$H-NMR (DMSO-$d_6$): δ 8.88 (t), 8.54 (d), 8.06 (s) and 7.64 (d) (total 4H, NH), 7.23–7.12 (total 10H, aromatic), 5.29–4.11 (total 13H), 3.28, 3.24, 2.99, 2.89 and 2.78 (total 12H, NCH$_3$), 0.96–0.71 (CH$_3$), and others.

j) Cyclo(L-aIle-L-MeVal-L-GluOR-L-βHOMeVal-D-Hmp-L-MeVal-L-Phe-L-MePhe-L-Pro) (R: cHex) (compound 38, SEQ ID No. 51)

Yield: 9.6 mg (28.6%)

270 MHz $^1$H-NMR (CDCl$_3$): δ 8.89, 8.85, 7.95 and 7.61 (total 3H, NH), 7.39–7.09 and 6.51 (total 10H, aromatic), 5.77 (1H), 5.22–3.73 (total 13H), 3.32, 3.30, 3.19, 3.15, 3.07, 2.64 and 2.48 (total 12H, NCH$_3$), 1.01–0.72(CH$_3$), and others.

EXAMPLE 22

Synthesis of cyclo(L-aIle-L-MeVal-L-HONva-L-βHOMeVal-D-Hmp-L-MeVal-L-Phe-L-MePhe-L-Pro) (compound 39)

a) Cyclo(L-aIle-L-MeVal-L-Glu-L-βHOMeVal-D-Hmp-L-MeVal-L-Phe-L-MePhe-L-Pro)

To cyclo(L-aIle-L-MeVal-L-GluOR-L-βHOMeVal-D-Hmp-L-MeVal-L-Phe-L-MePhe-L-Pro) (R: cHex) (compound 38, SEQ ID No. 51) (6.5 mg, 5.35 µmol) in the reaction tube, hydrogen fluoride (5 ml) was introduced under cooling at −78° C. The mixture was stirred at under ice-cooling for 30 minutes. Then hydrogen fluoride was evaporated under ice-cooling and then concentrated under reduced pressure for 30 minutes. The residue obtained was lyophilized to give a powder, which was purified by preparative silica gel thin layer chromatography (developed by a chloroform/methanol mixture 19:1) to thereby give the title compound having the structure of SEQ ID No. 52. Yield: 5.5 mg (90.2%).

270 MHz $^1$H-NMR (CDCl$_3$): δ 8.83, 8.16, 7.94, 7.90 and 7.79 (total 3H, NH), 7.41–7.10, 6.51 (total 10H, aromatic), 5.75 (1H), 5.39–4.43, 4.20, and 3.43 (total 14H), 3.31, 3.20, 3.15, 3.08, 2.66 and 2.49 (total 12H, NCH$_3$), 0.99–0.72 (CH$_3$), and others.

b) Cyclo(L-aIle-L-MeVal-L-HONva-L-βHOMeVal-D-Hmp-L-MeVal-L-Phe-L-MePhe-L-Pro) (compound 39)

To a solution of cyclo(L-aIle-L-MeVal-L-Glu-L-βHOMeVal-D-Hmp-L-MeVal-L-Phe-L-MePhe-L-Pro) (SEQ ID No. 52) (2.0 mg, 1.76 µmol) in DMF (40 µl), N-hydroxysuccinimide (0.41 mg, 3.52 µmol) was added, and further WSCD•HCl (EDC•HCl) (0.68 mg, 3.52 µmol) was added thereto under ice-cooling. After stirring for 4 hours under ice-cooling, ethyl acetate was added thereto. The resulting mixture was successively washed with a 10% aqueous solution of citric acid, a saturated aqueous solution of sodium chloride, a saturated aqueous solution of sodium hydrogencarbonate and a saturated aqueous solution of sodium chloride. The ethyl acetate layer was dried over magnesium sulfate and concentrated under reduced pressure. The residue was dissolved in THF (50 µl) and NaBH$_4$ (0.17 mg, 4.40 µmol) was added thereto under ice-cooling. The obtained mixture was stirred under ice-cooling for 2 hours and added to a ice-cooled 10% aqueous solution of citric acid. The reaction mixture was extracted with ethyl acetate and the extract was washed with a saturated aqueous solution of sodium chloride. The ethyl acetate layer was dried over magnesium sulfate and concentrated under reduced pressure. The residue was purified by preparative silica gel thin layer chromatography (developed by a chloroform/methanol mixture (19:1)) to thereby give the title compound having the structure of SEQ ID No. 53. Yield: 0.96 mg (49.5%).

270 MHz $^1$H-NMR (CDCl$_3$): δ 8.89, 8.16, 7.97 and 7.79 (total 3H, NH), 7.40–7.01 and 6.51 (total 10H, aromatic), 5.76 (1H), 5.34–4.17 (total 11H), 3.30, 3.20, 3.15, 3.08, 2.65 and 2.49 (total 12H, NCH$_3$), 0.95–0.71 (CH$_3$), and others.

The present invention provides a new process for producing a cyclic peptide, which is useful as an antifungal drug.

More specifically, by the present invention, a linear peptide of the formula (II) can be prepared in a stereochemically pure state and the linear peptide can be then converted into a cyclic peptide of the formula (I) in a good yield. Therefore, although prior art microbiological methods can only provide an aureobasidin containing some congeners, a pure aureobasidin can be obtained by the present invention. Further, by the present invention, a structural modification of an aureobasidin including a substitution of amino acid(s) and a process for preparing a novel cyclic peptide which are more useful clinically has become possible.

What is claimed is:

1. A cyclic peptide represented by the following formula (III):

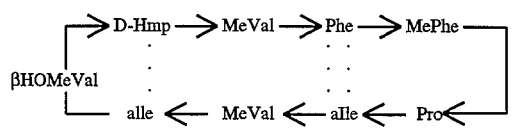

wherein D-Hmp represents 2(R)-hydroxy-3(R)-methylpentanoate; and the dotted lines represent intramolecular hydrogen bonds.

* * * * *

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
( A ) LENGTH: 8 amino acids
( B ) TYPE: amino acid
( C ) STRANDEDNESS: single
( D ) TOPOLOGY: circular ( i i ) MOLECULE TYPE: peptide ( i x ) FEATURE:
( A ) NAME/KEY:
( B ) LOCATION: 1,6
( C ) IDENTIFICATION METHOD:
( D ) OTHER INFORMATION: /note="MeVal"

( i x ) FEATURE:
( A ) NAME/KEY:
( B ) LOCATION: 3
( C ) IDENTIFICATION METHOD:
( D ) OTHER INFORMATION: /note="N-methylphenylalanine(MePhe)"

( i x ) FEATURE:
( A ) NAME/KEY:
( B ) LOCATION: 5
( C ) IDENTIFICATION METHOD:
( D ) OTHER INFORMATION: /note="aIle"

( i x ) FEATURE:
( A ) NAME/KEY:
( B ) LOCATION: 8
( C ) IDENTIFICATION METHOD:
( D ) OTHER INFORMATION: /note="beta-hydroxy-N-methylvaline
( b e t a - H O M e V a l ), its carboxyl group has substituent 2(R)-
hydroxy-3(R)- methylpentanoic acid (D-Hmp) to form ester
bond (beta- HOMeVal-D-Hmp), and carboxyl group of D-Hmp
is bound to location 1."

( x i ) SEQUENCE DESCRIPTION: SEQ ID NO:1:

Xaa  Phe  Xaa  Pro  Xaa  Xaa  Leu  Xaa
 1                     5

( 2 ) INFORMATION FOR SEQ ID NO:2:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
  ( A ) NAME/KEY:
  ( B ) LOCATION: 1
  ( C ) IDENTIFICATION METHOD:
  ( D ) OTHER INFORMATION: /note="MeVal, its amino group having as a substituent D-Hmp to form the amido bond."

( i x ) FEATURE:
  ( A ) NAME/KEY:
  ( B ) LOCATION: 3
  ( C ) IDENTIFICATION METHOD:
  ( D ) OTHER INFORMATION: /note="MePhe"

( i x ) FEATURE:
  ( A ) NAME/KEY:
  ( B ) LOCATION: 5
  ( C ) IDENTIFICATION METHOD:
  ( D ) OTHER INFORMATION: /note="aIle"

( i x ) FEATURE:
  ( A ) NAME/KEY:
  ( B ) LOCATION: 6
  ( C ) IDENTIFICATION METHOD:
  ( D ) OTHER INFORMATION: /note="MeVal"

( i x ) FEATURE:
  ( A ) NAME/KEY:
  ( B ) LOCATION: 8
  ( C ) IDENTIFICATION METHOD:
  ( D ) OTHER INFORMATION: /note="beta-hydroxy-N- methylvaline(beta-HOMeVal)"

( x i ) SEQUENCE DESCRIPTION: SEQ ID NO:2:

Xaa Phe Xaa Pro Xaa Xaa Leu Xaa
1       5

( 2 ) INFORMATION FOR SEQ ID NO:3:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY:
    ( B ) LOCATION: 1
    ( C ) IDENTIFICATION METHOD:
    ( D ) OTHER INFORMATION: /note="MeVal"

( i x ) FEATURE:
    ( A ) NAME/KEY:
    ( B ) LOCATION: 3
    ( C ) IDENTIFICATION METHOD:
    ( D ) OTHER INFORMATION: /note="MePhe"

( x i ) SEQUENCE DESCRIPTION: SEQ ID NO:3:

Xaa Phe Xaa Pro
1

( 2 ) INFORMATION FOR SEQ ID NO:4:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:

-continued

```
            (A) NAME/KEY:
            (B) LOCATION: 1
            (C) IDENTIFICATION METHOD:
            (D) OTHER INFORMATION: /note="aIle"

(ix) FEATURE:
            (A) NAME/KEY:
            (B) LOCATION: 2
            (C) IDENTIFICATION METHOD:
            (D) OTHER INFORMATION: /note="MeVal"

(ix) FEATURE:
            (A) NAME/KEY:
            (B) LOCATION: 4
            (C) IDENTIFICATION METHOD:
            (D) OTHER INFORMATION: /note="beta-HOMeVal-D-Hmp, the
                    carboxyl group of D-Hmp being bound to the amino acid
                    in location 5."

(ix) FEATURE:
            (A) NAME/KEY:
            (B) LOCATION: 5
            (C) IDENTIFICATION METHOD:
            (D) OTHER INFORMATION: /note="MeVal"

(ix) FEATURE:
            (A) NAME/KEY:
            (B) LOCATION: 7
            (C) IDENTIFICATION METHOD:
            (D) OTHER INFORMATION: /note="MePhe"

(xi) SEQUENCE DESCRIPTION: SEQ ID NO:4:

Xaa  Xaa  Leu  Xaa  Xaa  Phe  Xaa  Pro
 1                    5

(2) INFORMATION FOR SEQ ID NO:5:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY:
            (B) LOCATION: 2
            (C) IDENTIFICATION METHOD:
            (D) OTHER INFORMATION: /note="beta-HOMeVal-D-Hmp, the
                    carboxyl group of D-Hmp being bound to the amino acid
                    in location 3."

(ix) FEATURE:
            (A) NAME/KEY:
            (B) LOCATION: 3
            (C) IDENTIFICATION METHOD:
            (D) OTHER INFORMATION: /note="MeVal"

(ix) FEATURE:
            (A) NAME/KEY:
            (B) LOCATION: 5
            (C) IDENTIFICATION METHOD:
            (D) OTHER INFORMATION: /note="MePhe"

(xi) SEQUENCE DESCRIPTION: SEQ ID NO:5:

Leu  Xaa  Xaa  Phe  Xaa  Pro
 1               5

(2) INFORMATION FOR SEQ ID NO:6:

(i) SEQUENCE CHARACTERISTICS:
            (A) LENGTH: 4 amino acids
            (B) TYPE: amino acid
```

( C ) STRANDEDNESS: single
( D ) TOPOLOGY: linear ( i i ) MOLECULE TYPE: peptide ( i x ) FEATURE:
    ( A ) NAME/KEY:
    ( B ) LOCATION: 1
    ( C ) IDENTIFICATION METHOD:
    ( D ) OTHER INFORMATION: /note="MeVal, its amino group having as a substituent t-butyloxycarbonyl (Boc) group. (Boc-MeVal)"

( i x ) FEATURE:
    ( A ) NAME/KEY:
    ( B ) LOCATION: 3
    ( C ) IDENTIFICATION METHOD:
    ( D ) OTHER INFORMATION: /note="MePhe"

( i x ) FEATURE:
    ( A ) NAME/KEY:
    ( B ) LOCATION: 4
    ( C ) IDENTIFICATION METHOD:
    ( D ) OTHER INFORMATION: /note="Pro, its carboxyl group being protected by phenacyl (Pac) group. (Pro-OPac)"

( x i ) SEQUENCE DESCRIPTION: SEQ ID NO:6:

Xaa Phe Xaa Xaa
1

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY:
    ( B ) LOCATION: 1
    ( C ) IDENTIFICATION METHOD:
    ( D ) OTHER INFORMATION: /note="HCl MeVal"

( i x ) FEATURE:
    ( A ) NAME/KEY:
    ( B ) LOCATION: 3
    ( C ) IDENTIFICATION METHOD:
    ( D ) OTHER INFORMATION: /note="MePhe"

( i x ) FEATURE:
    ( A ) NAME/KEY:
    ( B ) LOCATION: 4
    ( C ) IDENTIFICATION METHOD:
    ( D ) OTHER INFORMATION: /note="Pro-OPac"

( x i ) SEQUENCE DESCRIPTION: SEQ ID NO:7:

Xaa Phe Xaa Xaa
1

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY:

```
            ( B ) LOCATION: 1
            ( C ) IDENTIFICATION METHOD:
            ( D ) OTHER INFORMATION: /note="Leu, its amino group having
                    as a substituent Boc group. (Boc-Leu)"

( i x ) FEATURE:
            ( A ) NAME/KEY:
            ( B ) LOCATION: 2
            ( C ) IDENTIFICATION METHOD:
            ( D ) OTHER INFORMATION: /note="beta-HOMeVal-D-Hmp, the
                    carboxyl group of D-Hmp being bound to the amino acid
                    in location 3."

( i x ) FEATURE:
            ( A ) NAME/KEY:
            ( B ) LOCATION: 3
            ( C ) IDENTIFICATION METHOD:
            ( D ) OTHER INFORMATION: /note="MeVal"

( i x ) FEATURE:
            ( A ) NAME/KEY:
            ( B ) LOCATION: 5
            ( C ) IDENTIFICATION METHOD:
            ( D ) OTHER INFORMATION: /note="MePhe"

( i x ) FEATURE:
            ( A ) NAME/KEY:
            ( B ) LOCATION: 6
            ( C ) IDENTIFICATION METHOD:
            ( D ) OTHER INFORMATION: /note="Pro-OPac"

( x i ) SEQUENCE DESCRIPTION: SEQ ID NO:8:

Xaa  Xaa  Xaa  Phe  Xaa  Xaa
 1                 5

( 2 ) INFORMATION FOR SEQ ID NO:9:

( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY:
            ( B ) LOCATION: 1
            ( C ) IDENTIFICATION METHOD:
            ( D ) OTHER INFORMATION: /note="HCl Leu"

( i x ) FEATURE:
            ( A ) NAME/KEY:
            ( B ) LOCATION: 2
            ( C ) IDENTIFICATION METHOD:
            ( D ) OTHER INFORMATION: /note="beta-HOMeVal-D-Hmp, the
                    carboxyl group of D-Hmp being bound to the amino acid
                    in location 3."

( i x ) FEATURE:
            ( A ) NAME/KEY:
            ( B ) LOCATION: 3
            ( C ) IDENTIFICATION METHOD:
            ( D ) OTHER INFORMATION: /note="MeVal"

( i x ) FEATURE:
            ( A ) NAME/KEY:
            ( B ) LOCATION: 5
            ( C ) IDENTIFICATION METHOD:
            ( D ) OTHER INFORMATION: /note="MePhe"

( i x ) FEATURE:
            ( A ) NAME/KEY:
            ( B ) LOCATION: 6
            ( C ) IDENTIFICATION METHOD:
            ( D ) OTHER INFORMATION: /note="Pro-OPac"
```

( x i ) SEQUENCE DESCRIPTION: SEQ ID NO:9:

Xaa Xaa Xaa Phe Xaa Xaa
1               5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note="alle, its amino group having
            as a substituent Boc group. (Boc-aIle)"

( i x ) FEATURE:
        ( A ) NAME/KEY:
        ( B ) LOCATION: 2
        ( C ) IDENTIFICATION METHOD:
        ( D ) OTHER INFORMATION: /note="MeVal"

( i x ) FEATURE:
        ( A ) NAME/KEY:
        ( B ) LOCATION: 4
        ( C ) IDENTIFICATION METHOD:
        ( D ) OTHER INFORMATION: /note="beta-HOMeVal-D-Hmp, the
            carboxyl group of D-Hmp being bound to the amino acid in
            location 5."

( i x ) FEATURE:
        ( A ) NAME/KEY:
        ( B ) LOCATION: 5
        ( C ) IDENTIFICATION METHOD:
        ( D ) OTHER INFORMATION: /note="MeVal"

( i x ) FEATURE:
        ( A ) NAME/KEY:
        ( B ) LOCATION: 7
        ( C ) IDENTIFICATION METHOD:
        ( D ) OTHER INFORMATION: /note="MePhe"

( i x ) FEATURE:
        ( A ) NAME/KEY:
        ( B ) LOCATION: 8
        ( C ) IDENTIFICATION METHOD:
        ( D ) OTHER INFORMATION: /note="Pro-OPac"

( x i ) SEQUENCE DESCRIPTION: SEQ ID NO:10:

Xaa Xaa Leu Xaa Xaa Phe Xaa Xaa
1               5

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note="Boc-aIle"

-continued ( i x ) FEATURE:
              ( A ) NAME/KEY:
              ( B ) LOCATION: 2
              ( C ) IDENTIFICATION METHOD:
              ( D ) OTHER INFORMATION: /note="MeVal"

( i x ) FEATURE:
              ( A ) NAME/KEY:
              ( B ) LOCATION: 4
              ( C ) IDENTIFICATION METHOD:
              ( D ) OTHER INFORMATION: /note="beta-HOMeVal-D-Hmp, the
                        carboxyl group of D-Hmp being bound to the amino acid in
                        location 5."

( i x ) FEATURE:
              ( A ) NAME/KEY:
              ( B ) LOCATION: 5
              ( C ) IDENTIFICATION METHOD:
              ( D ) OTHER INFORMATION: /note="MeVal"

( i x ) FEATURE:
              ( A ) NAME/KEY:
              ( B ) LOCATION: 7
              ( C ) IDENTIFICATION METHOD:
              ( D ) OTHER INFORMATION: /note="MePhe"

( x i ) SEQUENCE DESCRIPTION: SEQ ID NO:11:

Xaa Xaa Leu Xaa Xaa Phe Xaa Pro
1                   5

( 2 ) INFORMATION FOR SEQ ID NO:12:

( i ) SEQUENCE CHARACTERISTICS:
              ( A ) LENGTH: 8 amino acids
              ( B ) TYPE: amino acid
              ( C ) STRANDEDNESS: single
              ( D ) TOPOLOGY: linear ( i i ) MOLECULE TYPE: peptide ( i x ) FEATURE:
              ( A ) NAME/KEY:
              ( B ) LOCATION: 1
              ( C ) IDENTIFICATION METHOD:
              ( D ) OTHER INFORMATION: /note="HCl aIle"

( i x ) FEATURE:
              ( A ) NAME/KEY:
              ( B ) LOCATION: 2
              ( C ) IDENTIFICATION METHOD:
              ( D ) OTHER INFORMATION: /note="MeVal"

( i x ) FEATURE:
              ( A ) NAME/KEY:
              ( B ) LOCATION: 4
              ( C ) IDENTIFICATION METHOD:
              ( D ) OTHER INFORMATION: /note="beta-HOMeVal-D-Hmp, the
                        carboxyl group of D-Hmp being bound to the amino acid
                        in location 5."

( i x ) FEATURE:
              ( A ) NAME/KEY:
              ( B ) LOCATION: 5
              ( C ) IDENTIFICATION METHOD:
              ( D ) OTHER INFORMATION: /note="MeVal"

( i x ) FEATURE:
              ( A ) NAME/KEY:
              ( B ) LOCATION: 7
              ( C ) IDENTIFICATION METHOD:
              ( D ) OTHER INFORMATION: /note="MePhe"

( x i ) SEQUENCE DESCRIPTION: SEQ ID NO:12:

Xaa Xaa Leu Xaa Xaa Phe Xaa Pro
1                   5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note="Boc-Leu"

( i x ) FEATURE:
        ( A ) NAME/KEY:
        ( B ) LOCATION: 2
        ( C ) IDENTIFICATION METHOD:
        ( D ) OTHER INFORMATION: /note="N-methylthreonine (MeThr),
            its hydroxy group being substituted by benzyl (Bzl) group
            and its carboxyl group being substituted by D-Hmp
            ( M e T h r ( Bzl)-D-Hmp). The carboxyl group of D-Hmp is bound
            to the amino acid in location 3."

( i x ) FEATURE:
        ( A ) NAME/KEY:
        ( B ) LOCATION: 3
        ( C ) IDENTIFICATION METHOD:
        ( D ) OTHER INFORMATION: /note="MeVal"

( i x ) FEATURE:
        ( A ) NAME/KEY:
        ( B ) LOCATION: 5
        ( C ) IDENTIFICATION METHOD:
        ( D ) OTHER INFORMATION: /note="MePhe"

( i x ) FEATURE:
        ( A ) NAME/KEY:
        ( B ) LOCATION: 6
        ( C ) IDENTIFICATION METHOD:
        ( D ) OTHER INFORMATION: /note="Pro-OPac"

( x i ) SEQUENCE DESCRIPTION: SEQ ID NO:13:

Xaa Xaa Xaa Phe Xaa Xaa
1               5

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note="HCl Leu"

( i x ) FEATURE:
        ( A ) NAME/KEY:
        ( B ) LOCATION: 2
        ( C ) IDENTIFICATION METHOD:
        ( D ) OTHER INFORMATION: /note="MeThr(Bzl)-D-Hmp, the
            carboxyl group of D-Hmp being bound to the amino acid
            in location 3."

( i x ) FEATURE:
        ( A ) NAME/KEY:

(B) LOCATION: 3
                    (C) IDENTIFICATION METHOD:
                    (D) OTHER INFORMATION: /note="MeVal"

(ix) FEATURE:
                    (A) NAME/KEY:
                    (B) LOCATION: 5
                    (C) IDENTIFICATION METHOD:
                    (D) OTHER INFORMATION: /note="MePhe"

(ix) FEATURE:
                    (A) NAME/KEY:
                    (B) LOCATION: 6
                    (C) IDENTIFICATION METHOD:
                    (D) OTHER INFORMATION: /note="Pro-OPac"

(xi) SEQUENCE DESCRIPTION: SEQ ID NO:14:

Xaa  Xaa  Xaa  Phe  Xaa  Xaa
 1                    5

(2) INFORMATION FOR SEQ ID NO:15:

(i) SEQUENCE CHARACTERISTICS:
                (A) LENGTH: 8 amino acids
                (B) TYPE: amino acid
                (C) STRANDEDNESS: single
                (D) TOPOLOGY: linear (ii) MOLECULE TYPE: peptide (ix) FEATURE:
                    (A) NAME/KEY:
                    (B) LOCATION: 1
                    (C) IDENTIFICATION METHOD:
                    (D) OTHER INFORMATION: /note="Boc-aIle"

(ix) FEATURE:
                    (A) NAME/KEY:
                    (B) LOCATION: 2
                    (C) IDENTIFICATION METHOD:
                    (D) OTHER INFORMATION: /note="MeVal"

(ix) FEATURE:
                    (A) NAME/KEY:
                    (B) LOCATION: 4
                    (C) IDENTIFICATION METHOD:
                    (D) OTHER INFORMATION: /note="MeThr(Bzl)-D-Hmp, the
                        carboxyl group of D-Hmp being bound to the amino acid
                        in location 5."

(ix) FEATURE:
                    (A) NAME/KEY:
                    (B) LOCATION: 5
                    (C) IDENTIFICATION METHOD:
                    (D) OTHER INFORMATION: /note="MeVal"

(ix) FEATURE:
                    (A) NAME/KEY:
                    (B) LOCATION: 7
                    (C) IDENTIFICATION METHOD:
                    (D) OTHER INFORMATION: /note="MePhe"

(ix) FEATURE:
                    (A) NAME/KEY:
                    (B) LOCATION: 8
                    (C) IDENTIFICATION METHOD:
                    (D) OTHER INFORMATION: /note="Pro-OPac"

(xi) SEQUENCE DESCRIPTION: SEQ ID NO:15:

Xaa  Xaa  Leu  Xaa  Xaa  Phe  Xaa  Xaa
 1                    5

(2) INFORMATION FOR SEQ ID NO:16:

-continued

```
        ( i ) SEQUENCE CHARACTERISTICS:
                ( A ) LENGTH: 8 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY:
                ( B ) LOCATION: 1
                ( C ) IDENTIFICATION METHOD:
                ( D ) OTHER INFORMATION: /note="Boc-aIle"

( i x ) FEATURE:
                ( A ) NAME/KEY:
                ( B ) LOCATION: 2
                ( C ) IDENTIFICATION METHOD:
                ( D ) OTHER INFORMATION: /note="MeVal"

( i x ) FEATURE:
                ( A ) NAME/KEY:
                ( B ) LOCATION: 4
                ( C ) IDENTIFICATION METHOD:
                ( D ) OTHER INFORMATION: /note="MeThr(Bzl)-D-Hmp, the
                        carboxyl group of D-Hmp being bound to the amino
                        acid in location 5."

( i x ) FEATURE:
                ( A ) NAME/KEY:
                ( B ) LOCATION: 5
                ( C ) IDENTIFICATION METHOD:
                ( D ) OTHER INFORMATION: /note="MeVal"

( i x ) FEATURE:
                ( A ) NAME/KEY:
                ( B ) LOCATION: 7
                ( C ) IDENTIFICATION METHOD:
                ( D ) OTHER INFORMATION: /note="MePhe"

( x i ) SEQUENCE DESCRIPTION: SEQ ID NO:16:

Xaa   Xaa   Leu   Xaa   Xaa   Phe   Xaa   Pro
 1                       5

( 2 ) INFORMATION FOR SEQ ID NO:17:

( i ) SEQUENCE CHARACTERISTICS:
                ( A ) LENGTH: 8 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY:
                ( B ) LOCATION: 1
                ( C ) IDENTIFICATION METHOD:
                ( D ) OTHER INFORMATION: /note="HCl aIle"

( i x ) FEATURE:
                ( A ) NAME/KEY:
                ( B ) LOCATION: 2
                ( C ) IDENTIFICATION METHOD:
                ( D ) OTHER INFORMATION: /note="MeVal"

( i x ) FEATURE:
                ( A ) NAME/KEY:
                ( B ) LOCATION: 4
                ( C ) IDENTIFICATION METHOD:
                ( D ) OTHER INFORMATION: /note="MeThr(Bzl)-D-Hmp, the
                        carboxyl group of D-Hmp being bound to the amino
                        acid in location 5."

( i x ) FEATURE:
                ( A ) NAME/KEY:
```

(B) LOCATION: 5
(C) IDENTIFICATION METHOD:
(D) OTHER INFORMATION: /note="MeVal"

(ix) FEATURE:
(A) NAME/KEY:
(B) LOCATION: 7
(C) IDENTIFICATION METHOD:
(D) OTHER INFORMATION: /note="MePhe"

(xi) SEQUENCE DESCRIPTION: SEQ ID NO:17:

Xaa Xaa Leu Xaa Xaa Phe Xaa Pro
1               5

(2) INFORMATION FOR SEQ ID NO:18:

(i) SEQUENCE CHARACTERISTICS:
(A) LENGTH: 8 amino acids
(B) TYPE: amino acid
(C) STRANDEDNESS: single
(D) TOPOLOGY: circular (ii) MOLECULE TYPE: peptide (ix) FEATURE:
(A) NAME/KEY:
(B) LOCATION: 1
(C) IDENTIFICATION METHOD:
(D) OTHER INFORMATION: /note="aIle"

(ix) FEATURE:
(A) NAME/KEY:
(B) LOCATION: 2
(C) IDENTIFICATION METHOD:
(D) OTHER INFORMATION: /note="MeVal"

(ix) FEATURE:
(A) NAME/KEY:
(B) LOCATION: 4
(C) IDENTIFICATION METHOD:
(D) OTHER INFORMATION: /note="MeThr(Bzl)-D-Hmp, the
carboxyl group of D-Hmp being bound to the amino
acid in location 5."

(ix) FEATURE:
(A) NAME/KEY:
(B) LOCATION: 5
(C) IDENTIFICATION METHOD:
(D) OTHER INFORMATION: /note="MeVal"

(ix) FEATURE:
(A) NAME/KEY:
(B) LOCATION: 7
(C) IDENTIFICATION METHOD:
(D) OTHER INFORMATION: /note="MePhe"

(ix) FEATURE:
(A) NAME/KEY:
(B) LOCATION: 8
(C) IDENTIFICATION METHOD:
(D) OTHER INFORMATION: /note="Pro, being bound to the amino
acid in location 1."

(xi) SEQUENCE DESCRIPTION: SEQ ID NO:18:

Xaa Xaa Leu Xaa Xaa Phe Xaa Pro
1               5

(2) INFORMATION FOR SEQ ID NO:19:

(i) SEQUENCE CHARACTERISTICS:
(A) LENGTH: 8 amino acids
(B) TYPE: amino acid
(C) STRANDEDNESS: single
(D) TOPOLOGY: circular ( i i ) MOLECULE TYPE: peptide ( i x ) FEATURE:
    ( A ) NAME/KEY:
    ( B ) LOCATION: 1
    ( C ) IDENTIFICATION METHOD:
    ( D ) OTHER INFORMATION: /note="aIle"

( i x ) FEATURE:
    ( A ) NAME/KEY:
    ( B ) LOCATION: 2
    ( C ) IDENTIFICATION METHOD:
    ( D ) OTHER INFORMATION: /note="MeVal"

( i x ) FEATURE:
    ( A ) NAME/KEY:
    ( B ) LOCATION: 4
    ( C ) IDENTIFICATION METHOD:
    ( D ) OTHER INFORMATION: /note="MeThr(Bzl)-D-Hmp, the carboxyl group of D-Hmp being bound to the amino acid in location 5."

( i x ) FEATURE:
    ( A ) NAME/KEY:
    ( B ) LOCATION: 5
    ( C ) IDENTIFICATION METHOD:
    ( D ) OTHER INFORMATION: /note="MeVal"

( i x ) FEATURE:
    ( A ) NAME/KEY:
    ( B ) LOCATION: 7
    ( C ) IDENTIFICATION METHOD:
    ( D ) OTHER INFORMATION: /note="MePhe"

( i x ) FEATURE:
    ( A ) NAME/KEY:
    ( B ) LOCATION: 8
    ( C ) IDENTIFICATION METHOD:
    ( D ) OTHER INFORMATION: /note="Pro, this amino acid being bound to the amino acid in location 1."

( x i ) SEQUENCE DESCRIPTION: SEQ ID NO:19:

Xaa Xaa Leu Xaa Xaa Phe Xaa Pro
1                      5

( 2 ) INFORMATION FOR SEQ ID NO:20:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: circular ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note="aIle"

( i x ) FEATURE:
        ( A ) NAME/KEY:
        ( B ) LOCATION: 2
        ( C ) IDENTIFICATION METHOD:
        ( D ) OTHER INFORMATION: /note="MeVal"

( i x ) FEATURE:
        ( A ) NAME/KEY:
        ( B ) LOCATION: 3
        ( C ) IDENTIFICATION METHOD:
        ( D ) OTHER INFORMATION: /note="aIle"

( i x ) FEATURE:
        ( A ) NAME/KEY:

-continued (B) LOCATION: 4
                    (C) IDENTIFICATION METHOD:
                    (D) OTHER INFORMATION: /note="beta-HOMeVal-D-Hmp, the
                        carboxyl group of D-Hmp being bound to the amino
                        acid in location 5."

(ix) FEATURE:
                    (A) NAME/KEY:
                    (B) LOCATION: 5
                    (C) IDENTIFICATION METHOD:
                    (D) OTHER INFORMATION: /note="MeVal"

(ix) FEATURE:
                    (A) NAME/KEY:
                    (B) LOCATION: 7
                    (C) IDENTIFICATION METHOD:
                    (D) OTHER INFORMATION: /note="MePhe"

(ix) FEATURE:
                    (A) NAME/KEY:
                    (B) LOCATION: 8
                    (C) IDENTIFICATION METHOD:
                    (D) OTHER INFORMATION: /note="Pro, this amino acid being
                        bound to the amino acid in location 1."

(xi) SEQUENCE DESCRIPTION: SEQ ID NO:20:

Xaa  Xaa  Xaa  Xaa  Xaa  Phe  Xaa  Pro
 1                    5

(2) INFORMATION FOR SEQ ID NO:21:

(i) SEQUENCE CHARACTERISTICS:
                    (A) LENGTH: 8 amino acids
                    (B) TYPE: amino acid
                    (C) STRANDEDNESS: single
                    (D) TOPOLOGY: linear (ii) MOLECULE TYPE: peptide (ix) FEATURE:
                    (A) NAME/KEY:
                    (B) LOCATION: 1
                    (C) IDENTIFICATION METHOD:
                    (D) OTHER INFORMATION: /note="Glu, its amino group having
                        as a substituent Boc group and its gamma-carboxyl group
                        having as a substituent Bzl group [Boc-Glu(OBzl)]."

(ix) FEATURE:
                    (A) NAME/KEY:
                    (B) LOCATION: 2
                    (C) IDENTIFICATION METHOD:
                    (D) OTHER INFORMATION: /note="MeVal"

(ix) FEATURE:
                    (A) NAME/KEY:
                    (B) LOCATION: 4
                    (C) IDENTIFICATION METHOD:
                    (D) OTHER INFORMATION: /note="beta-HOMeVal-D-Hmp, the
                        carboxyl group of D-Hmp being bound to the amino
                        acid in location 5."

(ix) FEATURE:
                    (A) NAME/KEY:
                    (B) LOCATION: 5
                    (C) IDENTIFICATION METHOD:
                    (D) OTHER INFORMATION: /note="MeVal"

(ix) FEATURE:
                    (A) NAME/KEY:
                    (B) LOCATION: 7
                    (C) IDENTIFICATION METHOD:
                    (D) OTHER INFORMATION: /note="MePhe"

(ix) FEATURE:
                    (A) NAME/KEY:
                    (B) LOCATION: 8

-continued (C) IDENTIFICATION METHOD:
(D) OTHER INFORMATION: /note="Pro-OPac"

(xi) SEQUENCE DESCRIPTION: SEQ ID NO:21:

Xaa Xaa Leu Xaa Xaa Phe Xaa Xaa
1                 5

(2) INFORMATION FOR SEQ ID NO:22:

(i) SEQUENCE CHARACTERISTICS:
   (A) LENGTH: 8 amino acids
   (B) TYPE: amino acid
   (C) STRANDEDNESS: single
   (D) TOPOLOGY: linear (ii) MOLECULE TYPE: peptide (ix) FEATURE:
   (A) NAME/KEY:
   (B) LOCATION: 1
   (C) IDENTIFICATION METHOD:
   (D) OTHER INFORMATION: /note="Boc-Glu(OBzl)"

(ix) FEATURE:
   (A) NAME/KEY:
   (B) LOCATION: 2
   (C) IDENTIFICATION METHOD:
   (D) OTHER INFORMATION: /note="MeVal"

(ix) FEATURE:
   (A) NAME/KEY:
   (B) LOCATION: 4
   (C) IDENTIFICATION METHOD:
   (D) OTHER INFORMATION: /note="beta-HOMeVal-D-Hmp, the
         carboxyl group of D-Hmp being bound to the amino
         acid in location 5."

(ix) FEATURE:
   (A) NAME/KEY:
   (B) LOCATION: 5
   (C) IDENTIFICATION METHOD:
   (D) OTHER INFORMATION: /note="MeVal"

(ix) FEATURE:
   (A) NAME/KEY:
   (B) LOCATION: 7
   (C) IDENTIFICATION METHOD:
   (D) OTHER INFORMATION: /note="MePhe"

(xi) SEQUENCE DESCRIPTION: SEQ ID NO:22:

Xaa Xaa Leu Xaa Xaa Phe Xaa Pro
1                 5

(2) INFORMATION FOR SEQ ID NO:23:

(i) SEQUENCE CHARACTERISTICS:
   (A) LENGTH: 8 amino acids
   (B) TYPE: amino acid
   (C) STRANDEDNESS: single
   (D) TOPOLOGY: linear (ii) MOLECULE TYPE: peptide (ix) FEATURE:
   (A) NAME/KEY:
   (B) LOCATION: 1
   (C) IDENTIFICATION METHOD:
   (D) OTHER INFORMATION: /note="HCl Glu, its gamma-
         carboxyl group of D-Hmp being bound to the amino
         acid in location 5."

(ix) FEATURE:
   (A) NAME/KEY:
   (B) LOCATION: 2

( C ) IDENTIFICATION METHOD:
                ( D ) OTHER INFORMATION: /note="MeVal"

( i x ) FEATURE:
                ( A ) NAME/KEY:
                ( B ) LOCATION: 4
                ( C ) IDENTIFICATION METHOD:
                ( D ) OTHER INFORMATION: /note="beta-HOMeVal-D-Hmp, the
                        carboxyl group of D-Hmp being bound to the amino
                        acid in location 5."

( i x ) FEATURE:
                ( A ) NAME/KEY:
                ( B ) LOCATION: 5
                ( C ) IDENTIFICATION METHOD:
                ( D ) OTHER INFORMATION: /note="MeVal"

( i x ) FEATURE:
                ( A ) NAME/KEY:
                ( B ) LOCATION: 7
                ( C ) IDENTIFICATION METHOD:
                ( D ) OTHER INFORMATION: /note="MePhe"

( x i ) SEQUENCE DESCRIPTION: SEQ ID NO:23:

Xaa  Xaa  Leu  Xaa  Xaa  Phe  Xaa  Pro
 1                 5

( 2 ) INFORMATION FOR SEQ ID NO:24:

( i ) SEQUENCE CHARACTERISTICS:
                ( A ) LENGTH: 8 amino acids
                ( B ) TYPE: amino acid
                ( C ) STRANDEDNESS: single
                ( D ) TOPOLOGY: circular ( i i ) MOLECULE TYPE: peptide ( i x ) FEATURE:
                ( A ) NAME/KEY:
                ( B ) LOCATION: 1
                ( C ) IDENTIFICATION METHOD:
                ( D ) OTHER INFORMATION: /note="Glu, its gamma-carboxyl group
                        being protected by Bzl group [Glu(OBzl)]."

( i x ) FEATURE:
                ( A ) NAME/KEY:
                ( B ) LOCATION: 2
                ( C ) IDENTIFICATION METHOD:
                ( D ) OTHER INFORMATION: /note="MeVal"

( i x ) FEATURE:
                ( A ) NAME/KEY:
                ( B ) LOCATION: 4
                ( C ) IDENTIFICATION METHOD:
                ( D ) OTHER INFORMATION: /note="beta-HOMeVal-D-Hmp, the
                        carboxyl group of D-Hmp being bound to the amino
                        acid in location 5."

( i x ) FEATURE:
                ( A ) NAME/KEY:
                ( B ) LOCATION: 5
                ( C ) IDENTIFICATION METHOD:
                ( D ) OTHER INFORMATION: /note="MeVal"

( i x ) FEATURE:
                ( A ) NAME/KEY:
                ( B ) LOCATION: 7
                ( C ) IDENTIFICATION METHOD:
                ( D ) OTHER INFORMATION: /note="MePhe"

( i x ) FEATURE:
                ( A ) NAME/KEY:
                ( B ) LOCATION: 8
                ( C ) IDENTIFICATION METHOD:
                ( D ) OTHER INFORMATION: /note="Pro, this amino acid being
                        bound to the amino acid in location 1."

( x i ) SEQUENCE DESCRIPTION: SEQ ID NO:24:

Xaa Xaa Leu Xaa Xaa Phe Xaa Pro
1               5

( 2 ) INFORMATION FOR SEQ ID NO:25:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY:
    ( B ) LOCATION: 1
    ( C ) IDENTIFICATION METHOD:
    ( D ) OTHER INFORMATION: /note="Boc-aIle"

( i x ) FEATURE:
    ( A ) NAME/KEY:
    ( B ) LOCATION: 2
    ( C ) IDENTIFICATION METHOD:
    ( D ) OTHER INFORMATION: /note="5-benzyloxy-N-methylnorvaline
    ( R O M e N v a ), R meaning Bzl group."

( i x ) FEATURE:
    ( A ) NAME/KEY:
    ( B ) LOCATION: 4
    ( C ) IDENTIFICATION METHOD:
    ( D ) OTHER INFORMATION: /note="beta-HOMeVal-D-Hmp, the
      carboxyl group of D-Hmp being bound to the amino
      acid in location 5."

( i x ) FEATURE:
    ( A ) NAME/KEY:
    ( B ) LOCATION: 5
    ( C ) IDENTIFICATION METHOD:
    ( D ) OTHER INFORMATION: /note="MeVal"

( i x ) FEATURE:
    ( A ) NAME/KEY:
    ( B ) LOCATION: 7
    ( C ) IDENTIFICATION METHOD:
    ( D ) OTHER INFORMATION: /note="MePhe"

( i x ) FEATURE:
    ( A ) NAME/KEY:
    ( B ) LOCATION: 8
    ( C ) IDENTIFICATION METHOD:
    ( D ) OTHER INFORMATION: /note="Pro-OPac"

( x i ) SEQUENCE DESCRIPTION: SEQ ID NO:25:

Xaa Xaa Leu Xaa Xaa Phe Xaa Xaa
1               5

( 2 ) INFORMATION FOR SEQ ID NO:26:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY:
    ( B ) LOCATION: 1
    ( C ) IDENTIFICATION METHOD:
    ( D ) OTHER INFORMATION: /note="Boc-aIle"

( i x ) FEATURE:
        ( A ) NAME/KEY:
        ( B ) LOCATION: 2
        ( C ) IDENTIFICATION METHOD:
        ( D ) OTHER INFORMATION: /note="ROMeNva, R meaning Bzl group."

( i x ) FEATURE:
        ( A ) NAME/KEY:
        ( B ) LOCATION: 4
        ( C ) IDENTIFICATION METHOD:
        ( D ) OTHER INFORMATION: /note="beta-HOMeVal-D-Hmp, the carboxyl group of D-Hmp being bound to the amino acid in location 5."

( i x ) FEATURE:
        ( A ) NAME/KEY:
        ( B ) LOCATION: 5
        ( C ) IDENTIFICATION METHOD:
        ( D ) OTHER INFORMATION: /note="MeVal"

( i x ) FEATURE:
        ( A ) NAME/KEY:
        ( B ) LOCATION: 7
        ( C ) IDENTIFICATION METHOD:
        ( D ) OTHER INFORMATION: /note="MePhe"

( x i ) SEQUENCE DESCRIPTION: SEQ ID NO:26:

Xaa Xaa Leu Xaa Xaa Phe Xaa Pro
1                   5

( 2 ) INFORMATION FOR SEQ ID NO:27:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note="HCl alle"

( i x ) FEATURE:
        ( A ) NAME/KEY:
        ( B ) LOCATION: 2
        ( C ) IDENTIFICATION METHOD:
        ( D ) OTHER INFORMATION: /note="ROMeNva, R meaning Bzl group."

( i x ) FEATURE:
        ( A ) NAME/KEY:
        ( B ) LOCATION: 4
        ( C ) IDENTIFICATION METHOD:
        ( D ) OTHER INFORMATION: /note="beta-HOMeVal-D-Hmp, the carboxyl group of D-Hmp being bound to the amino acid in location 5."

( i x ) FEATURE:
        ( A ) NAME/KEY:
        ( B ) LOCATION: 5
        ( C ) IDENTIFICATION METHOD:
        ( D ) OTHER INFORMATION: /note="MeVal"

( i x ) FEATURE:
        ( A ) NAME/KEY:
        ( B ) LOCATION: 7
        ( C ) IDENTIFICATION METHOD:
        ( D ) OTHER INFORMATION: /note="MePhe"

( x i ) SEQUENCE DESCRIPTION: SEQ ID NO:27:

Xaa Xaa Leu Xaa Xaa Phe Xaa Pro
1                   5

( 2 ) INFORMATION FOR SEQ ID NO:28:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: circular ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note="aIle"

( i x ) FEATURE:
        ( A ) NAME/KEY:
        ( B ) LOCATION: 2
        ( C ) IDENTIFICATION METHOD:
        ( D ) OTHER INFORMATION: /note="ROMeNva, R meaning Bzl group."

( i x ) FEATURE:
        ( A ) NAME/KEY:
        ( B ) LOCATION: 4
        ( C ) IDENTIFICATION METHOD:
        ( D ) OTHER INFORMATION: /note="beta-HOMeVal-D-Hmp, the
            carboxyl group of D-Hmp being bound to the amino
            acid in location 5."

( i x ) FEATURE:
        ( A ) NAME/KEY:
        ( B ) LOCATION: 5
        ( C ) IDENTIFICATION METHOD:
        ( D ) OTHER INFORMATION: /note="MeVal"

( i x ) FEATURE:
        ( A ) NAME/KEY:
        ( B ) LOCATION: 7
        ( C ) IDENTIFICATION METHOD:
        ( D ) OTHER INFORMATION: /note="MePhe"

( i x ) FEATURE:
        ( A ) NAME/KEY:
        ( B ) LOCATION: 8
        ( C ) IDENTIFICATION METHOD:
        ( D ) OTHER INFORMATION: /note="Pro, this amino acid being
            bound to the amino acid in location 1."

( x i ) SEQUENCE DESCRIPTION: SEQ ID NO:28:

```
Xaa  Xaa  Leu  Xaa  Xaa  Phe  Xaa  Pro
 1                  5
```

( 2 ) INFORMATION FOR SEQ ID NO:29:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: circular ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note="aIle"

( i x ) FEATURE:
        ( A ) NAME/KEY:
        ( B ) LOCATION: 2
        ( C ) IDENTIFICATION METHOD:
        ( D ) OTHER INFORMATION: /note="5-hydroxy-N-methylnorvaline (HOMeNva)"

(ix) FEATURE:
    (A) NAME/KEY:
    (B) LOCATION: 4
    (C) IDENTIFICATION METHOD:
    (D) OTHER INFORMATION: /note="beta-HOMeVal-D-Hmp, the carboxyl group of D-Hmp being bound to the amino acid in location 5."

(ix) FEATURE:
    (A) NAME/KEY:
    (B) LOCATION: 5
    (C) IDENTIFICATION METHOD:
    (D) OTHER INFORMATION: /note="MeVal"

(ix) FEATURE:
    (A) NAME/KEY:
    (B) LOCATION: 7
    (C) IDENTIFICATION METHOD:
    (D) OTHER INFORMATION: /note="MePhe"

(ix) FEATURE:
    (A) NAME/KEY:
    (B) LOCATION: 8
    (C) IDENTIFICATION METHOD:
    (D) OTHER INFORMATION: /note="Pro, this amino acid being bound to the amino acid in location 1."

(xi) SEQUENCE DESCRIPTION: SEQ ID NO:29:

Xaa  Xaa  Leu  Xaa  Xaa  Phe  Xaa  Pro
1                   5

(2) INFORMATION FOR SEQ ID NO:30:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (B) LOCATION: 1
        (C) IDENTIFICATION METHOD:
        (D) OTHER INFORMATION: /note="aIle, its amino group having substituent Boc group and its carboxyl group having substituent (2S)-hydroxy-3-methylbutanoic acid (L-Hmb) to form ester bond (Boc-aIle-L-Hmb), the carboxyl group of L-Hmb bound to location 2."

(ix) FEATURE:
        (A) NAME/KEY:
        (B) LOCATION: 3
        (C) IDENTIFICATION METHOD:
        (D) OTHER INFORMATION: /note="beta-HOMeVal-D-Hmp, the carboxyl group of D-Hmp being bound to the amino acid in location 4."

(ix) FEATURE:
        (A) NAME/KEY:
        (B) LOCATION: 4
        (C) IDENTIFICATION METHOD:
        (D) OTHER INFORMATION: /note="MeVal"

(ix) FEATURE:
        (A) NAME/KEY:
        (B) LOCATION: 6
        (C) IDENTIFICATION METHOD:
        (D) OTHER INFORMATION: /note="MePhe"

(ix) FEATURE:
        (A) NAME/KEY:
        (B) LOCATION: 7

( C ) IDENTIFICATION METHOD:
                    ( D ) OTHER INFORMATION: /note="Pro-OPac"

( x i ) SEQUENCE DESCRIPTION: SEQ ID NO:30:

Xaa  Leu  Xaa  Xaa  Phe  Xaa  Xaa
 1                    5

( 2 ) INFORMATION FOR SEQ ID NO:31:

( i ) SEQUENCE CHARACTERISTICS:
                    ( A ) LENGTH: 7 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY:
                    ( B ) LOCATION: 1
                    ( C ) IDENTIFICATION METHOD:
                    ( D ) OTHER INFORMATION: /note="Boc-alle-L-Hmb, the carboxyl
                            group of L- Hmb being bound to the amino acid in
                            location 2."

( i x ) FEATURE:
                    ( A ) NAME/KEY:
                    ( B ) LOCATION: 3
                    ( C ) IDENTIFICATION METHOD:
                    ( D ) OTHER INFORMATION: /note="beta-HOMeVal-D-Hmp, the
                            carboxyl group of D-Hmp being bound to the amino acid in
                            location 4."

( i x ) FEATURE:
                    ( A ) NAME/KEY:
                    ( B ) LOCATION: 4
                    ( C ) IDENTIFICATION METHOD:
                    ( D ) OTHER INFORMATION: /note="MeVal"

( i x ) FEATURE:
                    ( A ) NAME/KEY:
                    ( B ) LOCATION: 6
                    ( C ) IDENTIFICATION METHOD:
                    ( D ) OTHER INFORMATION: /note="MePhe"

( x i ) SEQUENCE DESCRIPTION: SEQ ID NO:31:

Xaa  Leu  Xaa  Xaa  Phe  Xaa  Pro
 1                    5

( 2 ) INFORMATION FOR SEQ ID NO:32:

( i ) SEQUENCE CHARACTERISTICS:
                    ( A ) LENGTH: 7 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY:
                    ( B ) LOCATION: 1
                    ( C ) IDENTIFICATION METHOD:
                    ( D ) OTHER INFORMATION: /note="HCl alle, its carboxyl group
                            having a substituent L-Hmb and the carboxyl group of
                            L-Hmb being bound to the amino acid in location 2."

( i x ) FEATURE:
                    ( A ) NAME/KEY:
                    ( B ) LOCATION: 3
                    ( C ) IDENTIFICATION METHOD:
                    ( D ) OTHER INFORMATION: /note="beta-HOMeVal-D-Hmp, the
                            carboxyl group of D-Hmp being bound to the amino acid
                            in location 4."

( i x ) FEATURE:
    ( A ) NAME/KEY:
    ( B ) LOCATION: 4
    ( C ) IDENTIFICATION METHOD:
    ( D ) OTHER INFORMATION: /note="MeVal"

( i x ) FEATURE:
    ( A ) NAME/KEY:
    ( B ) LOCATION: 6
    ( C ) IDENTIFICATION METHOD:
    ( D ) OTHER INFORMATION: /note="MePhe"

( x i ) SEQUENCE DESCRIPTION: SEQ ID NO:32:

Xaa Leu Xaa Xaa Phe Xaa Pro
1               5

( 2 ) INFORMATION FOR SEQ ID NO:33:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: circular ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note="aIle, its carboxyl group
            having substituent L-Hmb and the carboxyl group of L-Hmb
            being bound to the amino acid in location 2."

( i x ) FEATURE:
        ( A ) NAME/KEY:
        ( B ) LOCATION: 3
        ( C ) IDENTIFICATION METHOD:
        ( D ) OTHER INFORMATION: /note="beta-HOMeVal-D-Hmp, the
            carboxyl group of D-Hmp being bound to the amino acid
            in location 4."

( i x ) FEATURE:
        ( A ) NAME/KEY:
        ( B ) LOCATION: 4
        ( C ) IDENTIFICATION METHOD:
        ( D ) OTHER INFORMATION: /note="MeVal"

( i x ) FEATURE:
        ( A ) NAME/KEY:
        ( B ) LOCATION: 6
        ( C ) IDENTIFICATION METHOD:
        ( D ) OTHER INFORMATION: /note="MePhe"

( i x ) FEATURE: 7
        ( A ) NAME/KEY:
        ( B ) LOCATION:
        ( C ) IDENTIFICATION METHOD:
        ( D ) OTHER INFORMATION: /note="Pro, this amino acid being
            bound to the amino acid in location 1."

( x i ) SEQUENCE DESCRIPTION: SEQ ID NO:33:

Xaa Leu Xaa Xaa Phe Xaa Pro
1               5

( 2 ) INFORMATION FOR SEQ ID NO:34:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: circular (ii) MOLECULE TYPE: peptide (ix) FEATURE:
    (A) NAME/KEY:
    (B) LOCATION: 1
    (C) IDENTIFICATION METHOD:
    (D) OTHER INFORMATION: /note="aIle"

(ix) FEATURE:
    (A) NAME/KEY:
    (B) LOCATION: 2
    (C) IDENTIFICATION METHOD:
    (D) OTHER INFORMATION: /note="MeVal"

(ix) FEATURE:
    (A) NAME/KEY:
    (B) LOCATION: 4
    (C) IDENTIFICATION METHOD:
    (D) OTHER INFORMATION: /note="beta-HOMeVal, its carboxyl
        group having a substituent (2R)-hydroxy-(3S)-methyl-
        pentanoic acid [(2R,3S)-Hmp]to form ester bond [beta-
        HOMeVal-(2R, 3S)-Hmp], the carboxyl group of (2R, 3S)-Hmp
        bound to location 5."

(ix) FEATURE:
    (A) NAME/KEY:
    (B) LOCATION: 5
    (C) IDENTIFICATION METHOD:
    (D) OTHER INFORMATION: /note="MeVal"

(ix) FEATURE:
    (A) NAME/KEY:
    (B) LOCATION: 7
    (C) IDENTIFICATION METHOD:
    (D) OTHER INFORMATION: /note="MePhe"

(xi) SEQUENCE DESCRIPTION: SEQ ID NO:34:

Xaa Xaa Leu Xaa Xaa Phe Xaa Pro
1                      5

(2) INFORMATION FOR SEQ ID NO:35:

(i) SEQUENCE CHARACTERISTICS:
        (A) LENGTH: 8 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY:
        (B) LOCATION: 1
        (C) IDENTIFICATION METHOD:
        (D) OTHER INFORMATION: /note="aIle"

(ix) FEATURE:
        (A) NAME/KEY:
        (B) LOCATION: 2
        (C) IDENTIFICATION METHOD:
        (D) OTHER INFORMATION: /note="N-methyl-allo-isoleucine
            (MeaIle)"

(ix) FEATURE:
        (A) NAME/KEY:
        (B) LOCATION: 4
        (C) IDENTIFICATION METHOD:
        (D) OTHER INFORMATION: /note="beta-HOMeVal-D-Hmp, the
            carboxyl group of D-Hmp being bound to the amino acid
            in location 5."

(ix) FEATURE:
        (A) NAME/KEY:
        (B) LOCATION: 5
        (C) IDENTIFICATION METHOD:
        (D) OTHER INFORMATION: /note="MeVal"

( i x ) FEATURE:
    ( A ) NAME/KEY:
    ( B ) LOCATION: 7
    ( C ) IDENTIFICATION METHOD:
    ( D ) OTHER INFORMATION: /note="MePhe"

( i x ) FEATURE:
    ( A ) NAME/KEY:
    ( B ) LOCATION: 8
    ( C ) IDENTIFICATION METHOD:
    ( D ) OTHER INFORMATION: /note="Pro, this amino acid being bound to the amino acid in location 1."

( x i ) SEQUENCE DESCRIPTION: SEQ ID NO:35:

Xaa Xaa Leu Xaa Xaa Phe Xaa Pro
1               5

( 2 ) INFORMATION FOR SEQ ID NO:36:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: circular ( i i ) MOLECULE TYPE: peptide ( i x ) FEATURE:
    ( A ) NAME/KEY:
    ( B ) LOCATION: 1
    ( C ) IDENTIFICATION METHOD:
    ( D ) OTHER INFORMATION: /note="aIle"

( i x ) FEATURE:
    ( A ) NAME/KEY:
    ( B ) LOCATION: 2
    ( C ) IDENTIFICATION METHOD:
    ( D ) OTHER INFORMATION: /note="N-methylleucine (MeLeu)"

( i x ) FEATURE:
    ( A ) NAME/KEY:
    ( B ) LOCATION: 4
    ( C ) IDENTIFICATION METHOD:
    ( D ) OTHER INFORMATION: /note="beta-HOMeVal-D-Hmp, the carboxyl group of D-Hmp being bound to the amino acid in location 5."

( i x ) FEATURE:
    ( A ) NAME/KEY:
    ( B ) LOCATION: 5
    ( C ) IDENTIFICATION METHOD:
    ( D ) OTHER INFORMATION: /note="MeVal"

( i x ) FEATURE:
    ( A ) NAME/KEY:
    ( B ) LOCATION: 7
    ( C ) IDENTIFICATION METHOD:
    ( D ) OTHER INFORMATION: /note="MePhe"

( i x ) FEATURE:
    ( A ) NAME/KEY:
    ( B ) LOCATION: 8
    ( C ) IDENTIFICATION METHOD:
    ( D ) OTHER INFORMATION: /note="Pro, this amino acid being bound to the amino acid in location 1."

( x i ) SEQUENCE DESCRIPTION: SEQ ID NO:36:

Xaa Xaa Leu Xaa Xaa Phe Xaa Pro
1               5

( 2 ) INFORMATION FOR SEQ ID NO:37:

( i ) SEQUENCE CHARACTERISTICS:

-continued ( A ) LENGTH: 8 amino acids
                    ( B ) TYPE: amino acid
                    ( C ) STRANDEDNESS: single
                    ( D ) TOPOLOGY: circular ( i i ) MOLECULE TYPE: peptide ( i x ) FEATURE:
                    ( A ) NAME/KEY:
                    ( B ) LOCATION: 2
                    ( C ) IDENTIFICATION METHOD:
                    ( D ) OTHER INFORMATION: /note="MeVal"

( i x ) FEATURE:
                    ( A ) NAME/KEY:
                    ( B ) LOCATION: 4
                    ( C ) IDENTIFICATION METHOD:
                    ( D ) OTHER INFORMATION: /note="beta-HOMeVal-D-Hmp, the
                            carboxyl group of D-Hmp being bound to the amino acid
                            in location 5."

( i x ) FEATURE:
                    ( A ) NAME/KEY:
                    ( B ) LOCATION: 5
                    ( C ) IDENTIFICATION METHOD:
                    ( D ) OTHER INFORMATION: /note="MeVal"

( i x ) FEATURE:
                    ( A ) NAME/KEY:
                    ( B ) LOCATION: 7
                    ( C ) IDENTIFICATION METHOD:
                    ( D ) OTHER INFORMATION: /note="MePhe"

( i x ) FEATURE:
                    ( A ) NAME/KEY:
                    ( B ) LOCATION: 8
                    ( C ) IDENTIFICATION METHOD:
                    ( D ) OTHER INFORMATION: /note="Pro, this amino acid being
                            bound to the amino acid in location 1."

( x i ) SEQUENCE DESCRIPTION: SEQ ID NO:37:

Glu  Xaa  Leu  Xaa  Xaa  Phe  Xaa  Pro
 1                    5

( 2 ) INFORMATION FOR SEQ ID NO:38:

( i ) SEQUENCE CHARACTERISTICS:
                    ( A ) LENGTH: 8 amino acids
                    ( B ) TYPE: amino acid
                    ( C ) STRANDEDNESS: single
                    ( D ) TOPOLOGY: circular ( i i ) MOLECULE TYPE: peptide ( i x ) FEATURE:
                    ( A ) NAME/KEY:
                    ( B ) LOCATION: 1
                    ( C ) IDENTIFICATION METHOD:
                    ( D ) OTHER INFORMATION: /note="Glutamic acid gamma-butyl
                            ester (GluOR), R being n-butyl group."

( i x ) FEATURE:
                    ( A ) NAME/KEY:
                    ( B ) LOCATION: 2
                    ( C ) IDENTIFICATION METHOD:
                    ( D ) OTHER INFORMATION: /note="MeVal"

( i x ) FEATURE:
                    ( A ) NAME/KEY:
                    ( B ) LOCATION: 4
                    ( C ) IDENTIFICATION METHOD:
                    ( D ) OTHER INFORMATION: /note="beta-HOMeVal-D-Hmp, the
                            carboxyl group of D-Hmp being bound to the amino acid
                            in location 5."

( i x ) FEATURE:

(A) NAME/KEY:
                (B) LOCATION: 5
                (C) IDENTIFICATION METHOD:
                (D) OTHER INFORMATION: /note="MeVal"

(ix) FEATURE:
                (A) NAME/KEY:
                (B) LOCATION: 7
                (C) IDENTIFICATION METHOD:
                (D) OTHER INFORMATION: /note="MePhe"

(ix) FEATURE:
                (A) NAME/KEY:
                (B) LOCATION: 8
                (C) IDENTIFICATION METHOD:
                (D) OTHER INFORMATION: /note="Pro, this amino acid being
                        bound to the amino acid in location 1."

(xi) SEQUENCE DESCRIPTION: SEQ ID NO:38:

Xaa Xaa Leu Xaa Xaa Phe Xaa Pro
 1                   5

(2) INFORMATION FOR SEQ ID NO:39:

(i) SEQUENCE CHARACTERISTICS:
                (A) LENGTH: 8 amino acids
                (B) TYPE: amino acid
                (C) STRANDEDNESS: single
                (D) TOPOLOGY: circular (ii) MOLECULE TYPE: peptide (ix) FEATURE:
                (A) NAME/KEY:
                (B) LOCATION: 1
                (C) IDENTIFICATION METHOD:
                (D) OTHER INFORMATION: /note="GluOR, R being n-hexyl group."

(ix) FEATURE:
                (A) NAME/KEY:
                (B) LOCATION: 2
                (C) IDENTIFICATION METHOD:
                (D) OTHER INFORMATION: /note="MeVal"

(ix) FEATURE:
                (A) NAME/KEY:
                (B) LOCATION: 4
                (C) IDENTIFICATION METHOD:
                (D) OTHER INFORMATION: /note="beta-HOMeVal-D-Hmp, the
                        carboxyl group of D-Hmp being bound to the amino acid in
                        location 5."

(ix) FEATURE:
                (A) NAME/KEY:
                (B) LOCATION: 5
                (C) IDENTIFICATION METHOD:
                (D) OTHER INFORMATION: /note="MeVal"

(ix) FEATURE:
                (A) NAME/KEY:
                (B) LOCATION: 7
                (C) IDENTIFICATION METHOD:
                (D) OTHER INFORMATION: /note="MePhe"

(ix) FEATURE:
                (A) NAME/KEY:
                (B) LOCATION: 8
                (C) IDENTIFICATION METHOD:
                (D) OTHER INFORMATION: /note="Pro, this amino acid being
                        bound to the amino acid in location 1."

(xi) SEQUENCE DESCRIPTION: SEQ ID NO:39:

Xaa Xaa Leu Xaa Xaa Phe Xaa Pro
 1                   5

( 2 ) INFORMATION FOR SEQ ID NO:40:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: circular ( i i ) MOLECULE TYPE: peptide ( i x ) FEATURE:
  ( A ) NAME/KEY:
  ( B ) LOCATION: 1
  ( C ) IDENTIFICATION METHOD:
  ( D ) OTHER INFORMATION: /note="GluOR, R being n-octyl group."

( i x ) FEATURE:
  ( A ) NAME/KEY:
  ( B ) LOCATION: 2
  ( C ) IDENTIFICATION METHOD:
  ( D ) OTHER INFORMATION: /note="MeVal"

( i x ) FEATURE:
  ( A ) NAME/KEY:
  ( B ) LOCATION: 4
  ( C ) IDENTIFICATION METHOD:
  ( D ) OTHER INFORMATION: /note="beta-HOMeVal-D-Hmp, the carboxyl group of D-Hmp being bound to the amino acid in location 5."

( i x ) FEATURE:
  ( A ) NAME/KEY:
  ( B ) LOCATION: 5
  ( C ) IDENTIFICATION METHOD:
  ( D ) OTHER INFORMATION: /note="MeVal"

( i x ) FEATURE:
  ( A ) NAME/KEY:
  ( B ) LOCATION: 7
  ( C ) IDENTIFICATION METHOD:
  ( D ) OTHER INFORMATION: /note="MePhe"

( i x ) FEATURE:
  ( A ) NAME/KEY:
  ( B ) LOCATION: 8
  ( C ) IDENTIFICATION METHOD:
  ( D ) OTHER INFORMATION: /note="Pro, this amino acid being bound to the amino acid in location 1."

( x i ) SEQUENCE DESCRIPTION: SEQ ID NO:40:

```
Xaa  Xaa  Leu  Xaa  Xaa  Phe  Xaa  Pro
 1                  5
```

( 2 ) INFORMATION FOR SEQ ID NO:41:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: circular ( i i ) MOLECULE TYPE: peptide ( i x ) FEATURE:
  ( A ) NAME/KEY:
  ( B ) LOCATION: 1
  ( C ) IDENTIFICATION METHOD:
  ( D ) OTHER INFORMATION: /note="GluOR, R being n-decyl group."

( i x ) FEATURE:
  ( A ) NAME/KEY:
  ( B ) LOCATION: 2
  ( C ) IDENTIFICATION METHOD:
  ( D ) OTHER INFORMATION: /note="MeVal"

-continued

```
        ( i x ) FEATURE:
                  ( A ) NAME/KEY:
                  ( B ) LOCATION: 4
                  ( C ) IDENTIFICATION METHOD:
                  ( D ) OTHER INFORMATION: /note="beta-HOMeVal-D-Hmp, the
                        carboxyl group of D-Hmp being bound to the amino acid
                        in location 5."

( i x ) FEATURE:
                  ( A ) NAME/KEY:
                  ( B ) LOCATION: 5
                  ( C ) IDENTIFICATION METHOD:
                  ( D ) OTHER INFORMATION: /note="MeVal"

( i x ) FEATURE:
                  ( A ) NAME/KEY:
                  ( B ) LOCATION: 7
                  ( C ) IDENTIFICATION METHOD:
                  ( D ) OTHER INFORMATION: /note="MePhe"

( i x ) FEATURE:
                  ( A ) NAME/KEY:
                  ( B ) LOCATION: 8
                  ( C ) IDENTIFICATION METHOD:
                  ( D ) OTHER INFORMATION: /note="Pro, this amino acid being
                        bound to the amino acid in location 1."

( x i ) SEQUENCE DESCRIPTION: SEQ ID NO:41:

Xaa  Xaa  Leu  Xaa  Xaa  Phe  Xaa  Pro
 1                    5

( 2 ) INFORMATION FOR SEQ ID NO:42:

( i ) SEQUENCE CHARACTERISTICS:
                  ( A ) LENGTH: 8 amino acids
                  ( B ) TYPE: amino acid
                  ( C ) STRANDEDNESS: single
                  ( D ) TOPOLOGY: circular ( i i ) MOLECULE TYPE: peptide ( i x ) FEATURE:
                  ( A ) NAME/KEY:
                  ( B ) LOCATION: 1
                  ( C ) IDENTIFICATION METHOD:
                  ( D ) OTHER INFORMATION: /note= "GluOR, R being cis-3-hexenyl
                        group."

( i x ) FEATURE:
                  ( A ) NAME/KEY:
                  ( B ) LOCATION: 2
                  ( C ) IDENTIFICATION METHOD:
                  ( D ) OTHER INFORMATION: /note="MeVal"

( i x ) FEATURE:
                  ( A ) NAME/KEY:
                  ( B ) LOCATION: 4
                  ( C ) IDENTIFICATION METHOD:
                  ( D ) OTHER INFORMATION: /note="beta-HOMeVal-D-Hmp, the
                        carboxyl group of D-Hmp being bound to the amino acid
                        in location 5."

( i x ) FEATURE:
                  ( A ) NAME/KEY:
                  ( B ) LOCATION: 5
                  ( C ) IDENTIFICATION METHOD:
                  ( D ) OTHER INFORMATION: /note="MeVal"

( i x ) FEATURE:
                  ( A ) NAME/KEY:
                  ( B ) LOCATION: 7
                  ( C ) IDENTIFICATION METHOD:
                  ( D ) OTHER INFORMATION: /note="MePhe"

( i x ) FEATURE:
                  ( A ) NAME/KEY:
```

( B ) LOCATION: 8
              ( C ) IDENTIFICATION METHOD:
              ( D ) OTHER INFORMATION: /note="Pro, this amino acid being
                    bound to the amino acid in location 1."

( x i ) SEQUENCE DESCRIPTION: SEQ ID NO:42:

Xaa  Xaa  Leu  Xaa  Xaa  Phe  Xaa  Pro
 1                    5

( 2 ) INFORMATION FOR SEQ ID NO:43:

( i ) SEQUENCE CHARACTERISTICS:
              ( A ) LENGTH: 8 amino acids
              ( B ) TYPE: amino acid
              ( C ) STRANDEDNESS: single
              ( D ) TOPOLOGY: circular.

( i i ) MOLECULE TYPE: peptide ( i x ) FEATURE:
              ( A ) NAME/KEY:
              ( B ) LOCATION: 1
              ( C ) IDENTIFICATION METHOD:
              ( D ) OTHER INFORMATION: /note= "GluOR, R being trans-3-hexenyl
                    group."

( i x ) FEATURE:
              ( A ) NAME/KEY:
              ( B ) LOCATION: 2
              ( C ) IDENTIFICATION METHOD:
              ( D ) OTHER INFORMATION: /note="MeVal"

( i x ) FEATURE:
              ( A ) NAME/KEY:
              ( B ) LOCATION: 4
              ( C ) IDENTIFICATION METHOD:
              ( D ) OTHER INFORMATION: /note="beta-HOMeVal-D-Hmp, the
                    carboxyl group of D-Hmp being bound to the amino acid
                    in location 5."

( i x ) FEATURE:
              ( A ) NAME/KEY:
              ( B ) LOCATION: 5
              ( C ) IDENTIFICATION METHOD:
              ( D ) OTHER INFORMATION: /note="MeVal"

( i x ) FEATURE:
              ( A ) NAME/KEY:
              ( B ) LOCATION: 7
              ( C ) IDENTIFICATION METHOD:
              ( D ) OTHER INFORMATION: /note="MePhe"

( i x ) FEATURE:
              ( A ) NAME/KEY:
              ( B ) LOCATION: 8
              ( C ) IDENTIFICATION METHOD:
              ( D ) OTHER INFORMATION: /note="Pro, this amino acid being
                    bound to the amino acid in location 1."

( x i ) SEQUENCE DESCRIPTION: SEQ ID NO:43:

Xaa  Xaa  Leu  Xaa  Xaa  Phe  Xaa  Pro
 1                    5

( 2 ) INFORMATION FOR SEQ ID NO:44:

( i ) SEQUENCE CHARACTERISTICS:
              ( A ) LENGTH: 8 amino acids
              ( B ) TYPE: amino acid
              ( C ) STRANDEDNESS: single
              ( D ) TOPOLOGY: circular ( i i ) MOLECULE TYPE: peptide ( i x ) FEATURE:

-continued ( A ) NAME/KEY:
                    ( B ) LOCATION: 1
                    ( C ) IDENTIFICATION METHOD:
                    ( D ) OTHER INFORMATION: /note= "5-hydroxynorvaline (HONva)"

( i x ) FEATURE:
                    ( A ) NAME/KEY:
                    ( B ) LOCATION: 2
                    ( C ) IDENTIFICATION METHOD:
                    ( D ) OTHER INFORMATION: /note="MeVal"

( i x ) FEATURE:
                    ( A ) NAME/KEY:
                    ( B ) LOCATION: 4
                    ( C ) IDENTIFICATION METHOD:
                    ( D ) OTHER INFORMATION: /note="beta-HOMeVal-D-Hmp, the
                            carboxyl group of D-Hmp being bound to the amino acid
                            in location 5."

( i x ) FEATURE:
                    ( A ) NAME/KEY:
                    ( B ) LOCATION: 5
                    ( C ) IDENTIFICATION METHOD:
                    ( D ) OTHER INFORMATION: /note="MeVal"

( i x ) FEATURE:
                    ( A ) NAME/KEY:
                    ( B ) LOCATION: 7
                    ( C ) IDENTIFICATION METHOD:
                    ( D ) OTHER INFORMATION: /note="MePhe"

( i x ) FEATURE:
                    ( A ) NAME/KEY:
                    ( B ) LOCATION: 8
                    ( C ) IDENTIFICATION METHOD:
                    ( D ) OTHER INFORMATION: /note="Pro, this amino acid being
                            bound to the amino acid in location 1."

( x i ) SEQUENCE DESCRIPTION: SEQ ID NO:44:

Xaa  Xaa  Leu  Xaa  Xaa  Phe  Xaa  Pro
 1                    5

( 2 ) INFORMATION FOR SEQ ID NO:45:

( i ) SEQUENCE CHARACTERISTICS:
                    ( A ) LENGTH: 8 amino acids
                    ( B ) TYPE: amino acid
                    ( C ) STRANDEDNESS: single
                    ( D ) TOPOLOGY: circular ( i i ) MOLECULE TYPE: peptide ( i x ) FEATURE:
                    ( A ) NAME/KEY:
                    ( B ) LOCATION: 1
                    ( C ) IDENTIFICATION METHOD:
                    ( D ) OTHER INFORMATION: /note= "5-hexanoyloxynorvaline (RONva),
                            R being n- hexanoyl group."

( i x ) FEATURE:
                    ( A ) NAME/KEY:
                    ( B ) LOCATION: 2
                    ( C ) IDENTIFICATION METHOD:
                    ( D ) OTHER INFORMATION: /note="MeVal"

( i x ) FEATURE:
                    ( A ) NAME/KEY:
                    ( B ) LOCATION: 4
                    ( C ) IDENTIFICATION METHOD:
                    ( D ) OTHER INFORMATION: /note="beta-HOMeVal-D-Hmp, the
                            carboxyl group of D-Hmp being bound to the amino acid
                            in location 5."

( i x ) FEATURE:
                    ( A ) NAME/KEY:
                    ( B ) LOCATION: 5

-continued ( C ) IDENTIFICATION METHOD:
                ( D ) OTHER INFORMATION: /note="MeVal"

( i x ) FEATURE:
                ( A ) NAME/KEY:
                ( B ) LOCATION: 7
                ( C ) IDENTIFICATION METHOD:
                ( D ) OTHER INFORMATION: /note="MePhe"

( i x ) FEATURE:
                ( A ) NAME/KEY:
                ( B ) LOCATION: 8
                ( C ) IDENTIFICATION METHOD:
                ( D ) OTHER INFORMATION: /note="Pro, this amino acid being
                        bound to the amino acid in location 1."

( x i ) SEQUENCE DESCRIPTION: SEQ ID NO:45:

Xaa  Xaa  Leu  Xaa  Xaa  Phe  Xaa  Pro
1                      5

( 2 ) INFORMATION FOR SEQ ID NO:46:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY:
                ( B ) LOCATION: 1
                ( C ) IDENTIFICATION METHOD:
                ( D ) OTHER INFORMATION: /note= "Glu, its amino group having a
                        substituent Boc group and its gamma-carboxyl group being
                        protected by cyclohexyl group (cHex). [Boc-Glu(OcHex)]"

( i x ) FEATURE:
                ( A ) NAME/KEY:
                ( B ) LOCATION: 2
                ( C ) IDENTIFICATION METHOD:
                ( D ) OTHER INFORMATION: /note="beta-HOMeVal-D-Hmp, the
                        carboxyl group of D-Hmp being bound to the amino acid
                        in location 3."

( i x ) FEATURE:
                ( A ) NAME/KEY:
                ( B ) LOCATION: 3
                ( C ) IDENTIFICATION METHOD:
                ( D ) OTHER INFORMATION: /note="MeVal"

( i x ) FEATURE:
                ( A ) NAME/KEY:
                ( B ) LOCATION: 5
                ( C ) IDENTIFICATION METHOD:
                ( D ) OTHER INFORMATION: /note="MePhe"

( i x ) FEATURE:
                ( A ) NAME/KEY:
                ( B ) LOCATION: 6
                ( C ) IDENTIFICATION METHOD:
                ( D ) OTHER INFORMATION: /note="Pro-OPac"

( x i ) SEQUENCE DESCRIPTION: SEQ ID NO:46:

Xaa  Xaa  Xaa  Phe  Xaa  Xaa
1                 5

( 2 ) INFORMATION FOR SEQ ID NO:47:

( i ) SEQUENCE CHARACTERISTICS:
                ( A ) LENGTH: 6 amino acids
                ( B ) TYPE: amino acid
                ( C ) STRANDEDNESS: single -continued ( D ) TOPOLOGY: linear ( i i ) MOLECULE TYPE: peptide ( i x ) FEATURE:
                    ( A ) NAME/KEY:
                    ( B ) LOCATION: 1
                    ( C ) IDENTIFICATION METHOD:
                    ( D ) OTHER INFORMATION: /note= "HCl Glu, its gamma-carboxyl
                            group being protected by cHex group.[HCl H-Glu(OcHex)]"

( i x ) FEATURE:
                    ( A ) NAME/KEY:
                    ( B ) LOCATION: 2
                    ( C ) IDENTIFICATION METHOD:
                    ( D ) OTHER INFORMATION: /note="beta-HOMeVal-D-Hmp, the
                            carboxyl group of D-Hmp being bound to the amino acid
                            in location 3."

( i x ) FEATURE:
                    ( A ) NAME/KEY:
                    ( B ) LOCATION: 3
                    ( C ) IDENTIFICATION METHOD:
                    ( D ) OTHER INFORMATION: /note="MeVal"

( i x ) FEATURE:
                    ( A ) NAME/KEY:
                    ( B ) LOCATION: 5
                    ( C ) IDENTIFICATION METHOD:
                    ( D ) OTHER INFORMATION: /note="MePhe"

( i x ) FEATURE:
                    ( A ) NAME/KEY:
                    ( B ) LOCATION: 6
                    ( C ) IDENTIFICATION METHOD:
                    ( D ) OTHER INFORMATION: /note="Pro-OPac"

( x i ) SEQUENCE DESCRIPTION: SEQ ID NO:47:

Xaa  Xaa  Xaa  Phe  Xaa  Xaa
 1                    5

( 2 ) INFORMATION FOR SEQ ID NO:48:

( i ) SEQUENCE CHARACTERISTICS:
                    ( A ) LENGTH: 8 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY:
                    ( B ) LOCATION: 1
                    ( C ) IDENTIFICATION METHOD:
                    ( D ) OTHER INFORMATION: /note= "Boc-aIle"

( i x ) FEATURE:
                    ( A ) NAME/KEY:
                    ( B ) LOCATION: 2
                    ( C ) IDENTIFICATION METHOD:
                    ( D ) OTHER INFORMATION: /note="MeVal"

( i x ) FEATURE:
                    ( A ) NAME/KEY:
                    ( B ) LOCATION: 3
                    ( C ) IDENTIFICATION METHOD:
                    ( D ) OTHER INFORMATION: /note="Glu(OcHex)"

( i x ) FEATURE:
                    ( A ) NAME/KEY:
                    ( B ) LOCATION: 4
                    ( C ) IDENTIFICATION METHOD:
                    ( D ) OTHER INFORMATION: /note="beta-HOMeVal-D-Hmp, the
                            carboxyl group of D-Hmp being bound to the amino acid
                            in location 5."

( i x ) FEATURE:
    ( A ) NAME/KEY:
    ( B ) LOCATION: 5
    ( C ) IDENTIFICATION METHOD:
    ( D ) OTHER INFORMATION: /note="MeVal"

( i x ) FEATURE:
    ( A ) NAME/KEY:
    ( B ) LOCATION: 7
    ( C ) IDENTIFICATION METHOD:
    ( D ) OTHER INFORMATION: /note="MePhe"

( i x ) FEATURE:
    ( A ) NAME/KEY:
    ( B ) LOCATION: 8
    ( C ) IDENTIFICATION METHOD:
    ( D ) OTHER INFORMATION: /note="Pro-OPac"

( x i ) SEQUENCE DESCRIPTION: SEQ ID NO:48:

Xaa Xaa Xaa Xaa Xaa Phe Xaa Xaa
1               5

( 2 ) INFORMATION FOR SEQ ID NO:49:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note= "Boc-aIle"

( i x ) FEATURE:
        ( A ) NAME/KEY:
        ( B ) LOCATION: 2
        ( C ) IDENTIFICATION METHOD:
        ( D ) OTHER INFORMATION: /note="MeVal"

( i x ) FEATURE:
        ( A ) NAME/KEY:
        ( B ) LOCATION: 3
        ( C ) IDENTIFICATION METHOD:
        ( D ) OTHER INFORMATION: /note="Glu(OcHex)"

( i x ) FEATURE:
        ( A ) NAME/KEY:
        ( B ) LOCATION: 4
        ( C ) IDENTIFICATION METHOD:
        ( D ) OTHER INFORMATION: /note="beta-HOMeVal-D-Hmp, the
            carboxyl group of D-Hmp being bound to the amino acid
            in location 5."

( i x ) FEATURE:
        ( A ) NAME/KEY:
        ( B ) LOCATION: 5
        ( C ) IDENTIFICATION METHOD:
        ( D ) OTHER INFORMATION: /note="MeVal"

( i x ) FEATURE:
        ( A ) NAME/KEY:
        ( B ) LOCATION: 7
        ( C ) IDENTIFICATION METHOD:
        ( D ) OTHER INFORMATION: /note="MePhe"

( x i ) SEQUENCE DESCRIPTION: SEQ ID NO:49:

Xaa Xaa Xaa Xaa Xaa Phe Xaa Pro
1               5

( 2 ) INFORMATION FOR SEQ ID NO:50:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note= "HCl alle"

( i x ) FEATURE:
        ( A ) NAME/KEY:
        ( B ) LOCATION: 2
        ( C ) IDENTIFICATION METHOD:
        ( D ) OTHER INFORMATION: /note="MeVal"

( i x ) FEATURE:
        ( A ) NAME/KEY:
        ( B ) LOCATION: 3
        ( C ) IDENTIFICATION METHOD:
        ( D ) OTHER INFORMATION: /note="Glu(OcHex)"

( i x ) FEATURE:
        ( A ) NAME/KEY:
        ( B ) LOCATION: 4
        ( C ) IDENTIFICATION METHOD:
        ( D ) OTHER INFORMATION: /note="beta-HOMeVal-D-Hmp, the
            carboxyl group of D-Hmp being bound to the amino acid
            in location 5."

( i x ) FEATURE:
        ( A ) NAME/KEY:
        ( B ) LOCATION: 5
        ( C ) IDENTIFICATION METHOD:
        ( D ) OTHER INFORMATION: /note="MeVal"

( i x ) FEATURE:
        ( A ) NAME/KEY:
        ( B ) LOCATION: 7
        ( C ) IDENTIFICATION METHOD:
        ( D ) OTHER INFORMATION: /note="MePhe"

( x i ) SEQUENCE DESCRIPTION: SEQ ID NO:50:

Xaa Xaa Xaa Xaa Xaa Phe Xaa Pro
1               5

( 2 ) INFORMATION FOR SEQ ID NO:51:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: circular ( i i ) MOLECULE TYPE: peptide ( i x ) FEATURE:
        ( A ) NAME/KEY:
        ( B ) LOCATION: 1
        ( C ) IDENTIFICATION METHOD:
        ( D ) OTHER INFORMATION: /note= "alle"

( i x ) FEATURE:
        ( A ) NAME/KEY:
        ( B ) LOCATION: 2
        ( C ) IDENTIFICATION METHOD:
        ( D ) OTHER INFORMATION: /note="MeVal"

( i x ) FEATURE:

(A) NAME/KEY:
(B) LOCATION: 3
(C) IDENTIFICATION METHOD:
(D) OTHER INFORMATION: /note="Glu(OcHex)"

(ix) FEATURE:
(A) NAME/KEY:
(B) LOCATION: 4
(C) IDENTIFICATION METHOD:
(D) OTHER INFORMATION: /note="beta-HOMeVal-D-Hmp, the carboxyl group of D-Hmp being bound to the amino acid in location 5."

(ix) FEATURE:
(A) NAME/KEY:
(B) LOCATION: 5
(C) IDENTIFICATION METHOD:
(D) OTHER INFORMATION: /note="MeVal"

(ix) FEATURE:
(A) NAME/KEY:
(B) LOCATION: 7
(C) IDENTIFICATION METHOD:
(D) OTHER INFORMATION: /note="MePhe"

(ix) FEATURE:
(A) NAME/KEY:
(B) LOCATION: 8
(C) IDENTIFICATION METHOD:
(D) OTHER INFORMATION: /note="Pro, this amino acid being bound to the amino acid in location 1."

(xi) SEQUENCE DESCRIPTION: SEQ ID NO:51:

Xaa Xaa Xaa Xaa Xaa Phe Xaa Pro
1                   5

(2) INFORMATION FOR SEQ ID NO:52:

(i) SEQUENCE CHARACTERISTICS:
(A) LENGTH: 8 amino acids
(B) TYPE: amino acid
(C) STRANDEDNESS: single
(D) TOPOLOGY: circular (ii) MOLECULE TYPE: peptide (ix) FEATURE:
(A) NAME/KEY:
(B) LOCATION: 1
(C) IDENTIFICATION METHOD:
(D) OTHER INFORMATION: /note= "aIle"

(ix) FEATURE:
(A) NAME/KEY:
(B) LOCATION: 2
(C) IDENTIFICATION METHOD:
(D) OTHER INFORMATION: /note="MeVal"

(ix) FEATURE:
(A) NAME/KEY:
(B) LOCATION: 4
(C) IDENTIFICATION METHOD:
(D) OTHER INFORMATION: /note="beta-HOMeVal-D-Hmp, the carboxyl group of D-Hmp being bound to the amino acid in location 5."

(ix) FEATURE:
(A) NAME/KEY:
(B) LOCATION: 5
(C) IDENTIFICATION METHOD:
(D) OTHER INFORMATION: /note="MeVal"

(ix) FEATURE:
(A) NAME/KEY:
(B) LOCATION: 7
(C) IDENTIFICATION METHOD:

-continued (D) OTHER INFORMATION: /note="MePhe"

(ix) FEATURE:
                (A) NAME/KEY:
                (B) LOCATION: 8
                (C) IDENTIFICATION METHOD:
                (D) OTHER INFORMATION: /note="Pro, this amino acid being
                        bound to the amino acid in location 1."

(xi) SEQUENCE DESCRIPTION: SEQ ID NO:52:

Xaa  Xaa  Glu  Xaa  Xaa  Phe  Xaa  Pro
 1                     5

(2) INFORMATION FOR SEQ ID NO:53:

(i) SEQUENCE CHARACTERISTICS:
                (A) LENGTH: 8 amino acids
                (B) TYPE: amino acid
                (C) STRANDEDNESS: single
                (D) TOPOLOGY: circular (ii) MOLECULE TYPE: peptide (ix) FEATURE:
                (A) NAME/KEY:
                (B) LOCATION: 1
                (C) IDENTIFICATION METHOD:
                (D) OTHER INFORMATION: /note= "aIle"

(ix) FEATURE:
                (A) NAME/KEY:
                (B) LOCATION: 2
                (C) IDENTIFICATION METHOD:
                (D) OTHER INFORMATION: /note="MeVal"

(ix) FEATURE:
                (A) NAME/KEY:
                (B) LOCATION: 3
                (C) IDENTIFICATION METHOD:
                (D) OTHER INFORMATION: /note="HONva"

(ix) FEATURE:
                (A) NAME/KEY:
                (B) LOCATION: 4
                (C) IDENTIFICATION METHOD:
                (D) OTHER INFORMATION: /note="beta-HOMeVal-D-Hmp, the
                        carboxyl group of D-Hmp being bound to the amino acid
                        in location 5."

(ix) FEATURE:
                (A) NAME/KEY:
                (B) LOCATION: 5
                (C) IDENTIFICATION METHOD:
                (D) OTHER INFORMATION: /note="MeVal"

(ix) FEATURE:
                (A) NAME/KEY:
                (B) LOCATION: 7
                (C) IDENTIFICATION METHOD:
                (D) OTHER INFORMATION: /note="MePhe"

(ix) FEATURE:
                (A) NAME/KEY:
                (B) LOCATION: 8
                (C) IDENTIFICATION METHOD:
                (D) OTHER INFORMATION: /note="Pro, this amino acid being
                        bound to the amino acid in location 1."

(xi) SEQUENCE DESCRIPTION: SEQ ID NO:53:

Xaa  Xaa  Xaa  Xaa  Xaa  Phe  Xaa  Pro
 1                     5

(2) INFORMATION FOR SEQ ID NO:54:

(  i  ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: circular ( i i ) MOLECULE TYPE: peptide ( i x ) FEATURE:
   ( A ) NAME/KEY:
   ( B ) LOCATION: 1
   ( C ) IDENTIFICATION METHOD:
   ( D ) OTHER INFORMATION: /note= "Hmp-MeVal"

( i x ) FEATURE:
   ( A ) NAME/KEY:
   ( B ) LOCATION: 3
   ( C ) IDENTIFICATION METHOD:
   ( D ) OTHER INFORMATION: /note="MePhe"

( i x ) FEATURE:
   ( A ) NAME/KEY:
   ( B ) LOCATION: 5
   ( C ) IDENTIFICATION METHOD:
   ( D ) OTHER INFORMATION: /note="aIle"

( i x ) FEATURE:
   ( A ) NAME/KEY:
   ( B ) LOCATION: 6
   ( C ) IDENTIFICATION METHOD:
   ( D ) OTHER INFORMATION: /note="MeVal, MeLeu or MeaIle,
         provided that if MeVal, the amino acids at locations
         7 and 8 are aIle and beta-HOMeVal, or Leu and MeThr,
         respectively; if MeLeu or MeaIle, the amino acids at
         locations 7 and 8 are Leu and beta-HOMeVal, respectively"

( i x ) FEATURE:
   ( A ) NAME/KEY:
   ( B ) LOCATION: 7
   ( C ) IDENTIFICATION METHOD:
   ( D ) OTHER INFORMATION: /note="Leu or aIle"

( i x ) FEATURE:
   ( A ) NAME/KEY:
   ( B ) LOCATION: 8
   ( C ) IDENTIFICATION METHOD:
   ( D ) OTHER INFORMATION: /note="MeThr or beta-HOMeVal being
         bound to the Hmp group of the amino acid at location 1"

( x i ) SEQUENCE DESCRIPTION: SEQ ID NO:54:

Xaa Phe Xaa Pro Xaa Xaa Xaa Xaa
 1           5